(12) United States Patent
Adam

(10) Patent No.: US 10,793,531 B2
(45) Date of Patent: Oct. 6, 2020

(54) TRIAZOLE DERIVATIVES AND THEIR USE AS PDE4 ACTIVATORS

(71) Applicant: MIRONID LIMITED, North Lanarkshire (GB)

(72) Inventor: Julia Adam, North Lanarkshire (GB)

(73) Assignee: Mironid Limited, North Lanarkshire (GB)

( * ) Notice: Subject to any disclaimer, the term of this patent is extended or adjusted under 35 U.S.C. 154(b) by 0 days.

(21) Appl. No.: 16/508,001

(22) Filed: Jul. 10, 2019

(65) Prior Publication Data

US 2020/0002296 A1    Jan. 2, 2020

Related U.S. Application Data

(62) Division of application No. 15/559,875, filed as application No. PCT/GB2016/050766 on Mar. 18, 2016, now Pat. No. 10,385,027.

(30) Foreign Application Priority Data

Mar. 20, 2015 (GB) .................................. 1504763.2

(51) Int. Cl.
*C07D 249/08* (2006.01)
*C12Q 1/44* (2006.01)

(52) U.S. Cl.
CPC ............. *C07D 249/08* (2013.01); *C12Q 1/44* (2013.01); *C12Y 301/04053* (2013.01); *G01N 2333/916* (2013.01); *G01N 2500/04* (2013.01); *G01N 2500/20* (2013.01); *G01N 2800/7028* (2013.01)

(58) Field of Classification Search
CPC .......... A61P 11/00; A61P 13/00; A61P 13/08; A61P 13/12; A61P 19/00; A61P 1/00; A61P 1/16; A61P 31/04; A61P 31/06; A61P 31/18; A61P 35/00; A61P 35/02; A61P 37/04; A61P 3/10; A61P 43/00; A61P 5/00; A61P 5/12; A61P 5/16; A61P 5/28; A61P 9/00

See application file for complete search history.

(56) References Cited

U.S. PATENT DOCUMENTS

| | | |
|---|---|---|
| 2005/0137168 A1 | 6/2005 | Gobbi et al. |
| 2009/0186900 A1 | 7/2009 | Vicker et al. |
| 2010/0144733 A1 | 6/2010 | Doyle et al. |
| 2010/0222336 A1 | 9/2010 | Konetzki et al. |
| 2010/0267741 A1 | 10/2010 | Penrose et al. |
| 2012/0053218 A1 | 3/2012 | Brüggemeier et al. |
| 2013/0150341 A1 | 6/2013 | Grauert et al. |
| 2013/0184248 A1 | 7/2013 | Grauert et al. |
| 2014/0302988 A1 | 10/2014 | Gienckle et al. |

FOREIGN PATENT DOCUMENTS

| | | |
|---|---|---|
| EP | 0936221 A1 | 8/1999 |
| WO | 2004071447 A2 | 8/2004 |
| WO | 2007097927 A3 | 1/2008 |
| WO | 2009131956 A1 | 10/2009 |
| WO | 2010131194 A1 | 11/2010 |
| WO | 2010131195 A1 | 11/2010 |
| WO | 2010059838 A3 | 12/2010 |
| WO | 2011127019 A2 | 10/2011 |
| WO | 2013021044 A1 | 2/2013 |
| WO | 2014150326 A1 | 9/2014 |
| WO | 2015175956 A1 | 11/2015 |
| WO | 2016151300 A1 | 9/2016 |
| WO | 2017044828 A1 | 3/2017 |
| WO | 2018060704 A1 | 4/2018 |

OTHER PUBLICATIONS

Mao et al., Thiazolidinediones inhibit MDCK cyst growth through disrupting orientated cell division and apicobasal polarity; American Journal of Physiology-Renal Physiology, vol. 300(6), Jun. 2011 pp. F1375-F1384.

Marchmont et al., A peripheral and an intrinsic enzyme constitute the cyclic AMP phosphodiesterase activity of rat liver plasma membranes; Biochemical Journal, vol. 187, May 1, 1980 pp. 381-392.

Masoum et al., 'Potential pharmacological interventions in polycystic kidney disease; Drugs, vol. 67, Jan. 1, 2007 pp. 2495-2510.

Masyuk et al., Octreotide inhibits hepatic cystogenesis in a rodent model of polycystic liver disease by reducing cholangiocyte adenosine 3',5'-cyclic monophosphate; Gastroenterology, vol. 132, Mar. 2007 pp. 1104-1116.

Meng et al., "An Efficient and Recyclable Heterogeneous Catalytic System for the Synthesis of 1, 2, 4-triazoles using air as the oxidant" RSC Advances: An International Journal to Further Chemical Sciences, vol. 4, No. 17, Jan. 1, 2014 pp. 8612.

Merkle et al., Roles of cAMP and cAMP-dependent protein kinase in the progression of prostate cancer: cross-talk with the androgen receptor; Cellular Signalling, vol. 23, Mar. 2011 pp. 507-515.

Misra et al., Epac1?induced cellular proliferation in prostate cancer cells is mediated by B?Raf/ERK and mTOR signaling cascades; Journal of Cellular Biochemistry, vol. 108, Sep. 1, 2009 pp. 998-1011.

Misra et al., Upregulation of mTORC2 activation by the selective agonist of EPAC, 8-CPT-2Me-cAMP, in prostate cancer cells: Assembly of a multiprotein signaling complex; Journal of Cellular Biochemistry, vol. 113, 2012, pp. 1488-1500.

(Continued)

*Primary Examiner* — Valerie Rodriguez-Garcia
(74) *Attorney, Agent, or Firm* — McNeill Baur PLLC

(57) ABSTRACT

Compounds of Formula (I), which are activators of long form cyclic nucleotide phosphodiesterase-4 (PDE4) enzymes, are provided. Methods and uses of these compounds for the treatment or prevention of disorders requiring a reduction of second messenger responses mediated by cyclic 3',5'-adenosine monophosphate (cAMP) are also described.

10 Claims, 9 Drawing Sheets

(56) References Cited

OTHER PUBLICATIONS

Nayjib et al., In vivo administration of a PKA type I inhibitor (Rp-8-Br-cAMPS) restores T-cell responses in retrovirus-infected mice; The Open Immunology Journal, vol. 170, 2008, pp. 20-24.
Parker et al., Insulin-like growth factor-1 induces hyperproliferation of PKD1 cystic cells via a Ras/Raf dependent signalling pathway; Kidney International, vol. 72(2), Mar. 28, 2007, pp. 157-165.
Persani et al., Induction of Specific Phosphodiesterase Isoforms by Constitutive Activation of the cAMP Pathway in Autonomous Thyroid Adenomas; The Journal of Clinical Endocrinology & Metabolism, vol. 85, Aug. 1, 2000, pp. 2872-2878.
Richter, et al., Dimerization of the Type 4 cAMP-specific Phosphodiesterases Is Mediated by the Upstream Conserved Regions (UCRs)*; The Journal of Biological Chemistry, vol. 277, Oct. 25, 2002, pp. 40212-40221.
Shankar et al., The role of CREB as a proto-oncogene in hematopoiesis and in acute myeloid leukemia; Cancer Cell, vol. 7, Apr. 2005, pp. 351-362.
Strazzabosco et al., polycystic liver diseases: congenital disorders of cholangiocyte signaling; Gastroenterology, vol. 140, Jun. 1, 2011, pp. 1855-1859.
Sun et al., Drug discovery for polycystic kidney disease; Acta Pharmacologica Sinica, vol. 32, Jun. 1, 2011, pp. 805-816.
Sussman et al., Phosphodiesterase 1A Modulates Cystogenesis in Zebrafish; Journal of the American Society of Nephrology, vol. 25, Oct. 2014, pp. 2222-2230.
Takiar et al., Polycystic kidney disease: pathogenesis and potential therapies; Biochimica et Biophysica Acta, vol. 1812, Oct. 2011, pp. 1337-1343.
Thompson et al., G protein-coupled receptors disrupted in human genetic disease; Methods in Molecular Biology, vol. 448, Jan. 1, 2008, pp. 109-137.
Thompson et al., Multiple cyclic nucleotide phosphodiesterase activities from rat brain; Biochemistry, vol. 10, Jan. 19, 1971, pp. 311-316.
Torres et al., Effective treatment of an orthologous model of autosomal dominant polycystic kidney disease; Nature Medicine, vol. 10, Apr. 2004, pp. 363-364.
Tritos et al., Advances in medical therapies for Cushing's syndrome; Discovery Medicine, vol. 13, Feb. 2012, pp. 171-179.
United Kingdom Search Report for GB Application No. 1504763.2 dated Dec. 15, 2015, 5 pages.
United Kingdom Search Report issued in application No. GB1805527.7 dated Nov. 21, 2018, 2 pages.
Vezzosi et al., Phosphodiesterases in endocrine physiology and disease; European Journal of Endocrinology, vol. 165, Aug. 2011, pp. 177-188.
Wade et al. Synthesis of the Triazolo[5,1-a][2,4] benzodiazepine Ring System; The Journal of Organic Chemistry, vol. 44, No. 1, Jan. 1, 1979, pp. 84-88.
Wallace, D., Cyclic AMP-mediated cyst expansion; Biochimica et Biophysica Acta, vol. 1812, Oct. 2011, pp. 1291-1300.
Wang et al., UCR1C is a novel activator of phosphodiesterase 4 (PDE4) long isoforms and attenuates cardiomyocyte hypertrophy; Cellular Signalling, vol. 27, May 2015, 908-922.
Weinstein et al., Minireview: GNAS: Normal and Abnormal Functions; Endocrinology, vol. 145, Dec. 1, 2004, pp. 5459-5464.
Yamaguchi et al., cAMP stimulates the in vitro proliferation of renal cyst epithelial cells by activating the extracellular signal-regulated kinase pathway; Kidney International, vol. 57, Apr. 2000, pp. 1460-1471.
Aandahl et al., Protein kinase A type I antagonist restores immune responses of T cells from HIV-infected patients; The FASEB Journal, vol. 12, Jul. 1, 1998, pp. 855-862.
Agarwal et al., Cyclic AMP intoxication of macrophages by a *Mycobacterium tuberculosis* adenylate cyclase; Nature, vol. 460, Jul. 2, 2009, pp. 98-102.
Ahuja et al., The Adenylate Cyclase Toxins; Critical Reviews in Microbiology, vol. 30, Oct. 19, 2008, pp. 187-196.
Almahariq et al., A novel EPAC-specific inhibitor suppresses pancreatic cancer cell migration and invasion; Molecular Pharmacology, vol. 83, Jan. 2013, pp. 122-128.
Arturi et al., Thyroid hyperfunctioning adenomas with and without Gsp/TSH receptor mutations show similar clinical features; Experimental and Clinical Endocrinology & Diabetes, vol. 106, 1998, pp. 234-236.
Azevedo et al., The transcriptome that mediates increased cyclic adenosine monophosphate signaling in PRKAR1A defects and other settings; Endocrine Practice, vol. 17, Jul. 2011, pp. 2-7.
Baljinnyam et al., Epac1 promotes melanoma metastasis via modification of heparan sulfate; Pigment Cell & Melanoma Research, vol. 24, Apr. 19, 2011, pp. 680-687.
Belibi et al., Novel targets for the treatment of autosomal dominant polycystic kidney disease; Expert Opinion on Investigational Drugs, vol. 19, Mar. 2010 pp. 315-328.
Biebermann et al., The First Activating TSH Receptor Mutation in Transmembrane Domain 1 Identified in a Family with Nonautoimmune Hyperthyroidism; The Journal of Clinical Endocrinology & Metabolism, vol. 86. Sep. 1, 2001, pp. 4429-4433.
Bolger et al., Dimerization of cAMP phosphodiesterase-4 (PDE4) in living cells requires interfaces located in both the UCR1 and catalytic unit domains; Cellular Signaling, vol. 27, Apr. 2015, pp. 756-769.
Breckler et al., Rap-linked cAMP signaling Epac proteins: compartmentation, functioning and disease implications; Cellular Signalling, vol. 23, Aug. 2011, pp. 1257-1266.
Burgin et al., Design of phosphodiesterase 4D (PDE4D) allosteric modulators for enhancing cognition with improved safety; Nature Biotechnology, vol. 28, Jan. 28, 2010, pp. 63-70.
Calvi et al., The PTH/PTHrP receptor in Jansen's metaphyseal chondrodysplasia; Journal of Endocrinological Investigation, vol. 23, Sep. 2000, pp. 545-554.
Cho et al., CREB and Leukemogenesis; Critical reviews in oncogenesis, vol. 16, 2011, pp. 37-46.
Crans-Vargas et al., Expression of cyclic adenosine monophosphate response-element binding protein in acute leukemia; Blood, vol. 99, May 2002, pp. 2617-2619.
Diaz et al., McCune-Albright Syndrome and Disorders Due to Activating Mutations of GNAS1; Journal of Pediatric Endocrinology and Metabolism, vol. 20, Apr. 4, 2011, pp. 853-880.
Duprez et al., Germline mutations in the thyrotropin receptor gene cause non-autoimmune autosomal dominant hyperthyroidism; Nature Genetics, vol. 7, Jul. 1994, pp. 396-401.
Francis, et al. A Convenient Synthesis of 3, 5-Disubstituted-1, 2, 4-Triazoles; Tetrahedron Letters, Pergamon, GB, vol. 28, No. 43 Jan. 1, 1987, pp. 5133-5136.
Gattone et al., Inhibition of renal cystic disease development and progression by a vasopressin V2 receptor antagonist; Nature Medicine, vol. 9, Oct. 2003, pp. 1323-1326.
Gevers et al., Somatostatin analogues for treatment of polycystic liver disease; Current Opinion in Gastroenterology, vol. 27, May 2011, pp. 294-300.
Gong et al., Somatostatin stimulates ductal bile absorption and inhibits ductal bile secretion in mice via SSTR2 on cholangiocytes; American Journal of Physiology-Cell Physiology, vol. 284, May 1, 2003, pp. C1205-C1214.
Grange et al., The cAMP-specific Phosphodiesterase PDE4D3 Is Regulated by Phosphatidic Acid Binding; Journal of Biological Chemistry, vol. 275, Aug. 9, 2000, pp. 33379-33387.
Gurney et al., Small molecule allosteric modulators of phosphodiesterase 4; Handbook of Experimental Pharmacology, vol. 204, 2011, pp. 167-192.
Henderson et al., The cAMP phosphodiesterase-4D7 (PDE4D7) is downregulated in androgen-independent prostate cancer cells and mediates proliferation by compartmentalising cAMP at the plasma membrane of VCaP prostate cancer cells; British Journal of Cancer, vol. 110, Mar. 4, 2014, pp. 1278-1287.
Holm et al., Impaired Secretion of IL-10 by T Cells from Patients with Common Variable Immunodeficiency—Involvement of Protein Kinase A Type I; Journal of Immunology, vol. 170, Jun. 1, 2003, pp. 5772-5777.

(56) References Cited

OTHER PUBLICATIONS

Horvath et al., A cAMP-specific phosphodiesterase (PDE8B) that is mutated in adrenal hyperplasia is expressed widely in human and mouse tissues: a novel PDE8B isoform in human adrenal cortex; European Journal of Human Genetics, vol. 16, Oct. 2008, pp. 1245-1253.

Horvath et al., A genome-wide scan identifies mutations in the gene encoding phosphodiesterase 11A4 (PDE11A) in individuals with adrenocortical hyperplasia; Nature Genetics, vol. 38, Jun. 11, 2006, pp. 794-800.

Horvath et al., Adrenal Hyperplasia and Adenomas Are Associated with Inhibition of Phosphodiesterase 11A in Carriers of PDE11A Sequence Variants That Are Frequent in the Population; Cancer Research, vol. 66, Dec. 2006, pp. 11571-11575.

Horvath et al., Functional Phosphodiesterase 11A Mutations May Modify the Risk of Familial and Bilateral Testicular Germ Cell Tumors; Cancer Research, vo. 69, Jul. 2009, pp. 5301-5306.

Horvath et al., Mutation in PDE8B, a cyclic AMP-specific phosphodiesterase in adrenal hyperplasia; The New England Journal of Medicine, vol. 358, Feb. 2008, pp. 750-752.

Houslay et al., The Multienzyme PDE4 Cyclic Adenosine Monophosphate-Specific Phosphodiesterase Family: Intracellular Targeting, Regulation, and Selective Inhibition by Compounds Exerting Anti-inflammatory and Antidepressant Actions; Advances in Pharmacology vol. 44, 1998, pp. 225-234.

Houslay, et al., cAMP-Specific phosphodiesterase-4 enzymes in the cardiovascular system: a molecular toolbox for generating compartmentalized cAMP signalling; Circulation Research, vol. 100, Apr. 13, 2007, pp. 950-966.

Houslay, et al., Phosphodiesterase-4 as a therapeutic target; Drug Discovery Today, vol. 10, No. 22, Nov. 2005, pp. 1503-1519.

Houslay, M.D., PDE4 cAMP-specific phosphodiesterases; Progress in Nucleic Acid Research and Molecular Biology, vol. 69, May 7, 2001, pp. 249-315.

International Search Report of International Application No. PCT/GB2016/050766 dated May 13, 2016, 13 pages.

Janssen et al., Congenital disorders of glycosylation in hepatology: the example of polycystic liver disease; Journal of Hepatology, vol. 52, Mar. 2010, pp. 432-440.

Karges et al., TSH receptor mutation V509A causes familial hyperthyroidism by release of interhelical constraints between transmembrane helices TMH3 and TMH5; Journal of Endocrinology, vol. 186, Aug. 2005, pp. 377-385.

Kosugi et al., Characterization of heterogeneous mutations causing constitutive activation of the luteinizing hormone receptor in familial male precocious puberty; Human Molecular Genetics, vol. 4, Feb. 1, 1995, pp. 183-188.

Lania et al., cAMP pathway and pituitary tumorigenesis; Annales d'Endocrinologie, vol. 73, Apr. 2012, pp. 73-75.

Lania et al., G protein mutations in endocrine diseases; European Journal of Endocrinology, vol. 145, Nov. 2001, pp. 543-559.

Latronico et al., A novel mutation of the luteinizing hormone receptor gene causing male gonadotropin-independent precocious puberty; The Journal of Clinical Endocrinology and Metabolism, vol. 80, Aug. 1, 1995, pp. 2490-2494.

Lau et al., Development of a novel in vitro model to predict hepatic clearance using fresh, cryopreserved, and sandwich-cultured hepatocytes; Drug Metabolism and Disposition, vol. 30, Aug. 20, 2002, pp. 1446-1454.

Levy et al., Phosphodiesterase function and endocrine cells: links to human disease and roles in tumor development and treatment; Current Opinion in Pharmacology, vol. 11, Dec. 2011, pp. 689-697.

Libé et al., Frequent Phosphodiesterase 11A Gene (PDE11A) Defects in Patients with Carney Complex (CNC) Caused by PRKAR1A Mutations: PDE11A May Contribute to Adrenal and Testicular Tumors in CNC as a Modifier of the Phenotype; The Journal of Clinical Endocrinology and Metabolism, vol. 96, Jan. 1, 2011, pp. E208-E214.

Libé et al., Phosphodiesterase 11A (PDE11A) and Genetic Predisposition to Adrenocortical Tumors; Cancer Research, vol. 14, Jun. 2008, pp. 4016-4024.

Lorenz et al., The cAMP/Epac1/Rap1 Pathway in Pancreatic Carcinoma; Pancreas, vol. 37, Jul. 2008, pp. 102-103.

Lugnier, C., Cyclic nucleotide phosphodiesterase (PDE) superfamily: A new target for the development of specific therapeutic agents; Pharmacology & Therapeutics, vol. 109, 2006, pp. 366-398.

Ma et al., Mutations of HNF-1? inhibit epithelial morphogenesis through dysregulation of SOCS-3; Proceedings of the National Academy of Sciences of the United States of America, vol. 104, Dec. 18, 2007, pp. 20386-20391.

Mackenzie et al., Long PDE4 cAMP specific phosphodiesterases are activated by protein kinase A-mediated phosphorylation of a single serine residue in Upstream Conserved Region 1 (UCR1); British Journal of Pharmacology, vol. 136, Jun. 2002, pp. 421-433.

Mancusi et al., HNF-1? mutation affects PKD2 and SOCS3 expression causing renal cysts and diabetes in MODY5 kindred; Journal of Nephrology, vol. 26, Jan. 2013, pp. 207-212.

TRIAZOLE DERIVATIVES AND THEIR USE AS PDE4 ACTIVATORS

This application is a divisional application of U.S. application Ser. No. 15/559,875, filed Sep. 20, 2017, which is a national phase entry pursuant to 35 U.S.C. § 371 of International Application No. PCT/GB2016/050766, filed Mar. 18, 2016, which claims the benefit of GB Application No. 1504763.2, filed Mar. 20, 2015, each of which is incorporated by reference herein in its entirety for any purpose.

FIELD OF THE INVENTION

The present invention relates to compounds of Formula I or Formula II, which are activators of long form cyclic nucleotide phosphodiesterase-4 (PDE4) enzymes (isoforms) and to therapies using these activators. In particular, the invention relates to these activator compounds for use in a method for the treatment or prevention of disorders requiring a reduction of second messenger responses mediated by cyclic 3',5'-adenosine monophosphate (cAMP).

BACKGROUND TO THE INVENTION

Cyclic 3',5'-adenosine monophosphate—"cAMP"—is a critical intracellular biochemical messenger that is involved in the transduction of the cellular effects of a variety of hormones, neurotransmitters, and other extracellular biological factors in most animal and human cells. The intracellular concentration of cAMP is controlled by the relative balance between its rate of production and degradation. cAMP is generated by biosynthetic enzymes of the adenylyl cyclase superfamily and degraded by members of the cyclic nucleotide phosphodiesterase (PDE) superfamily. Certain members of the PDE superfamily, such as PDE4, specifically degrade cAMP, while others either specifically degrade cyclic guanosine monophosphate (cGMP) or degrade both cAMP and cGMP. PDE4 enzymes inactivate cAMP, thereby terminating its signalling, by hydrolysing cAMP to 5'-AMP (Lugnier, C. Pharmacol Ther. 109: 366-398, 2006).

Four PDE4 genes (PDE4A, PDE4B, PDE4C and PDE4D) have been identified, each of which encodes a number of different enzyme isoforms through the use of alternative promoters and mRNA splicing. On the basis of their primary structures, the catalytically active PDE4 splice variants can be classified as "long", "short" or "super-short" forms (Houslay, M. D. Prog Nucleic Acid Res Mol Biol. 69: 249-315, 2001). A "dead short" form also exists, which is not catalytically active (Houslay, M. D., Baillie, G. S. and Maurice, D. H. Circ Res. 100: 950-66, 2007). PDE4 long forms have two regulatory regions, called upstream conserved regions 1 and 2 (UCR1 and UCR2), located between their isoform-specific N-terminal portion and the catalytic domain. The UCR1 domain is absent in short forms, whereas the super-short forms not only lack UCR1, but also have a truncated UCR2 domain (Houslay, M. D., Schafer, P. and Zhang, K. Drug Discovery Today 10: 1503-1519, 2005).

PDE4 long forms, but not short forms, associate into dimers within cells (Richter, W and Conti, M. J. Biol. Chem. 277: 40212-40221, 2002; Bolger, G. B. et al., Cell. Signal. 27: 756-769, 2015). A proposed negative allosteric modulation of PDE4 long forms by small molecules has been reported (Burgin A. B. et al., Nat. Biotechnol. 28: 63-70, 2010; Gurney M. E. et al., Handb. Exp. Pharmacol. 204: 167-192, 2011).

It is known in the art that PDE4 long forms may be activated by endogenous cellular mechanisms, such as phosphorylation (MacKenzie, S. J. et al., Br. J. Pharmacol. 136: 421-433, 2002) and phosphatidic acid (Grange et al., J. Biol. Chem. 275: 33379-33387, 2000). Activation of PDE4 long forms by ectopic expression of a 57 amino acid protein (called 'UCR1C') whose precise sequence reflects part of that of the upstream conserved region 1 of PDE4D ('UCR1C' sequence reflects that of amino acids 80-136 while UCR is amino acids 17-136: numbering based on the PDE4D3 long isoform) has recently been reported (Wang, L. et al., Cell. Signal. 27: 908-922, 2015: "UCR1C is a novel activator of phosphodiesterase 4 (PDE4) long isoforms and attenuates cardiomyocyte hypertrophy"). The authors hypothesised that PDE4 activation might be used as a potential therapeutic strategy for preventing cardiac hypertrophy.

Small molecules that act as activators of PDE4 long forms have not previously been disclosed. Small molecule activators would be desirable for a number of reasons, including ease of manufacture and formulation and improved pharmacokinetic properties.

It is amongst the objects of the present invention to provide small molecule activators of at least one of the long forms of PDE4 of Formula I or Formula II for use in a method of therapy, as well as specific disease treatment or prevention.

SUMMARY OF THE INVENTION

In a first aspect of the invention, there is provided a compound of Formula 1:

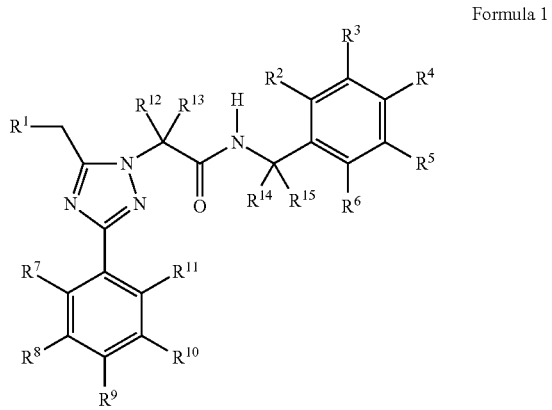

Formula 1

Wherein
$R^1$ is H, (C1-4) alkyl or (C1-4)alkyloxy, the (C1-4)alkyl and (C1-4)alkyloxy groups being optionally substituted with 1 to 3 fluoros;

$R^2$ and $R^6$ are independently selected from H, (C1-4)alkyl, (C1-4)alkyloxy, —CN and halogen, the (C1-4)alkyl and (C1-4)alkyloxy groups being optionally substituted with 1 to 3 fluoros;

$R^3$, $R^4$ and $R^5$ are independently selected from H, (C1-4) alkyl, (C1-4)alkyloxy, (C1-4)alkylsulfonyl, C(O)—NR$^{16}$R$^{17}$, C(O)—OR$^{16}$, S(O)$_2$—NR$^{16}$R$^{17}$, —CN and halogen, the (C1-4)alkyl and (C1-4)alkyloxy groups being optionally substituted with 1 to 3 fluoros;

$R^7$, $R^8$, $R^{10}$ and $R^{11}$ are independently selected from H and F;

$R^9$ is selected from H, (C1-4)alkyl, (C1-4)alkyloxy, (C1-4)alkylsulfonyl, C(O)—NR$^{16}$R$^{17}$, C(O)—OR$^{16}$, S(O)$_2$—

NR$^{16}$R$^{17}$, CN and halogen, the (C1-4)alkyl and (C1-4)alkyloxy groups being optionally substituted with 1 to 3 fluoros;

R$^{12}$, R$^{13}$, R$^{14}$ and R$^{15}$ are independently selected from H and (C1-4)alkyl;

each R$^{16}$ and R$^{17}$, when present, is independently selected from H and (C1-4)alkyl;

or a pharmaceutically acceptable salt thereof.

The triazole derivative compounds of Formula 1 are shown in the Examples to activate PDE4 long form enzymes, and to provide therapeutically useful effects on cells.

In one embodiment, the present invention provides a compound of Formula 1 for use in therapy. In another embodiment, the therapy is the treatment or prevention of a disease or disorder mediated by excessive intracellular cAMP signalling. In these diseases, a reduction of second messenger responses mediated by cyclic 3',5'-adenosine monophosphate (CAMP) should provide a therapeutic benefit. Also provided is a method of treating or preventing a disease or disorder mediated by excessive intracellular cAMP signalling, comprising the step of administering an effective amount of a compound of Formula 1 to a patient in need thereof. Also provided is the use of a compound of Formula 1 in the manufacture of a medicament for treating or preventing a disease or disorder mediated by excessive intracellular cAMP signalling.

The invention also provides a compound of Formula 2, for use in therapy:

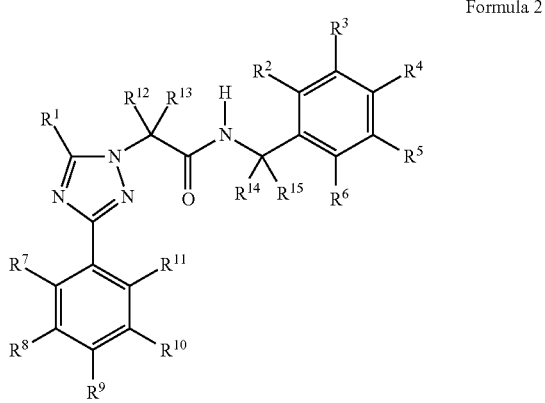

Formula 2 wherein

R$^1$ is H, (C1-6)alkyl or (C3-7)cycloalkyl, the (C1-6)alkyl and (C3-7)cycloalkyl groups being optionally substituted with 1 to 3 substituents selected from OH, (C1-4)alkyloxy, (C1-4)alkyl-sulfonyl, C(O)—NR$^{16}$R$^{17}$, C(O)—OR$^{16}$, S(O)$_2$—NR$^{16}$R$^{17}$, CN and halogen;

R$^2$ and R$^6$ are independently selected from H, (C1-4)alkyl, (C1-4)alkyloxy, —CN and halogen, the (C1-4)alkyl and (C1-4)alkyloxy groups being optionally substituted with 1 to 3 fluoros;

R$^3$, R$^4$ and R$^5$ are independently selected from H, (C1-4)alkyl, (C1-4)alkyloxy, (C1-4)alkylsulfonyl, C(O)—NR$^{16}$R$^{17}$, C(O)—OR$^{16}$, S(O)$_2$—NR$^{16}$R$^{17}$, —CN and halogen, the (C1-4)alkyl and (C1-4)alkyloxy groups being optionally substituted with 1 to 3 fluoros;

R$^7$, R$^8$, R$^{10}$ and R$^{11}$ are independently selected from H and F;

R$^9$ is selected from H, (C1-4)alkyl, (C1-4)alkyloxy, (C1-4)alkylsulfonyl, C(O)—NR$^{16}$R$^{17}$, C(O)—OR$^{16}$, S(O)$_2$—

NR$^{16}$R$^{17}$, —CN and halogen, the (C1-4)alkyl and (C1-4)alkyloxy groups being optionally substituted with 1 to 3 fluoros;

R$^{12}$, R$^{13}$, R$^{14}$ and R$^{15}$ are independently selected from H and (C1-4)alkyl;

each R$^{16}$ and R$^{17}$, when present, is independently selected from H and (C1-4)alkyl;

or a pharmaceutically acceptable salt thereof.

Compounds of Formula 2 are shown in the Examples to activate a long form cyclic phosphodiesterase-4 (PDE4) enzyme and to provide therapeutically useful effects on cells.

A compound of Formula 1 or Formula 2 can be provided in a pharmaceutical composition comprising a pharmaceutically acceptable excipient.

In certain embodiments of the foregoing aspects, the compounds of the invention are provided for the treatment or prevention of a condition selected from hyperthyroidism, Jansens's metaphyseal chondrodysplasia, hyperparathyroidism, familial male-limited precocious puberty, pituitary adenomas, Cushing's disease, polycystic kidney disease, polycystic liver disease, McCune-Albright syndrome, cholera, whooping cough, anthrax, tuberculosis, HIV, AIDS, Common Variable Immunodeficiency (CVID), melanoma, pancreatic cancer, leukaemia, prostate cancer, adrenocortical tumours, testicular cancer, primary pigmented nodular adrenocortical diseases (PPNAD), Carney Complex, autosomal dominant polycystic kidney disease (ADPKD), autosomal recessive polycystic kidney disease (ARPKD), maturity onset diabetes of young type 5 (MODY5), or cardiac hypertrophy.

In a further aspect, the invention provides a method of preparing a compound of Formula 1 or a pharmaceutically acceptable salt thereof, comprising the step of reacting a compound of Formula 1A

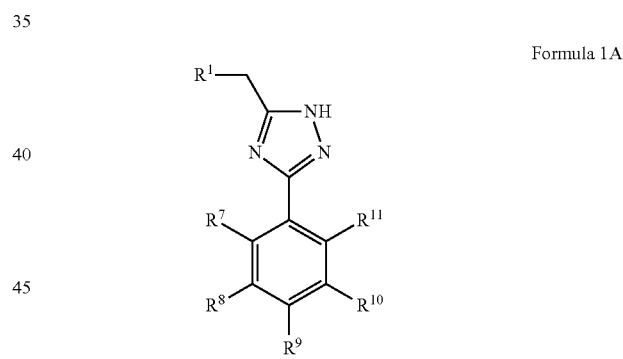

Formula 1A with a compound of Formula 1B

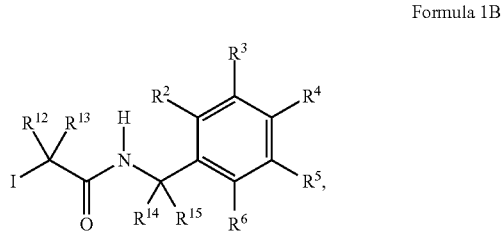

Formula 1B wherein R1-R15 are defined for Formula 1 above.

The invention also provides a method of preparing a compound of Formula 1 or a pharmaceutically acceptable salt thereof, comprising the step of reacting a compound of Formula 1C Formula 1C

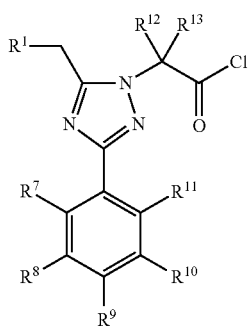

with a compound of Formula 1D

Formula 1D

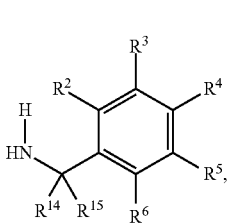

wherein R1-R15 are defined for Formula 1 above.

Intermediates of Formula 1A and 1C are also provided by the invention.

In yet another aspect, the invention provides a method of identifying a compound able to activate a long form PDE4 enzyme, comprising the steps of:
 a. contacting a long form PDE4 enzyme with a candidate compound;
 b. determining whether the candidate compound activates the enzyme to at least the same level as a compound of Formula 1 or Formula 2.

The method may be performed according to one of the methods in the Examples. In one embodiment, the method further comprises the prior or subsequent step of determining whether the candidate compound activates a short or super-short PDE4 enzyme. A compound that activates a long form PDE4 and does not activate a short or super-short form PDE4 is selective for long form PDE4. One or more of the compounds exemplified herein may be used as the reference or control.

DETAILED DESCRIPTION OF THE INVENTION

Figure 1:
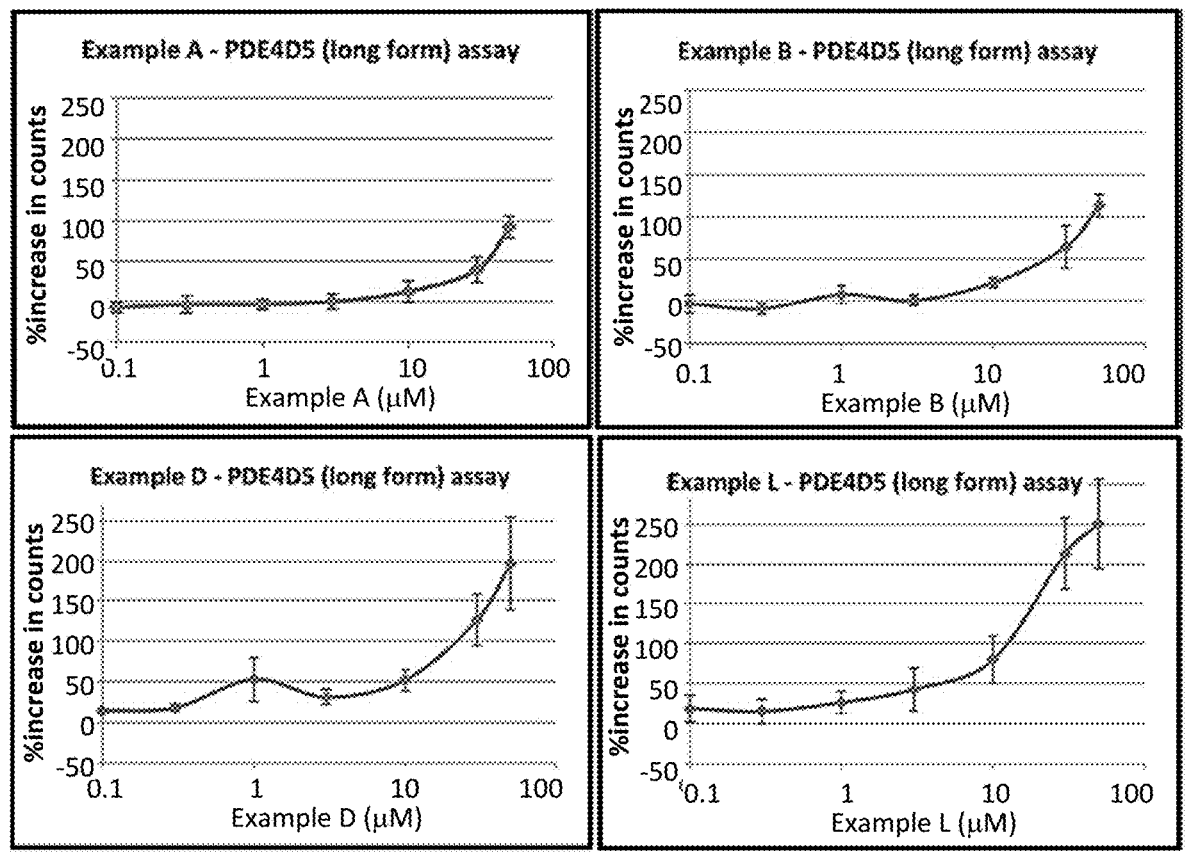
FIG. 1 shows activation of PDE4D5, a long form of PDE4, by Examples A, B, D and L.

The invention is based on the surprising identification of new compounds that are able to activate long isoforms of PDE4 enzymes. The compounds are small molecules and so are expected to be easier and cheaper to make and formulate into pharmaceuticals than large biological molecules such as polypeptides, proteins or antibodies. The compounds can be chemically synthesized, as demonstrated in the Examples.

The Examples demonstrate that a number of compounds of Formula 1 and Formula 2 are able to activate long isoforms of PDE4. The Examples go on to demonstrate that certain tested compounds of the invention: do not activate a short form of PDE4, (thereby demonstrating selectivity for activation of PDE4 long forms over PDE4 short forms); reduce intracellular cAMP levels in human and dog cells; inhibit and even reverse in vitro cyst formation in human and dog cells; inhibit the proliferation of human prostate cancer cells; and have favourable pharmacokinetic properties. The compounds of the invention are therefore surprisingly advantageous.

Various embodiments of the invention are described herein. It will be recognised that features specified in each embodiment may be combined with other specified features to provide further embodiments.

Compounds—Formula 1

A first aspect provides a compound of Formula 1, as set out above.

In an embodiment of the compound of Formula 1, $R^7$ and $R^{11}$ are H.

In an embodiment of the compound of Formula 1, $R^{11}$, $R^{12}$, $R^{13}$, $R^{14}$ and $R^{15}$ are H.

In an embodiment of the compound of Formula 1, $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1, $R^7$, $R^{11}$, $R^{12}$, $R^{13}$, $R^{14}$ and $R^{15}$ are H and $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1, $R^1$ is H, methyl, or methoxy.

In an embodiment of the compound of Formula 1, $R^1$ is methyl.

In an embodiment of the compound of Formula 1, $R^2$ and $R^6$ are each independently selected from H and halogen.

In an embodiment of the compound of Formula 1, $R^2$ and $R^6$ are each independently selected from H and fluoro.

In an embodiment of the compound of Formula 1, $R^2$ and $R^6$ are each H.

In an embodiment of the compound of Formula 1, $R^3$, $R^4$ and $R^5$ are each independently selected from H, halogen, CN, (C1-4)alkyl and (C1-4)alkyloxy, the (C1-4)alkyl and (C1-4)alkyloxy groups being optionally substituted with 1 to 3 fluoros.

In an embodiment of the compound of Formula 1, $R^3$ and $R^5$ are each independently selected from H, fluoro, chloro, methoxy, CN, trifluoromethyl, methoxy and trifluoromethoxy.

In an embodiment of the compound of Formula 1, $R^4$ is selected from H, fluoro and methoxy.

In an embodiment of the compound of Formula 1, $R^9$ is selected from methyl, chloro and trifluoromethoxy.

In an embodiment of the compound of Formula 1, $R^9$ is chloro.

In an embodiment of the compound of Formula 1, one of $R^8$ and $R^{10}$ is H and the other is fluoro.

In an embodiment of the compound of Formula 1, $R^8$ and $R^{10}$ are both H.

In an embodiment of the compound of Formula 1, $R^9$ is chloro, one of $R^8$ and $R^{10}$ is H and the other of $R^8$ and $R^{10}$ is fluoro.

In an embodiment, the compound is selected from:
N-(3-Fluorobenzyl)-2-[3-(4-chloro-3-fluorophenyl)-5-ethyl-1H-1,2,4-triazol-1-yl]acetamide;
N-Benzyl-2-[3-(4-chlorophenyl)-5-methoxymethyl-1H-1,2,4-triazol-1-yl]acetamide;
N-Benzyl-2-[3-(4-chlorophenyl)-5-methyl-1H-1,2,4-triazol-1-yl]acetamide;
N-(3-Fluorobenzyl)-2-{3-[4-(trifluoromethoxy)-phenyl]-5-methoxymethyl-1H-1,2,4-triazol-1-yl}acetamide;
N-(3-Chlorobenzyl)-2-[3-(4-chloro-3-fluorophenyl)-5-ethyl-1H-1,2,4-triazol-1-yl]acetamide;
N-(3-Cyanobenzyl)-2-[3-(4-chloro-3-fluorophenyl)-5-ethyl-1H-1,2,4-triazol-1-yl]acetamide;
N-[3-(Trifluoromethypenzyl]-2-[3-(4-chloro-3-fluorophenyl)-5-ethyl-1H-1,2,4-triazol-1-yl]acetamide;
N-(3-Methoxybenzyl)-2-[3-(4-chloro-3-fluorophenyl)-5-ethyl-1H-1,2,4-triazol-1-yl]acetamide;
N-[3-(Trifluoromethoxy)benzyl]-2-[3-(4-chloro-3-fluorophenyl)-5-ethyl-1H-1,2,4-triazol-1-yl]acetamide;
N-(2-Fluorobenzyl)-2-[3-(4-chloro-3-fluorophenyl)-5-ethyl-1H-1,2,4-triazol-1-yl]acetamide;
N-(4-Fluorobenzyl)-2-[3-(4-chloro-3-fluorophenyl)-5-ethyl-1H-1,2,4-triazol-1-yl]acetamide;
N-(3,4-Dimethoxybenzyl)-2-[3-(4-chloro-3-fluorophenyl)-5-ethyl-1H-1,2,4-triazol-1-yl]acetamide; and pharmaceutically acceptable salts thereof.

Compounds—Formula 2

A further aspect provides a compound of Formula 2, as set out above.

In an embodiment of the compound of Formula 2, $R^7$ and $R^{11}$ are H.

In an embodiment of the compound of Formula 2, $R^{11}$, $R^{12}$, $R^{13}$, $R^{14}$ and $R^{15}$ are H.

In an embodiment of the compound of Formula 2, $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 2, $R^7$, $R^{11}$, $R^{12}$, $R^{13}$, $R^{14}$ and $R^{15}$ are H and $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 2, $R^1$ is H, methyl, or methoxy.

In an embodiment of the compound of Formula 2, $R^1$ is methyl.

In an embodiment of the compound of Formula 2, $R^2$ and $R^6$ are each independently selected from H and halogen.

In an embodiment of the compound of Formula 2, $R^2$ and $R^6$ are each independently selected from H and fluoro.

In an embodiment of the compound of Formula 2, $R^2$ and $R^6$ are each H.

In an embodiment of the compound of Formula 2, $R^3$, $R^4$ and $R^5$ are each independently selected from H, halogen, CN, (C1-4)alkyl and (C1-4)alkyloxy, the (C1-4)alkyl and (C1-4)alkyloxy groups being optionally substituted with 1 to 3 fluoros.

In an embodiment of the compound of Formula 2, $R^3$ and $R^5$ each independently selected from H, fluoro, chloro, methoxy, CN, trifluoromethyl, methoxy and trifluoromethoxy.

In an embodiment of the compound of Formula 2, $R^4$ is selected from H, fluoro and methoxy.

In an embodiment of the compound of Formula 2, $R^9$ is selected from methyl, chloro and trifluoromethoxy.

In an embodiment of the compound of Formula 2, $R^9$ is chloro.

In an embodiment of the compound of Formula 2, one of $R^8$ and $R^{10}$ is H and the other is fluoro.

In an embodiment of the compound of Formula 2, $R^8$ and $R^{10}$ are both H.

In an embodiment of the compound of Formula 2, $R^9$ is chloro, one of $R^8$ and $R^{10}$ is H and the other of $R^8$ and $R^{10}$ is fluoro.

Intermediates of Formula 1A and 1C

Further aspects provide compounds of Formula 1A and 1C, as set out above.

In an embodiment of the compound of Formula 1A, $R^7$ and $R^{11}$ are H.

In an embodiment of the compound of Formula 1A, $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1A, $R^7$ and $R^{11}$ are H and $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1A, $R^1$ is H, methyl, or methoxy.

In an embodiment of the compound of Formula 1A, $R^1$ is methyl.

In an embodiment of the compound of Formula 1A, $R^9$ is selected from methyl, chloro and trifluoromethoxy.

In an embodiment of the compound of Formula 1A, $R^9$ is chloro.

In an embodiment of the compound of Formula 1A, one of $R^8$ and $R^{10}$ is H and the other is fluoro.

In an embodiment of the compound of Formula 1A, $R^8$ and $R^{10}$ are both H.

In an embodiment of the compound of Formula 1A, $R^9$ is chloro, one of $R^8$ and $R^{10}$ is H and the other of $R^8$ and $R^{10}$ is fluoro.

In an embodiment of the compound of Formula 1C, $R^7$ and $R^{11}$ are H.

In an embodiment of the compound of Formula 1C, $R^{11}$, $R^{12}$ and $R^{13}$ are H.

In an embodiment of the compound of Formula 1C, $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1C, $R^7$, $R^{11}$, $R^{12}$ and $R^{13}$ are H and $R^9$ is selected from (C1-4)alkyl, (C1-4)alkyloxy, CN and halogen, the (C1-4)alkyl and (C1-4)alkyloxy groups being optionally substituted with 1 to 3 fluoros.

In an embodiment of the compound of Formula 1C, $R^1$ is H, methyl, or methoxy.

In an embodiment of the compound of Formula 1C, $R^1$ is methyl.

In an embodiment of the compound of Formula 1C, $R^9$ is selected from methyl, chloro and trifluoromethoxy.

In an embodiment of the compound of Formula 1C, $R^9$ is chloro.

In an embodiment of the compound of Formula 1C, one of $R^8$ and $R^{10}$ is H and the other is fluoro.

In an embodiment of the compound of Formula 1C, $R^8$ and $R^{10}$ are both H.

In an embodiment of the compound of Formula 1C, $R^9$ is chloro, one of $R^8$ and $R^{10}$ is H and the other of $R^8$ and $R^{10}$ is fluoro.

Definitions

The term "(C1-4)alkyl" as used herein means a branched or unbranched alkyl group having 1-4 carbon atoms, optionally containing a ring. Examples of (C1-4)alkyl include butyl, isobutyl, cyclobutyl, tertiary butyl, propyl, isopropyl, cyclopropyl, ethyl and methyl. Where specified in the formulae above, (C1-4)alkyl may be substituted, for example with 1 to 3 fluoros. A particularly preferred example of a substituted (C1-4)alkyl is trifluoromethyl. Alternatively (C1-4)alkyl may be unsubstituted.

The term "(C1-4)alkyloxy" means —O—(C1-4)alkyl wherein (C1-4)alkyl has the meaning as defined above. Examples of (C1-4)alkyloxy include methoxy, ethoxy, propoxy, isopropoxy, butyoxy, isobutoxy and tertiary butoxy. Where specified in the formulae above, (C1-4) alkyloxy may be substituted, for example with 1 to 3 fluoros. A particularly preferred example of a substituted (C1-4) alkyloxy is trifluoromethoxy. Alternatively, (C1-4)alkyloxy may be unsubstituted. In the present invention, alkyloxy is attached to the rest of the molecule by the "oxy" moiety.

The term "halogen" means F, Cl, Br or I. F and Cl are particularly preferred.

The 1,2,4-triazole derivatives of Formula 1 or 2 may be prepared by methods known in the art of organic chemistry in general. Suitable methods for constructing 1,2,4-triazole rings are, for example, described in the general reference Katritzky, A. R.: Comprehensive heterocyclic chemistry (First Edition, Pergamon Press, 1984, see especially Volume 5, Part 4A, Five-membered rings with two or more nitrogen atoms). Suitable protecting groups for functional groups which are to be temporarily protected during syntheses are known in the art, for example from Wuts, P. G. M. and Greene, T. W.: Protective Groups in Organic Synthesis, Fourth Edition, Wiley, New York, 2006.

Activation of Long PDE4 Isoforms

PDE4 long isoforms have two regulatory regions, upstream conserved region 1 (UCR1) and upstream conserved region 2 (UCR2). These are between the isoform-specific N-terminal portion and the catalytic domain. The UCR1 domain is missing in the short forms, whereas the super-short forms not only lack UCR1, but also have a N-terminal truncated UCR2 domain (Houslay, M. D., Schafer, P. and Zhang, K. *Drug Discovery Today* 10: 1503-1519, 2005).

There are four PDE4 families, PDE4A, PDE4B, PDE4C and PDE4D. The present invention concerns compounds that are capable of activating one or more of the long isoforms from one or more of these four families. The long isoform PDE4 may therefore be long isoform PDE4A, long isoform PDE4B, long isoform PDE4C or long isoform PDE4D. For the avoidance of doubt, a long isoform PDE4 comprises a UCR1 region. Typically, the long isoform PDE4 is human. UCR1 is conserved within mammalian species (Houslay, M D, Sullivan, M and Bolger G B Adv Pharmacol. 1998; 44:225-34), so in other embodiments, the long isoform PDE4 can be from a non-human mammal.

Without wishing to be bound by theory, PDE4 long form activators of Formula I or Formula II of the present invention are small molecules that are believed to bind directly to PDE4 long forms and induce structural changes that increase, stabilise, uncover and/or maintain the catalytic activity of these enzymes. In the field of pharmacology, and as used herein, a small molecule is defined as a low molecular weight organic compound that may serve as a regulator of biological processes. A small molecule activator according to the present invention has a molecular weight of less than or equal to 700 Daltons. This allows for the possibility to rapidly diffuse across cell membranes and reach intracellular sites of action (Veber, D. F. et al., *J. Med. Chem.* 45: 2615-2623, 2002). The preferred molecular weight for a small molecule activator according to the present invention is greater than or equal to 200 Daltons and less than or equal to 600 Daltons. Especially preferred small molecule activators according to the present invention have molecular weights of greater than or equal to 250 Daltons and less than or equal to 500 Daltons (Lipinski, C. A. *Drug Discovery Today: Technologies* 1: 337-341, 2004).

One suitable method of detecting whether or not a compound is capable of serving as an activator of a PDE4 long form is using a two-step radio-assay procedure described in Experiment 1. In summary, the method involves incubating a PDE4 long form with a test small molecule activator, together with [$^3$H]-labelled cAMP to assess alterations in the breakdown of cAMP to the 5'-adenosine monophosphate (5'-AMP) product. A sample of the reaction mixture from such an incubation is subsequently treated with snake venom 5'-nucleotidase to allow conversion of the nucleotide [$^3$H]-labelled 5'-AMP to the uncharged nucleoside [$^3$H]-labelled adenosine, which can be separated and quantified to assess PDE4 activity and the effect of the test compound (Thompson, W. J. and Appleman, M. M. *Biochemistry* 10: 311-316, 1971, with some modifications as described in: Marchmont, R. J. and Houslay, M. D. *Biochem J.* 187: 381-92, 1980).

Using the above assay procedure, as described in detail in Experiment 1, preferred small molecule activators according to the present invention produce an increase in the background activity of one or more PDE4 long forms of more than 50% at a test compound concentration of 100 micromolar or less. Especially preferred small molecule activators according to the present invention produce an increase in the background activity of one or more PDE4 long forms of more than 50% at a test compound concentration of 10 micromolar, or less, for example 3 micromolar.

The compounds of the present invention may be selective for the long form of the PDE4 enzyme and, as such, do not act or act to a lesser extent as activators of the short or super-short isoforms of the PDE4 enzyme. The short or super-short isoform PDE4 may therefore be short or super-short isoform PDE4A, short or super-short isoform PDE4B, short or super-short isoform PDE4C, or short or super-short isoform PDE4D. For the avoidance of doubt, short and super-short isoforms of PDE4 lack a UCR1 domain. Super-short isoforms comprise a truncated UCR2 domain. Typically, the short or super-short isoform PDE4 is human, but may also be from other mammalian species (where UCR2 is conserved, see Houslay, M D, Sullivan, M and Bolger G B *Adv Pharmacol.* 1998; 44:225-34).

Under the same assay conditions, as described in Experiment 1, the small molecule activators according to the present invention typically produce a less than 50% increase in the background activity of the short or super-short forms of the PDE4A, PDE4B, PDE4C or PDE4D enzymes at a test compound concentration of 100 micromolar, or less.

Typical compounds may therefore provide a positive result in an assay for activation of a long form PDE4 and a negative result in an assay for activation of a short form (or super-short form) of PDE4. In one embodiment, the compound activates long isoform PDE4A and does not activate either of short and super-short isoform PDE4A. In another embodiment, the compound activates long isoform PDE4B and does not activate either of short and super-short isoform PDE4B. In a further embodiment, the compound activates long isoform PDE4C and does not activate either of short and super-short isoform PDE4C. In another embodiment, the compound activates long isoform PDE4D and does not activate either of short and super-short isoform PDE4D.

PDE4 long isoforms include those now known as PDE4A4, PDE4A4/5, PDE4A5, PDE4A8, PDE4A10, PDE4A11, PDE4B1, PDE4B3, PDE4B4, PDE4C1, PDE4C2, PDE4C3, PDE4D3, PDE4D4, PDE4D5, PDE4D7, PDE4D8, PDE4D9 and PDE4D11. Further long isoforms may be or have already been identified or called by different nomenclature from any of the four PDE4 sub-families.

PDE4 short isoforms include PDE4A1, PDE4B2, PDE4D1 and PDE4D2. Further short isoforms may be or have already been identified or called by different nomenclature from any of the four PDE4 sub-families.

PDE4 super-short isoforms include PDE4B5, PDE4D6 and PDE4D10. Further super-short isoforms may be or have already been identified or called by different nomenclature from any of the four PDE4 sub-families.

The Examples below exemplify activity of compounds in human PDE4D5, PDE4A4 and PDE4B1 long isoforms and a lack of activity in the human PDE4B2 short isoform. Details of these isoforms and a number of the other known isoforms, including GenBank accession numbers, are provided in Tables A to D immediately below.

TABLE A

Examples of known PDE4A isoforms
PDE4A

| Isoform | accession | calculated size | SDS-PAGE (kDa) | Type |
|---|---|---|---|---|
| A1 (human) | U97583 | | 83 | S |
| A1 (rodent) | M26715, L27062 | | 76 | S |
| A4* (humanA5) | L20965 | | 125 | L |
| A5 (rodentA4) | L27057 | | 107 | L |
| A7** (human) | U18088 | | 37 | DS |
| A8 (rodent) | L36467 | 88 kDa | 98 | L |
| A10 (human) | AF110461 | 91 kDa | 121 | L |
| A11 (human) | AY618547 | 95 kDa | 126 | L |

L = Long;
S = short;
SS = Super-short;
D = Dead short
*Note that the PDE4A4B clone is correct while PDE4A4A has a cloning artefact and PDE4A4C is a truncation artefact.
**Note that this species is C-as well as N-terminally truncated and so will NOT be detected by pan PDE4A antisera that detect all active forms.

TABLE B

Examples of known PDE4B Isoforms
PDE4B

| Isoform | accession | SDS-PAGE (kDa) | Type |
|---|---|---|---|
| B1 | L20966 | 104 | L |
| B2 | M97515, L20971 | 68 | S |
| B3 | U85048 | 103 | L |
| B4 | AF202733 | 84 | L |
| B5 | EF595686 | 58 | SS |

L = Long;
S = short;
SS = Super-short;
D = Dead short

TABLE C

Examples of known PDE4C Isoforms
PDE4C

| Isoform Name | GenBank | Size (aa) |
|---|---|---|
| PDE4C1 (partial clone) | L20968 | 251* (partial) |
| PDE4C1 | Z46632 | 712* (Long) |
| PDE4C2 | U88712 | 606 (Long) |
| PDE4C3 | U88713 | 700* (Long) |
| PDE4C4 | U66346 | 791* (Long) |
| PDE4C5 | U66347 | 426* |
| PDE4C6 | U66348 | 518* |
| PDE4C7 | U66349 | 427* |

TABLE D

Examples of known PDE4D Isoforms
PDE4D

| Isoform | accession | calculated | SDS-PAGE (kDa) | Type |
|---|---|---|---|---|
| D1 | U50157, U79571 | 66 kDa | 68 | S |
| D2 | U50158, AFO12074 | 66 kDa | 68 | S |
| D3 | L20970, U50159 | 77 kDa | 95 | L |
| D4 | L20969 | 91 kDa | 119 | L |
| D5 | AFO12073 | 84 kDa | 105 | L |
| D6 (m) | AF536975 | 59 kDa | 59 | SS |
| D7 | AF536976 | 85 kDa | 103 | L |
| D8* | AF536977 | 78 kDa | 96 | L |

TABLE D-continued

Examples of known PDE4D Isoforms
PDE4D

| Isoform | accession | calculated | SDS-PAGE (kDa) | Type |
|---|---|---|---|---|
| D9  | AY245867 | 77 kDa | 95 | L |
| D10 | DQ665896 | 58 kDa | 58 | SS |
| D11 | EU489880 | 79 kDa | 95 | L |

L = Long;
S = short;
SS = Super-short;
D = Dead short
*nb D8 was originally called PDE4D6 in the literature
(m) Memory clones are (AY245867, AF536977, AF536976)

Reduction of cAMP

Without wishing to be bound by theory, the compounds of the present invention may function by reducing cAMP levels in one or more intracellular compartments. The PDE4 long form activators of the present invention may thus provide a means to regulate certain cellular processes that are dependent upon cAMP. Excessive intracellular cAMP signalling mediates a number of diseases and disorders. Therefore, the compounds of the invention are expected to be of utility for the treatment of diseases associated with abnormally elevated cAMP levels, increased cAMP-mediated signalling and/or reduced CAMP elimination, enzymatic or otherwise (e.g. via efflux). The treatment is typically of a human, but may also be of a non-human animal, such as a non-human mammal (e.g. veterinary treatment).

In one aspect, the present invention provides a small molecule activator of a PDE4 long form of Formula 1 or Formula 2, for use in a method for the treatment or prevention of disorders where a reduction of second messenger responses mediated by cyclic 3',5'-adenosine monophosphate (cAMP) is required.

For example, gain-of-function gene mutations in proteins involved in driving cAMP signalling upstream of adenylyl cyclase, such as GPCRs and Gsα, can lead to abnormal excessive cAMP activity with pathological consequences (Lania A, Mantovani G, Spada A. *Ann Endocrinol* (Paris). 73: 73-75, 2012; Thompson, M. D. et al., *Methods Mol. Biol.* 448: 109-137, 2008; Weinstein L S, Liu J, Sakamoto A, Xie T, Chen M. *Endocrinology.* 145: 5459-5464, 2004; Lania A, Mantovani G, Spada A. *Eur J Endocrinol.* 145: 543-559, 2001). PDE4 long form activators of the present invention, possessing the ability to accelerate the termination of cAMP action, would therefore be expected to be effective in the treatment, prevention or partial control of diseases characterised by undesirably high cAMP levels, or activity, as detailed below.

Diseases Characterised by Elevated cAMP Levels
Hyperthyroidism

Stimulation of the thyroid-stimulating hormone (TSH) receptor (TSHR) leads to increased generation and release of thyroid hormones, thyroxine and triiodothyronine, through a cAMP-dependent signalling mechanism involving Gsα-mediated activation of adenylyl cyclase. Gain-of-function mutations in the TSHR have been reported to be involved in the development of hyperthyroidism (Duprez, L. et al., *Nat. Genet.* 7: 396-401, 1994; Biebermann, H. et al., *J. Clin. Endocrinol. Metab.* 86: 4429-4433, 2001; Karges, B. et al., *J. Endocrinol.* 186: 377-385, 2005). Activating mutations of both TSHR and Gsα have also been found in goitre and thyroid adenomas (Arturi, F. et al., *Exp. Clin. Endocrinol. Diabetes* 106: 234-236, 1998). The increased cAMP activity in thyroid adenomas, as a result of the activating TSHR or Gsα mutations, has been reported to produce a protective adaptive increase in PDE4 activity to counteract abnormal rise in cAMP levels and signal transduction (Persani, L. et al., *J. Clin. Endocrinol. Metab.* 85: 2872-2878, 2000).

The most common cause of hyperthyroidism is Graves' disease, an autoimmune disorder in which antibodies mimic TSH action at the TSHR, leading to excessive cAMP activity in thyroid follicle cells and consequently a state of hyperthyroidism.

PDE4 long form activators of the present invention are therefore expected to be effective in the treatment, prevention or partial control of hyperthyroidism. In one embodiment, the hyperthyroidism is associated with Graves' disease.

Jansens's Metaphyseal Chondrodysplasia and Hyperparathyroidism

Jansens's Metaphyseal Chondrodysplasia (JMC) is a very rare disease resulting from gain-of-function mutations of the parathyroid hormone (PTH) receptor 1 (PTHR1) (Thompson, M. D. et al., *Methods Mol. Biol.* 448: 109-137, 2008). The constitutive activation of the PTHR1 which couples to adenylyl cyclase as effector is associated with excessive cAMP signalling primarily in bone and kidney, leading to dysregulation of ion homeostasis characterised by hypercalcemia and hypophosphatemia (Calvi, L. M. and Schipani, E. *J. Endocrinol. Invest.* 23: 545-554, 2000) and developmental (e.g. short stature) and physical (e.g. protruding eyes) abnormalities.

Primary hyperparathyroidism results from excessive release of PTH from the parathyroid gland due to tissue enlargement or non-cancerous adenoma. The resulting excessive stimulation of the PTHR1 receptor causes disruption of plasma ion homeostasis with patients showing hypercalcemia and hypophosphatemia. PDE4 long form activators of the present invention are therefore expected to be effective in the treatment, prevention or partial control of JMC and hyperparathyroidism.

Familial Male Precocious Puberty (Testotoxicosis)

Familial male-limited precocious puberty (FMPP), also known as familial sexual precocity or gonadotropin-independent testotoxicosis, is a disorder in which boys generally develop signs of precocious puberty in early childhood.

The spinal length in boys may be short due to a rapid advance in epiphyseal maturation. FMPP is an autosomal dominant condition with constitutively activating mutations in the luteinizing hormone (LH) receptor, which leads to increased cAMP production, associated with Leydig cell hyperplasia and low sperm cell count (Latronico, A. C. et al., *J Clin. Endocrinol. Metab.* 80: 2490-2494, 1995; Kosugi, S. et al., *Hum. Mol. Genet.* 4: 183-188, 1995). PDE4 long form activators of the present invention are therefore expected to be effective in the treatment, prevention or partial control of FMPP.

Pituitary Adenomas and Cushing's Disease

Non-cancerous tumours of the pituitary gland are collectively referred to as pituitary adenomas and can lead to hypersecretion of adenohypophyseal hormones (e.g. growth hormone, thyroid stimulating hormone, luteinizing hormone, follicle stimulating hormone and adrenocorticotrophic hormone), which exert their action through GPCRs coupled to Gs and cAMP generation. Thus pituitary adenomas can lead to a state of enhanced cAMP mediated signalling in a variety of endocrine tissues which can precipitate a number of hormonal disorders such as acromegly (mainly due to excess growth hormone secretion), Cushing's disease (due to overproduction of adrenocorticotrophic hormone (ACTH) and the subsequent hypercortisolemia) and/or general hyperpituitarism (associated with excess release of multiple anterior pituitary hormones). Current treatment options for pituitary adenomas include treatment with dopamine receptor agonists, which reduce tumour size and lower pituitary hormonal output through a mechanism involving lowering of intracellular cAMP levels. PDE4 long form activators of the present invention may also be expected to attenuate the pathological effects of pituitary hormones in their target tissues, such as the adrenal glands.

In Cushing's disease, pituitary adenoma related overproduction of ACTH can lead to hypercortisolemia through an overactivation of melanocortin 2 receptor (MC2) and subsequent cAMP mediated stimulation of steroidogenesis and release of cortisol from the adrenal cortex (Tritos, N. A. and Biller, B. M. *Discov. Med.* 13: 171-179, 2012). PDE4 long form activators of the present invention are therefore expected to be effective in the treatment, prevention or partial control of Cushing's disease.

Polycystic kidney disease

Polycystic kidney disease (PKD) is a genetic disorder of the kidneys characterised by development of pathological cysts, which damage renal structure and compromise kidney function (Takiar, V. and Caplan, M. J. *Biochim. Biophys. Acta.* 1812: 1337-1343, 2011; Masoumi, A. et al., *Drugs* 67: 2495-2510, 2007). There are two types of PKD: autosomal dominant polycystic kidney disease (ADPKD) and autosomal recessive polycystic kidney disease (ARPKD). ADPKD affects between 0.1% and 0.2% of the population worldwide and is characterized by progressive cyst development and enlarged kidneys. Approximately 50% of people with this disease will develop end stage kidney disease, usually between 40 and 70 years of age and require dialysis or kidney transplantation. ARPKD affects around 1:20,000 live births and is typically identified in the first few weeks after birth. Pulmonary hypoplasia results in a 30-50% death rate in neonates with ARPKD.

Defects in two genes are thought to be responsible for ADPKD. In around 85% of patients, development of ADPKD can be linked to mutations in the gene PKD1, encoding polycystin-1 (PC-1); in around 15% of patients mutations in PKD2, encoding polycystin-2 (PC-2) are implicated. Cyclic AMP has been identified as an important stimulus for proliferation and cyst expansion in polycystic kidney cells but not in normal human kidney cells (Yamaguchi, T. et al., *Kidney Int.* 57: 1460-1471, 2000). A considerable body of evidence has now developed to implicate cAMP as an important facilitator of renal cystogenesis (Masoumi, A. et al., *Drugs* 67: 2495-2510, 2007; Wallace, D. P. *Biochim. Biophys. Acta.* 1812: 1291-1300, 2011). Consistent with the role of cAMP in cyst formation, agents that lower cAMP levels (e.g. vasopressin V2 receptor antagonists and the somatostatin receptor agonist octreotide) showed efficacy in rodent models of PKD (Torres, V. E. et al., *Nat. Med.* 10: 363-364, 2004; Gattone, V. H. $2^{nd}$ et al., *Nat. Med.* 9: 1323-1326, 2003; Belibi, F. A. and Edelstein, C. L. *Expert Opin. Investig. Drugs.* 19: 315-328, 2010). In zebrafish embryos, depletion of a cAMP-hydrolysing PDE enzyme subtype, PDE1A, resulted in development of a cystic phenotype, while PDE1A over-expression partially rescued cystic phenotypes resulting from PC2 depletion (Sussman, C. R., Ward, C. J., Leightner, A. C., Smith, J. L., Agarwal, R., Harris, P. C., Torres, V. E. *J. Am. Soc. Nephrol.* 25: 2222-2230, 2014). Phosphodiesterase activation has been suggested as a therapeutic strategy for PKD treatment (Sun, Y., Zhou, H. and Yang, B-X. *Acta Pharmacologica Sinica* 32: 805-816, 2011).

PDE4 long form activators of the present invention are therefore expected to be effective in the treatment, prevention or partial control of polycystic kidney disease.

Figure 7:
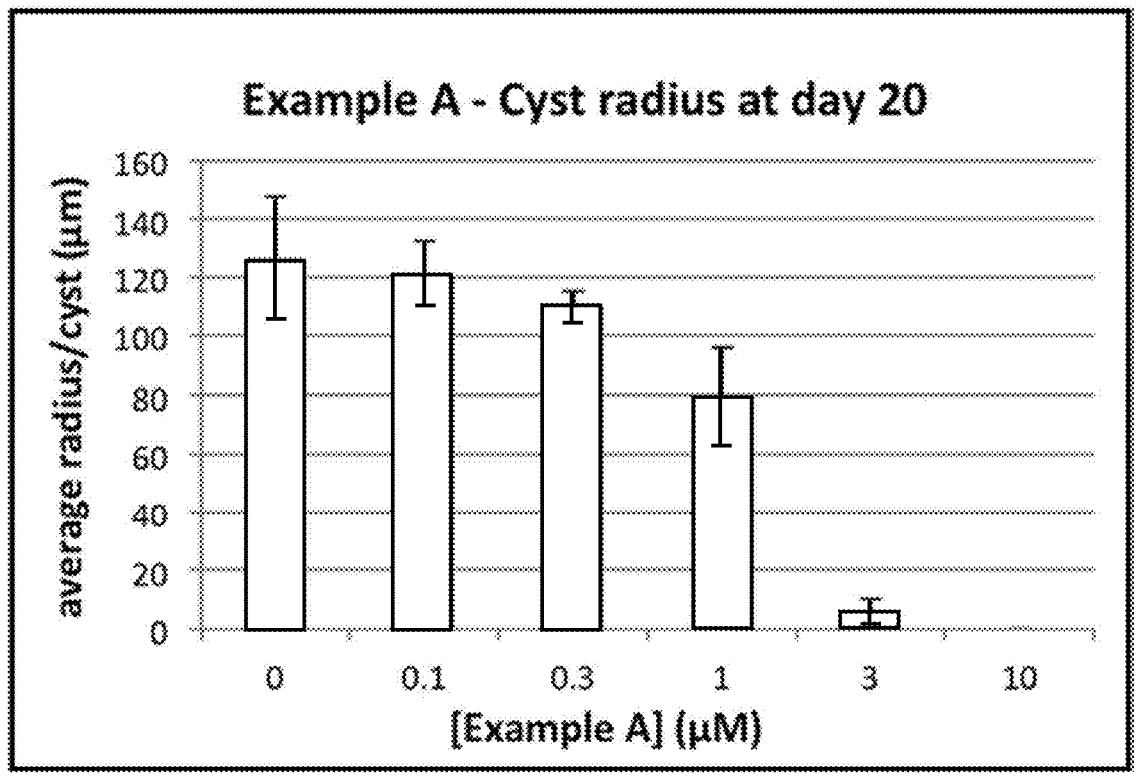
FIG. 7 shows inhibition of in vitro cyst formation in MDCK cells treated with a PDE4 long form activator—Example A—using the method described in Experiment 3, with addition of the specified concentrations of the test compounds every 2 days from day 0 to day 20.
Figure 7:
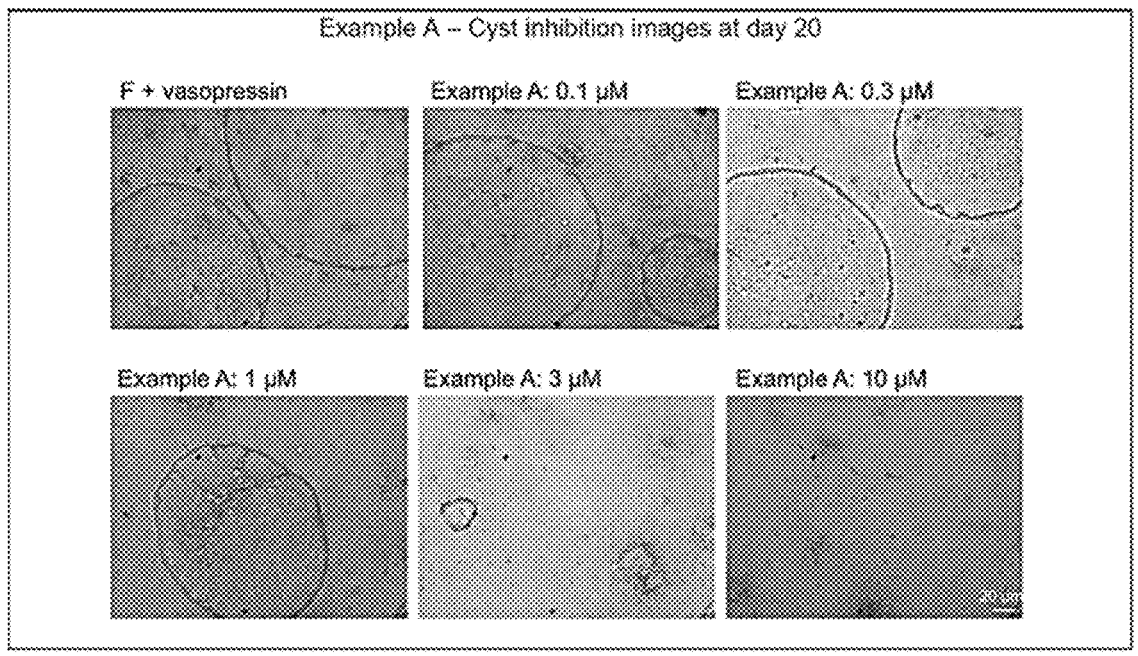
Figure 8:
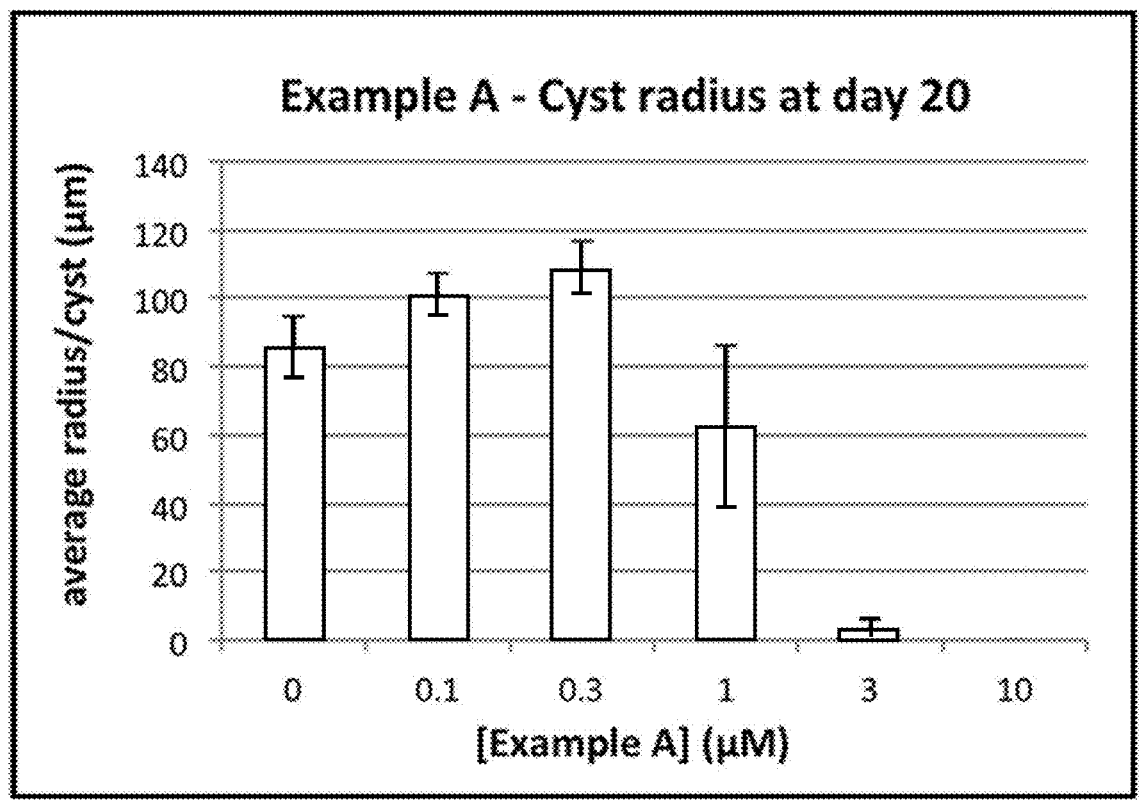
FIG. 8 shows a reversal of in vitro cyst formation in MDCK cells treated with a PDE4 long form activator—Example A—using the method described in Experiment 4, with addition of the specified concentrations of the test compounds every 2 days from day 10 to day 20.
Figure 8:
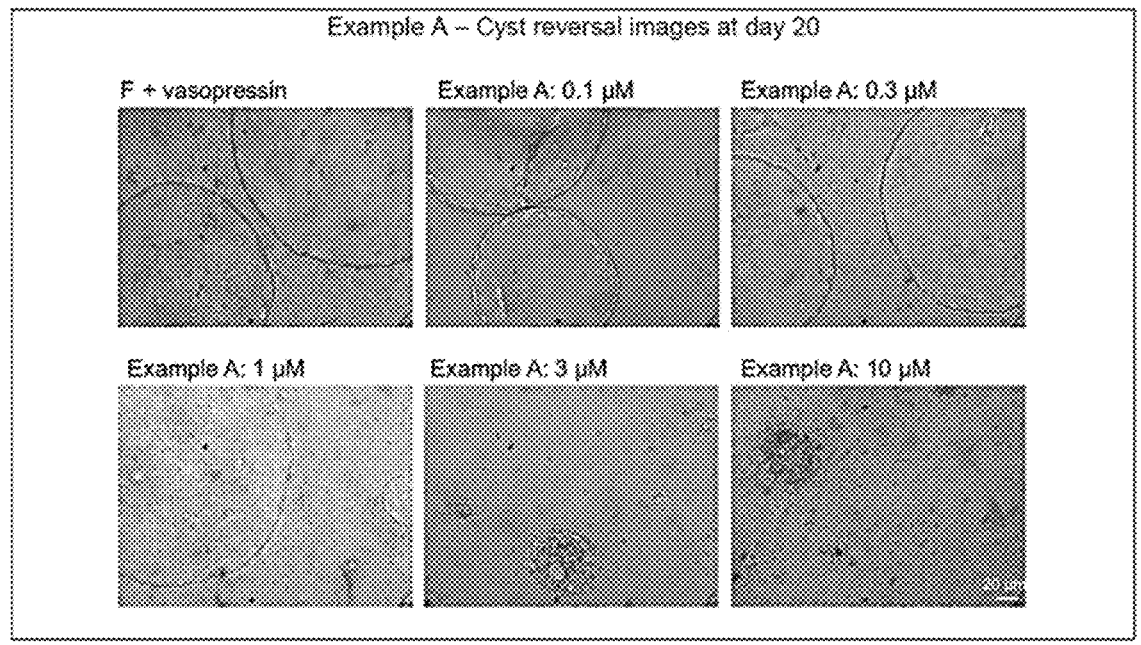

The Examples, in particular FIGS. 7 and 8, show the inhibition and reversal of in vitro cyst formation in dog MOCK cells treated with a PDE4 long form activator—Example A—using the methods described in Experiment 3, with addition of the specified concentrations of the test compounds every 2 days from day 0 to day 20, and Experiment 4, with addition of the specified concentrations of the test compounds every 2 days from day 10 to day 20.

Figure 13A:
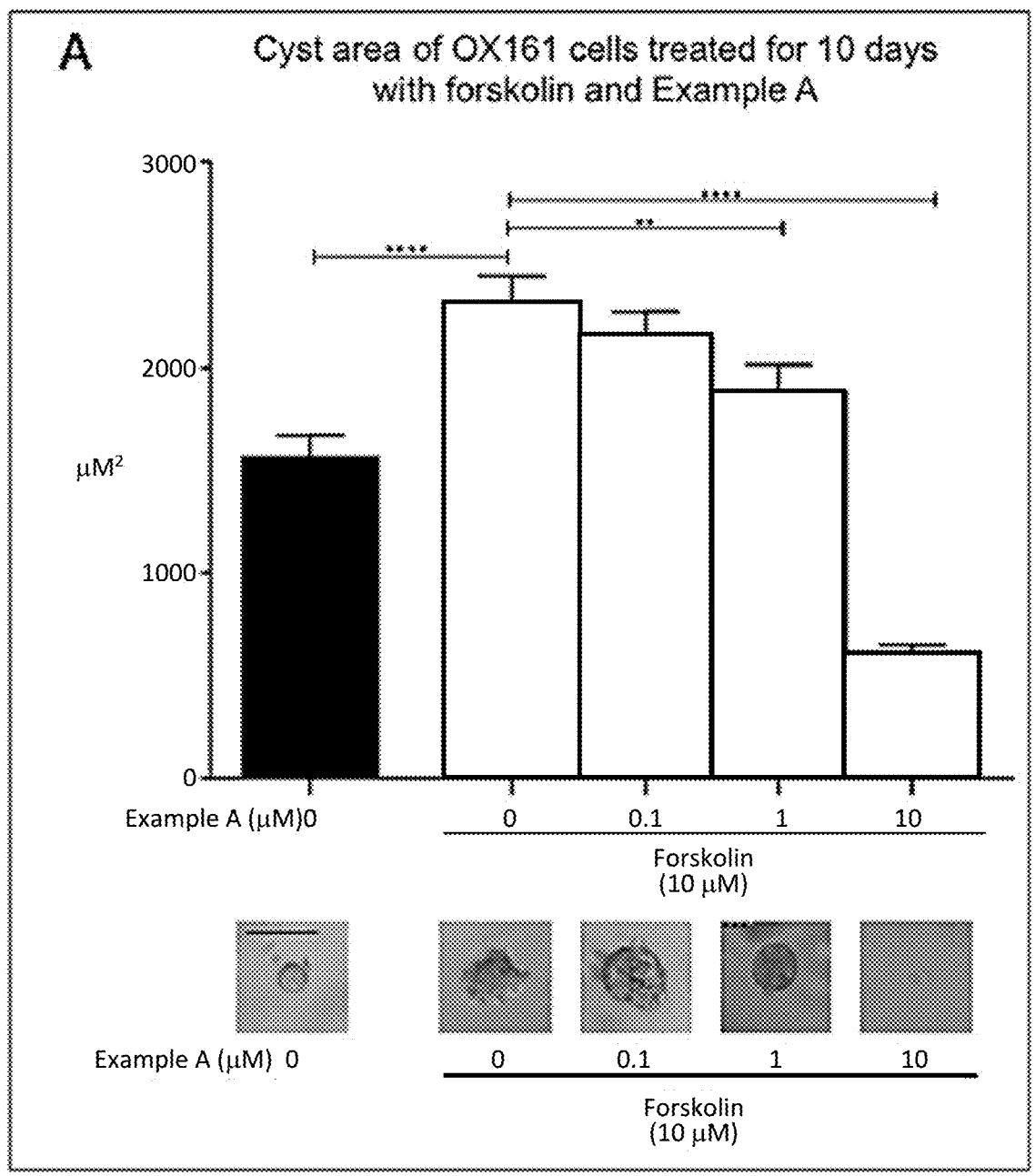
FIG. 13 shows (A) concentration dependent inhibition and (B) concentration dependent reversal of in vitro cyst formation in a human patient-derived conditionally immortalised OX161 cell line by Example A.
Figure 13B:
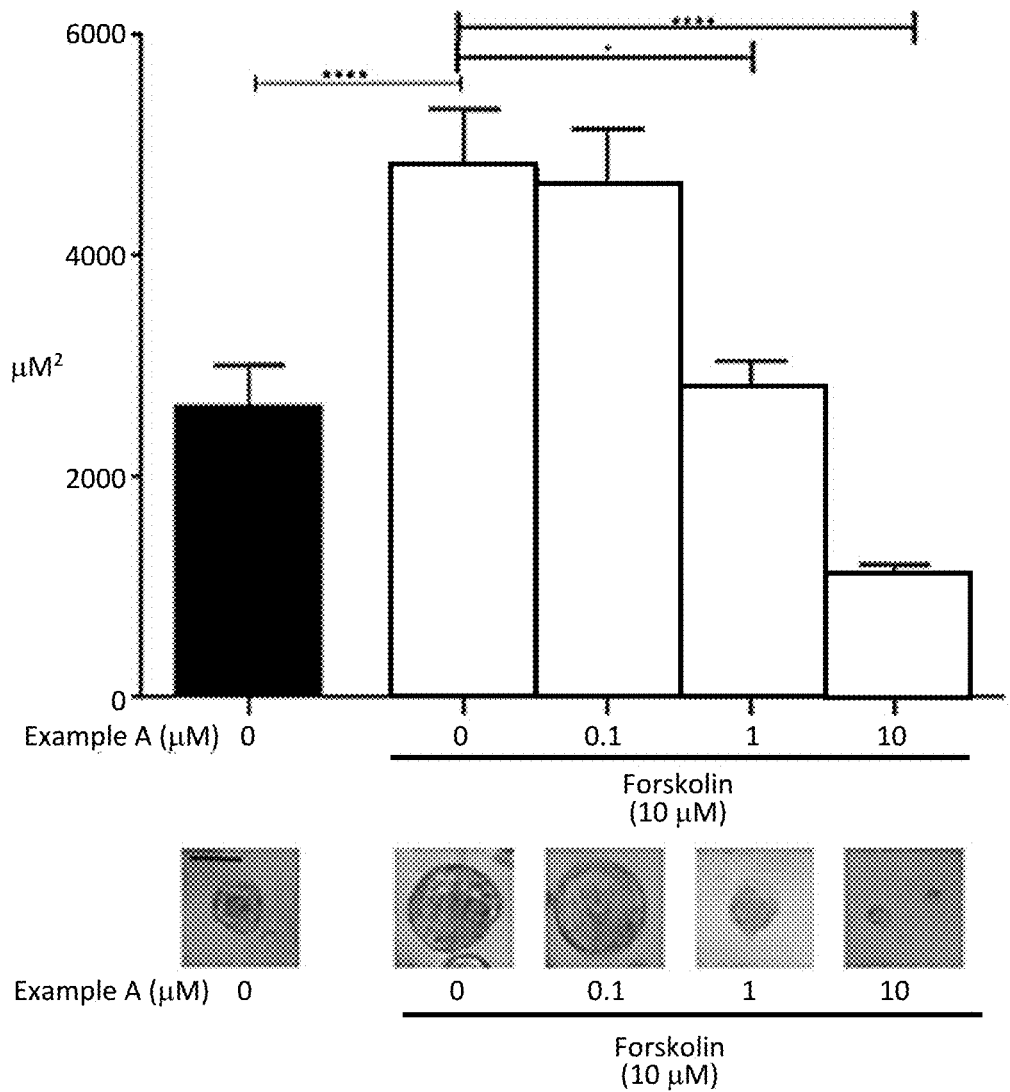

The Examples, in particular FIG. 13, show the inhibition and reversal of in vitro cyst formation in human OX161 cells treated with a PDE4 long form activator—Example A—using the methods described in Experiment 9, with addition of the specified concentrations of the test compound every 2 days from day 0 to day. 10, and Experiment 10, with addition of the specified concentrations of the test compound every 2 days from day 10 to day 20.

This provides experimental confirmation of the rationale that compounds of the invention are able to treat diseases and disorders mediated by cAMP.

Polycystic Liver Disease

Polycystic liver disease (PLD) is a rare inherited condition associated with hepatic cystogenesis (usually defined when number of cysts exceeds 20), which often occurs in association with ADPKD (Strazzabosco, M. and Somlo, S. *Gastroenterology* 140: 1855-1859, 2011; Gevers, T. J. and Drenth, J. P. *Curr. Opin. Gastroenterol.* 27: 294-300, 2010). PLD may have a different genetic pathology when compared to ADPKD, driven by mutated proteins associated with the endoplasmic reticulum and the cilium. Increased cholangiocyte proliferation, neovascularisation and elevated fluid secretion act to drive liver cyst formation through dysregulation of multiple signal transduction pathways, including cAMP-mediated signalling. Elevation of hepatic cAMP levels stimulates cAMP-dependent chloride and fluid secretion in biliary epithelial cells and increases cholangiocyte proliferation (Janssen, M. J. et al., *J. Hepatol.* 52: 432-440, 2010). Somatostatin, which acts through a Gi-coupled mechanism to lower cAMP levels, reduced cholangiocyte proliferation and fluid secretion (Gong, A. Y. et al., *Am. J. Physiol. Cell. Physiol.* 284: C1205-1214, 2003). Furthermore, the synthetic somatostatin analogue, octreotide, showed efficacy in an animal model of PLD through a mechanism involving reduction in cAMP signalling (Masyuk, T. V. et al., *Gastroenterology* 132: 1104-1116, 2007). PDE4 long form activators of the present invention may therefore be effective in the treatment, prevention or partial control of polycystic liver disease due at least in part to cAMP.

Maturity Onset Diabetes of Young Type 5 (MODY5)

MODY5 is a form of non-insulin-dependent diabetes mellitus associated with renal cysts. It is an autosomal dominant disorder caused by mutations in the gene encoding hepatocyte nuclear factor-1β (HNF-1β). The predominant clinical feature of patients affected by MODY5 is renal dysfunction, frequently diagnosed before the onset of diabetes. In some patients, HNF-1β mutations can result in additional phenotypic features, such as pancreatic atrophy, abnormal liver function and genital tract abnormalities. Studies in mice suggest that the mechanism responsible for renal cyst formation, associated with mutations of HNF-1β, involves a severe defect of the transcriptional activation of PKD2, in addition to effects on uromodulin (UMOD) and PKD1 genes. Down-regulation of PKD1 and PKD2 is associated with cAMP-driven formation of renal cysts (Mancusi, S. et al., *J. Nephrol.* 26: 207-12, 2013). HNF-1β also binds to the PDE4C promoter and regulates the expression of PDE4C (Ma et al., *PNAS* 104: 20386, 2007).

PDE4 long form activators of the present invention are therefore expected to be effective in the treatment, prevention or partial control of the symptoms of MODY5.

Cardiac Hypertrophy, Heart Failure and Arrhythmia

Localized regulation and integration of cAMP signalling are important for proper cardiac function and perturbation of this signalling can lead to heart failure. Upon chronic β-adrenergic receptor stimulation, cardiomyocyte hypertrophy is induced via elevated cAMP and activation of its downstream effectors, including PKA and Epac (Wang, L. et al., *Cell. Signal.* 27: 908-922, 2015 and references therein). Cardiomyocyte hypertrophy increases the risk of heart failure and arrhythmia.

PDE4 long form activators of the present invention may therefore be effective in the treatment, prevention or partial control of cardiac hypertrophy, heart failure and/or arrhythmia.

Diseases Associated with Increased cAMP-Mediated Signalling

Disorders Associated with Activating Mutations of the Alpha Subunit of the G Protein (GNAS1)

The G-protein Gs acts as a transducer for GPCRs that stimulate adenylyl cyclase activity and exert their biological effects by increasing intracellular cAMP levels. Gs is a heterotrimeric protein composed of α, β and γ subunits. Activating mutations in the gene, GNAS1, for the α-subunit have been identified which lead to exaggerated abnormal cAMP signalling in a variety of tissues and give rise to a range of disorders.

McCune-Albright Syndrome

McCune-Albright syndrome (MAS) is a rare genetic disorder typically characterised by three dominating features of precocious puberty, fibrous dysplasia of bone and café au lait lesions. The underlying molecular pathology for MAS involves an activating mutation of the GNAS1 gene (Diaz, A. Danon, M. and Crawford, J. J. *Pediatr. Endocrinol. Metab.* 20: 853-880, 2007). PDE4 long form activators of the present invention would therefore be expected to be effective in the treatment, prevention or partial control of disorders associated with activating mutations of GNAS1, including McCune-Albright syndrome.

Amelioration of Toxin-Induced Increases in Adenylyl Cyclase Activity in Infectious Diseases Adenylyl cyclase, the enzyme responsible for production of cAMP, is a key biological target thought to be involved in mediating the effects of many bacterial toxins (Ahuja et al., *Critical Reviews in Microbiology*, 30: 187-196, 2004). These toxins produce their effects by raising cAMP levels through enhancement of host immune cell and/or pathogen related adenylyl cyclase activity. PDE4 long form activators of the present invention, by reducing cAMP levels, would therefore be expected to be of utility in the treatment or partial control of symptoms of infectious diseases that are associated with elevated cAMP activity. The following are some examples of such infectious diseases:

Cholera

*Vibrio cholerae* produces cholera toxin, which through adenosine disphosphate ribosylation of the a subunit of Gs leads to host cell adenylyl cyclase activation and cAMP production. Diarrhoea caused by cholera toxin is believed to be a result of excessive cAMP accumulation in the cells of the gastrointestinal tract.

Whooping Cough

*Bordetella pertussis* is the pathogen responsible for the childhood disease whooping cough. *Bordetella pertussis* toxin stimulates adenosine disphosphate ribosylation of the α subunit of Gi and indirectly augments cAMP levels in target cells. The bacterium also secretes an invasive adenylyl cyclase, which produces toxic cAMP levels and impairs host immune defence.

Anthrax

Anthrax is caused by *Bacillus anthracia* and whilst it is primarily an animal disease it can be transmitted to humans through contact. Anthrax infections are associated with widespread oedema, the development of which is thought to be driven by oedema toxin. The latter is an adenylyl cyclase and is activated by host calmodulin to produce abnormally high levels of cAMP that have a toxic effect on host immune cells.

Tuberculosis

*Mycobactrium tuberculosis* expresses a large and diverse range of adenylyl cyclases, which may play a role in virulence and generation of disease pathology. One adenylyl cyclase subtype, RV0386, has been demonstrated to enter host macrophages and elevate intracellular CAMP to cause toxicity (Agarwal et al., *Nature*, 460: 98-102, 2009).

PDE4 long form activators of the present invention may therefore be effective in the treatment, prevention or partial control of infectious diseases such as cholera, whooping cough, anthrax and tuberculosis.

Diseases Dependent Upon Activation of PKA by Elevated cAMP

In eukaryotes, cAMP activates protein kinase A (PKA), which is also known as cAMP-dependent protein kinase. PKA is normally inactive as a tetrameric holoenzyme, consisting of two catalytic and two regulatory units, with the regulatory units blocking the catalytic centres of the catalytic units. cAMP binds to specific locations on the regulatory units of PKA and causes dissociation between the regulatory and catalytic units, thus activating the catalytic units. The active catalytic units catalyse the transfer of phosphate from ATP to specific residues of protein substrates, which may modulate the function of those protein substrates.

PDE4 long form activation reduces cAMP levels and cAMP mediated activation of PKA. PDE4 long form activators of the present invention would therefore be expected to be of utility in the treatment or partial control of disorders where inhibitors of PKA show evidence of therapeutic effects.

Disorders that are dependent upon activation of PKA by cAMP may be identified by their response to PKA inhibitors such as Rp-8-Br-cAMPS. Rp-8-Br-cAMPS is an analogue of cAMP that occupies the cAMP binding sites of PKA, preventing its dissociation and activation.

HIV Infection and AIDS

T cells from HIV-infected patients have increased levels of cAMP and are more sensitive to inhibition by Rp-8-Br-cAMPS than are normal T cells. Excessive activation of PKA by cAMP has been associated with the progressive T cell dysfunction in HIV infection (Aandahl, E. M. et al., *FASEB J.* 12: 855-862, 1998). Furthermore, in vivo administration of Rp-8-Br-cAMPS has been shown to restore T cell responses in retrovirus-infected mice (Nayjib, B. et al., *The Open Immunology Journal*, 1: 20-24, 2008). PDE4 long form activators of the present invention are therefore expected to be of utility in the treatment, prevention or partial control of HIV infection and AIDS.

Common Variable Immunodeficiency (CVID)

In vitro administration of Rp-8-Br-cAMPS has been shown to correct impaired secretion of the cytokine IL-10 by T cells from patients with Common Variable Immunodeficiency (CVID) (Holm, A. M. et al., *J. Immunol.* 170: 5772-5777, 2003). PDE4 long form activators of the present invention are therefore expected to be of utility in the treatment, prevention or partial control of CVID.

Diseases Dependent Upon Activation of Either or Both of Epac1 and Epac2 by Elevated cAMP In addition to PKA, cAMP activates another intracellular receptor, known as exchange protein directly activated by CAMP (Epac). There are two isoforms of Epac, Epac1 and Epac2, both consisting of a regulatory region that binds cAMP and a catalytic region that promotes the exchange of GDP for GTP on the small G proteins, Rap1 and Rap2 of the Ras family. In addition, Epac proteins exert their functions through interactions with a number of other cellular partners at specific cellular loci. Pathophysiological changes in Epac signalling have been associated with a wide range of diseases (Breckler, M. et al., *Cell. Signal.* 23: 1257-1266, 2011).

Relevant disorders that are dependent upon activation of Epac proteins by cAMP may be identified by their response to Epac inhibitors, such as ESI-09, a novel non-cyclic nucleotide Epac1 and Epac2 antagonist that is capable of specifically blocking intracellular Epac-mediated Rap1 activation and Akt phosphorylation, as well as Epac-mediated insulin secretion in pancreatic beta cells (Almahariq, M. et al., *Mol. Pharmacol.* 83: 122-128, 2013).

Melanoma

Epac1 has been implicated in promoting migration and metastasis in melanoma (Baljinnyam, E. et al., *Pigment Cell Melanoma Res.* 24: 680-687, 2011 and references cited therein).

PDE4 long form activators of the present invention are therefore expected to be of utility in the treatment, prevention or partial control of melanoma.

Pancreatic Cancer

It has recently been shown that Epac1 is markedly elevated in human pancreatic cancer cells as compared with normal pancreas or surrounding tissue (Lorenz, R. et al., *Pancreas* 37: 102-103, 2008).

Pancreatic cancer is often resistant to treatments that are usually effective for other types of cancer. Using the Epac inhibitor ESI-09, a functional role of Epac1 overexpression in pancreatic cancer cell migration and invasion was demonstrated (Almahariq, M. et al., *Mol. Pharmacol.* 83: 122-128, 2013). These findings are consistent with results based on RNAi silencing techniques and suggest that inhibition of Epac1 signalling could be an effective therapeutic strategy for pancreatic cancer.

PDE4 long form activators of the present invention would therefore be expected to be of utility in the treatment, prevention or partial control of pancreatic cancer.

Diseases Dependent Upon Modulation of cAMP-Gated Ion Channels by Elevated cAMP

In addition to activation of PKA and Epac, another effector pathway for elevated cAMP is the activation of cAMP-gated ion channels. PDE4 long form activators of the present invention would therefore be expected to be of utility in the treatment of disorders where inhibitors of CAMP-gated ion channels show evidence of therapeutic effects.

Diseases Associated with Increased Activity of cAMP Response Element Binding Protein The cAMP response element binding protein (CREB) is an important transcription factor involved in the regulation of a variety of cellular functions such as cell proliferation, differentiation, survival, and apoptosis (Cho et al., *Crit Rev Oncog,* 16: 37-46, 2011). CREB activity is regulated by kinase dependant phosphorylation through a range of extracellular signals, such as stress, growth factors and neurotransmitters. Phosphorylation leads to dimerisation of CREB, and together with other co-activator partner proteins, enables it to bind to promoter regions of target genes containing the cAMP response element (CRE sites) and initiate transcriptional activity. The cAMP pathway (e.g. through cAMP-dependant protein kinase mediated phosphorylation) is an important positive modulator of CREB mediated biological activity. PDE4 long form activators of the present invention are therefore expected to be of utility in the treatment, prevention or partial control of disorders associated with elevated CREB activity.

Leukaemia

Bone marrow cells from acute lymphoid and myeloid leukaemia patients have been reported to overexpress CREB protein and mRNA (Crans-Vargas et al., *Blood,* 99: 2617-9, 2002; Cho et al., *Crit Rev Oncog,* 16: 37-46, 2011). Furthermore, the increased CREB level correlates with poor clinical response in subjects with acute myeloid leukaemia (Grans-Vargas et al., *Blood,* 99: 2617-9, 2002; Shankar et al., *Cancer Cell,* 7:351-62, 2005). Upregulation of CREB is associated with stimulation of human leukaemia cell growth whilst downregulation inhibits myeloid cell proliferation and survival. PDE4 long form activators of the present invention would be expected to reduce CREB activity and function through attenuation of cAMP mediated stimulation of CREB and therefore expected to have utility in the treatment, prevention or partial control of acute lymphoid and myeloid leukaemia.

Prostate Cancer

Abnormal excessive androgen activity is an important driver in the development of prostate cancer as it stimulates the development of intraepithelial neoplasias (Merkle et al., *Cellular Signalling,* 23: 507-515, 2011). This is strongly supported by the use of androgen ablation approaches, involving chemical or surgical castration, in the treatment of prostate cancer. Cyclic AMP elevating agents such as forskolin can enhance androgen receptor activity through multiple intracellular mechanisms including androgen receptor activation through phosphorylation and/or interaction with CREB. Epac1 activation has also been implicated in promoting cellular proliferation in prostate cancer (Misra, U. K. and Pizzo, S. V. *J. Cell. Biochem.* 108: 998-1011, 2009; Misra, U. K. and Pizzo, S. V. *J. Cell. Biochem.* 113: 1488-1500, 2012). PDE4 long form activators of the present invention are therefore expected to have utility in the treatment, prevention or partial control of prostate cancer.

The Examples demonstrate that compounds of the invention are able to inhibit the proliferation of prostate cancer cells. This provides experimental confirmation of the rationale that compounds of the invention are able to treat diseases and disorders mediated by cAMP.

Diseases Associated with Reduced Activity of cAMP-Hydrolysing PDE Enzymes

Loss-of-function mutations in gene(s) for cAMP-hydrolysing PDE isoforms other than PDE4, such as PDE8 and PDE11, have been detected in a number of diseases (Vezzosi, D. and Bertherat, J., *Eur. J. Endocrinol.* 165: 177-188, 2011; Levy, I. et al., *Curr. Opin. Pharmacol.* 11: 689-697, 2011; Azevedo, M. F. and Stratakis, C. A. *Endocr. Pract.* 17 Suppl 3: 2-7, 2011). These mutations can lead to abnormally high cAMP levels and/or duration of CAMP action with pathological consequences as detailed below. PDE4 long form activators of the present invention are therefore expected to be of utility in the treatment, prevention or partial control of these diseases, such as adrenocortical tumours, testicular cancer, PPNAD and Carney Complex.

Adrenocortical Tumours

Adrenocortical tumours associated with an inactivating point mutation in the gene encoding PDE11A4 have decreased expression of PDE11A4 and increased cAMP levels (Horvath, A. et al., *Nat Genet.* 38: 794-800, 2006; Horvath, A. et al., *Cancer Res.* 66: 11571-11575, 2006; Libé, R., et al., *Clin. Cancer Res.* 14: 4016-4024, 2008).

Testicular Cancer

Mutations that reduce PDE11A activity and increase CAMP levels have been observed in some forms of testicular cancer (Horvath. A. et al., *Cancer Res.* 69: 5301-5306, 2009).

Primary Pigmented Nodular Adrenocortical Diseases (PP-NAD)

Mutations in the PDE8B gene have also been identified as a predisposing factor for PPNAD and the mutant protein shows reduced ability to degrade cAMP (Horvath, A., Mericq, V. and Stratakis, C. A. *N. Engl. J. Med.* 358: 750-752, 2008; Horvath, A. et al., *Eur. J. Hum. Genet.* 16: 1245-1253, 2008).

Carney Complex

In Carney Complex (CNC) caused by PRKAR1A mutations, some patients also have defects in PDE11A that may exert a synergistic effect to enhance abnormal activation of the cAMP signal transduction pathway, leading to adrenal and testicular cancer (Libé, R. et al., *J. Clin. Endocrinol. Metab.* 96: E208-214, 2011).

Treatment and Posology

By "treatment" herein is meant the treatment by therapy, whether of a human or a non-human animal (e.g., in veterinary applications) typically a non-human mammal, in which some desired therapeutic effect on the condition is achieved; for example, the inhibition of the progress of the disorder, including a reduction in the rate of progress, a halt in the rate of progress, amelioration of the disorder or cure of the condition. Treatment as a prophylactic measure is also included. References herein to prevention or prophylaxis herein do not indicate or require complete prevention of a condition; its manifestation may instead be reduced or delayed via prophylaxis or prevention according to the present invention.

By a "therapeutically effective amount" herein is meant an amount of the one or more compounds of the invention or a pharmaceutical formulation comprising such one or more compounds, which is effective for producing such a therapeutic effect, commensurate with a reasonable benefit/risk ratio.

It will be appreciated that appropriate dosages of the compounds of the invention may vary from patient to patient. Determining the optimal dosage will generally involve the balancing of the level of therapeutic benefit against any risk or, deleterious side effects of the treatments of the present invention. The selected dosage level will depend on a variety of factors including the activity of the particular compound, the route of administration, the time of administration, the rate of excretion of the compound, the duration of the treatment, other drugs, compounds or materials used in combination and the age, sex, weight, condition, general health and prior medical history of the patient.

The amount of compound(s) and route of administration will ultimately be at the discretion of the physician, although generally the dosage will be to achieve local concentrations at the site of action so as to achieve the desired effect. Administration in vivo can be effected in one dose, continuously or intermittently throughout the course of treatment. Methods of determining the most effective means and dosage of administration are well known to a person skilled in the art and will vary with the formulation used for therapy, the purpose of the therapy, the target cell being treated, and the subject being treated. Single or multiple administrations can be carried out with the dose level and pattern being selected by the treating physician.

In general, a suitable dose of the one or more compounds of the invention may be in the range of about 0.001 to 50 mg/kg body weight of the subject per day, preferably in a dosage of 0.01-25 mg per kg body weight per day, e.g., 0.01, 0.05, 0.10, 0.25, 0.50, 1.0, 2.5, 10 or 25 mg/kg per day. Where the compound(s) is a salt, solvate, prodrug or the like, the amount administered may be calculated on the basis of the parent compound and so the actual weight to be used may be increased proportionately.

Combination Therapies

The compounds of the invention may also find application in mimicking or enhancing the effects of drugs known to produce their therapeutic effect through lowering of intracellular cAMP levels.

A number of therapeutically beneficial drugs have a primary mode of action involving lowering intracellular cAMP levels and/or cAMP-mediated activity, as summarised below. Since PDE4 long form activators of the present invention will also act to lower cAMP levels it is expected that these agents will mimic and/or augment the pharmacological properties and therapeutic utility of drugs operating through a down-regulation of cAMP-mediated signalling. In certain embodiments, a compound of the invention is therefore provided as part of a combination therapy with another agent that lowers intracellular cAMP levels and/or cAMP-mediated activity. The combination therapy may be administered simultaneously, contemporaneously, sequentially or separately. In one embodiment, the compound of the invention and the separate cAMP lowering agent are provided in a single composition, as described in more detail below. The combination therapy may comprise a compound of the invention and one or more of:

(i) a presynaptic α-2 adrenergic receptor agonist, optionally clonidine, dexmedetomidine, or guanfacine;

(ii) a β-1 Adrenergic receptor antagonist ("beta-blocker"), optionally Atenolol, Metoprolol, Bisoprolol, Acebutolol, or Betaxolol.

Combination with α-2 Adrenergic Receptor Agonist

α-2 Adrenergic receptor stimulation is known to reduce cAMP levels through a $G_i$ protein-mediated inhibition of adenylyl cyclase activity in a broad range of tissues. In noradrenergic neurones in the brain and peripheral sympathetic nervous system, presynaptic α-2 adrenergic receptor activation inhibits noradrenaline release and noradrenergic activity. Drugs (e.g. clonidine, dexmedetomidine, guanfacine) that act as agonists at these receptors are effective in the treatment of a variety of clinical conditions. Clonidine, the prototypic agent, has shown therapeutic utility in the treatment of hypertension, neuropathic pain, opioid detoxification, insomnia, ADHD, Tourette syndrome, sleep hyperhidrosis, addiction (narcotic, alcohol and nicotine withdrawal symptoms), migraine, hyperarousal, anxiety and also as a veterinary anaesthetic. Lowering of cAMP levels by PDE4 long form activation may be expected to yield similar effects to drugs acting through α-2 adrenergic receptor stimulation. Furthermore, PDE4 long form activators of the present invention may be expected to potentiate the pharmacodynamic effects of α-2 adrenergic receptor agonists when used in combination.

Combination with β-1 Adrenergic Receptor Antagonist

β-1 Adrenergic receptor antagonists are used in the treatment a range of cardiovascular indications including hypertension, cardiac arrhythmias and cardioprotection following myocardial infarction. Their primary mechanism of action involves reducing the effects of excessive circulating adrenaline and sympathetic activity, mediated by noradrenaline, particularly at cardiac β-1 adrenergic receptors. Endogenous and synthetic β-1 adrenergic receptor agonists stimulate adenylyl cyclase activity through $G_s$ activation and raise intracellular cAMP levels in a variety of tissues such as heart and kidney. Consequently, drugs that block β-1 adrenergic receptor mediated activity exert their pharmacological effects by attenuating the increase in cAMP mediated signalling. Given that PDE4 long form activation will also lower cAMP concentration and transduction in cardiac tissue, PDE4 long form activators of the present invention may be expected to find utility in the treatment or partial control of hypertension, cardiac arrhythmias, congestive heart failure and cardioprotection. Additional non-cardiovascular therapeutic utility may be expected in disorders such as post-traumatic stress related disorder, anxiety, essential tremor and glaucoma, which also respond to β-1 adrenergic antagonist treatment. Furthermore, PDE4 long form activators of the present invention may be expected to potentiate the pharmacodynamic effects of β-1 adrenergic receptor antagonists when used in combination, Methods of Treatment In a further aspect, the present invention provides a small molecule activator of a PDE4 long form of Formula 1 or Formula 2 for use in a method for the treatment or prevention of a disease or disorder in a patient in need of such therapy. The disease or disorder may be any disease of disorder described herein, including: a disease associated with increased cAMP production and signalling (such as hyperthyroidism, Jansens's metaphyseal chondrodysplasia, hyperparathyroidism, familial male-limited precocious puberty, pituitary adenomas, Cushing's disease, polycystic kidney disease, polycystic liver disease, MODY5 and cardiac hypertrophy); diseases known to be associated with increased cAMP-mediated signalling, including disorders associated with activating mutations of the alpha subunit of the G protein (GNAS1) (such as McCune-Albright syndrome); amelioration of toxin-induced increases in adenylyl cyclase activity in infectious diseases (such as cholera, whooping cough, anthrax, and tuberculosis); treatment of diseases known to be dependent upon activation of PKA by elevated cAMP (such as HIV infection and AIDS, and Common Variable Immunodeficiency (CVID)); treatment of diseases known to be dependent upon activation of either or both of Epac1 and Epac2 by elevated cAMP (such as melanoma and pancreatic cancer); treatment of diseases dependent upon modulation of cAMP-gated ion channels by elevated cAMP; treatment of diseases known to be associated with increased activity of cAMP response element binding protein (such as leukaemia and prostate cancer); treatment of diseases known to be associated with reduced activity of cAMP-hydrolysing PDE enzymes (such as adrenocortical tumours, testicular cancer, primary pigmented nodular adrenocortical diseases (PPNAD) and Carney Complex); and mimicking or enhancing the effects of drugs known to produce their therapeutic effect through lowering of intracellular cAMP levels.

As used herein, the terms "compound of the invention", "compound of Formula 1", "compound of Formula 2" etc. include pharmaceutically acceptable derivatives thereof and polymorphs, isomers and isotopically labelled variants thereof. Furthermore, these terms include all the sub-embodiments of those compounds disclosed herein.

Pharmaceutically Acceptable Derivatives

The present invention further provides pharmaceutical compositions comprising a compound of the invention, including a pharmaceutically acceptable salt, solvate, ester, hydrate or amide thereof, in admixture with a pharmaceutically acceptable excipient(s), and optionally other therapeutic agents. The term "acceptable" means being compatible with the other ingredients of the composition and not deleterious to the recipient thereof. Compositions include e.g. those suitable for oral, sublingual, subcutaneous, intravenous, epidural, intrathecal, intramuscular, transdermal, intranasal, pulmonary, topical, local, or rectal administration, and the like, typically in unit dosage forms for administration.

The term "pharmaceutically acceptable salt" includes a salt prepared from pharmaceutically acceptable non-toxic acids or bases including inorganic or organic acids and bases. Compounds of the invention which contain basic, e.g. amino, groups are capable of forming pharmaceutically acceptable salts with acids. Examples of pharmaceutically acceptable acid addition salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Compounds of the invention which contain acidic, e.g. carboxyl, groups are capable of forming pharmaceutically acceptable salts with bases. Pharmaceutically acceptable basic salts of the compounds of the invention include, but are not limited to, metal salts such as alkali metal or alkaline earth metal salts (e.g. sodium, potassium, magnesium or calcium salts) and zinc or aluminium salts and salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of the compounds of the invention may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002).

Prodrugs

The invention includes prodrugs of the compounds of Formulae 1 and 2. Prodrugs are derivatives of compounds of Formula 1 or 2 (which may have little or no pharmacological activity themselves), which can, when administered in vivo, be converted into compounds of Formula 1 or 2.

Prodrugs can, for example, be produced by replacing functionalities present in the compounds of Formula 1 or 2 with appropriate moieties which are metabolized in vivo to form a compound of Formula 1 or 2. The design of prodrugs is well-known in the art, as discussed in Bundgaard, *Design* of Prodrugs 1985 (Elsevier), *The Practice of Medicinal Chemistry* 2003, 2$^{nd}$ Ed, 561-585 and Leinweber, *Drug Metab. Res.* 1987, 18: 379.

Examples of prodrugs of compounds of Formula 1 or 2 are amides and, esters of those compounds. For example, where the compound of Formula 1 or 2 contains a carboxylic acid group (—COOH), the hydrogen atom of the carboxylic acid group may be replaced in order to form an ester (e.g. the hydrogen atom may be replaced by $C_{1-6}$alkyl). Where a compound contains an alcohol group (—OH), the hydrogen atom of the alcohol group may be replaced in order to form an ester (e.g. the hydrogen atom may be replaced by —C(O)$C_{1-6}$alkyl.

Solvates

It may be convenient or desirable to prepare, purify, and/or handle a corresponding solvate of the compounds described herein, which may be used in the any one of the uses/methods described. The term solvate is used. herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

Stereoisomers

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of Formula 1 or 2 as well as wholly or partially racemic mixtures of such enantiomers. Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Isotopes

The invention includes pharmaceutically acceptable isotopically-labelled compounds of Formula 1 or 2 wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulphur, such as $^{35}$S. Certain isotopically-labelled compounds of Formula 1 or 2, for example, those incorporating a radioactive isotope, are useful in drug and/or substrate tissue distribution studies. The radioactive isotopes $^3$H and $^{14}$C are particularly useful for this purpose in view of their ease of incorporation and ready means of detection. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula 1 or 2 can generally be prepared by conventional techniques known to those skilled in the art or by processes analogous to those described herein using an appropriate isotopically-labelled reagent in place of the non-labelled reagent previously employed.

Pharmaceutical Compositions

For oral administration, the active ingredient may be presented as discrete units, such as tablets, capsules, powders, granulates, solutions, suspensions, and the like.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one, or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

For administration intranasally or by inhalation, the active ingredient may be presented in the form of a dry powder from a dry powder inhaler or in the form of an aerosol spray of a solution or suspension from a pressurised container, pump, spray, atomiser or nebuliser.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

For parenteral administration, the compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of co-solvents and/or solubility-enhancing agents such as surfactants, micelle structures and cyclodextrins.

Mixed with such pharmaceutically acceptable excipients, e.g. as described in the standard reference, Gennaro, A. R. et al, Remington: The Science and Practice of Pharmacy (21st Edition, Lippincott Williams & Wilkins, 2005, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation or as an aerosol spray, in the form of a solution, suspension, or emulsion.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

In some embodiments, the one or more compounds of the present invention may be used in combination therapies for the treatment of the described conditions i.e., in conjunction with other therapeutic agents. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

In one, embodiment, the invention provides a product comprising a compound of the invention and another therapeutic agent as a combined preparation for simultaneous, separate or sequential use in therapy. In one embodiment, the therapy is the treatment or prevention of disorders where a reduction of second messenger responses mediated by cyclic 3',5'-adenosine monophosphate (cAMP) is required. Products provided as a combined preparation include a composition comprising a compound of the invention and the other therapeutic agent together in the same pharmaceutical composition, or the compound of the invention and the other therapeutic agent in separate form, e.g. in the form of a kit.

In one embodiment, the invention provides a pharmaceutical composition comprising a compound of the invention and another therapeutic agent. Optionally, the pharmaceutical composition may comprise a pharmaceutically acceptable excipient, as described above.

In one embodiment, the invention provides a kit comprising two or more separate pharmaceutical compositions, at least one of which contains a compound of the invention. In one embodiment, the kit comprises means for separately retaining said compositions, such as a container, divided bottle; or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Method of Manufacture & Method of Treatment

The invention also provides the use of a compound of the invention in the manufacture of a medicament for the treatment or prevention of disorders where a reduction of second messenger responses mediated by cyclic 3',5'-adenosine monophosphate (CAMP) is required, wherein the medicament is prepared for administration with another therapeutic agent. The invention also provides the use of another therapeutic agent in the manufacture of medicament for treating a disease or condition mediated by cAMP for the treatment or prevention of disorders where a reduction of second messenger responses mediated by cyclic 3',5'-adenosine monophosphate (cAMP) is required, wherein the medicament is prepared for administration with a compound of the invention.

The invention also provides a compound of the invention for use in the treatment or prevention of disorders where a reduction of second messenger responses mediated by cyclic 3',5'-adenosine monophosphate (cAMP) is required, wherein the compound of the invention is prepared for administration with another therapeutic agent. The invention also provides another therapeutic agent for use in the treatment or prevention of disorders where a reduction of second messenger responses mediated by cyclic 3',5'-adenosine monophosphate (cAMP) is required, wherein the other therapeutic agent is prepared for administration with a compound of the invention. The invention also provides a compound of the invention for use in for the treatment or prevention of disorders where a reduction of second messenger responses mediated by cyclic 3',5'-adenosine. monophosphate (cAMP) is required, wherein the compound of the invention is administered with another therapeutic agent. The invention also provides another therapeutic agent for use in the treatment or prevention of disorders where a reduction of second messenger responses mediated by cyclic 3',5'-adenosine monophosphate (cAMP) is required, wherein the other therapeutic agent is administered with a compound of the invention.

The invention also provides the use of a compound of the invention in the manufacture of a medicament for the treatment or prevention of disorders where a reduction of second messenger responses mediated by cyclic 3',5'-adenosine monophosphate (cAMP) is required, wherein the patient has previously (e.g. within 24 hours) been treated with another therapeutic agent. The invention also provides the use of another therapeutic agent in the manufacture of a medicament for the treatment or prevention of disorders where a reduction of second messenger responses mediated by cyclic 3',5'-adenosine monophosphate (cAMP) is required, wherein the patient has previously (e.g. within 24 hours) been treated with a compound of the invention.

In one embodiment, the other therapeutic agent is:
(i) a presynaptic α-2 adrenergic receptor agonist, optionally clonidine, dexmedetomidine, or guanfacine;
(ii) a β-1 Adrenergic receptor antagonist ("beta-blocker"), optionally Atenolol, Metoprolol, Bisoprolol, Acebutolol, or Betaxolol.

EXAMPLES

The present invention will now be further described by way of the following non-limiting examples and with reference to the Tables and Figures:

Table 1 shows examples of novel small molecule PDE4 long form activators of Formula 1 and Formula 2 (Examples A to L), according to the present invention;

Table 2 shows activation of PDE4D5, a long form of PDE4, by Examples A to L

Table 3 shows activation of PDE4A4, another long form of PDE4, by Example A.

Table 4 shows activation of PDE4B1, another long form of PDE4, by Example A.

FIG. 1 shows activation of PDE4D5, a long form of PDE4, by Examples A, B, D and L.

Figure 2:
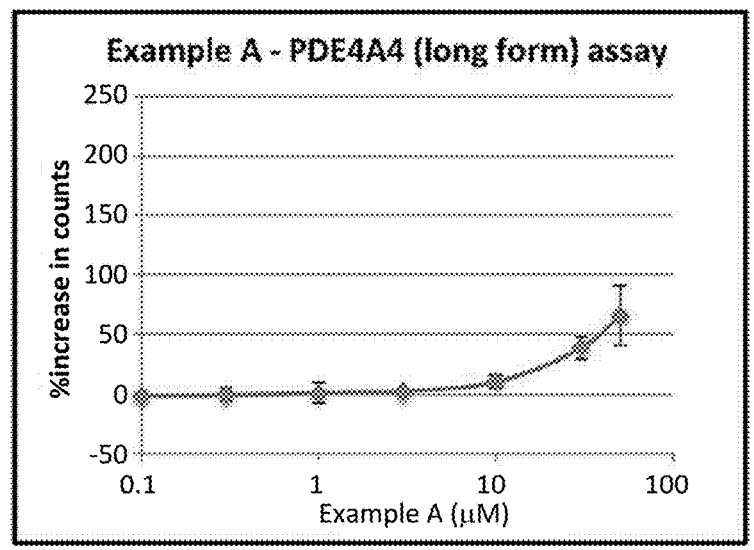
FIG. 2 shows activation of PDE4A4, another long form of PDE4, by Example A.

FIG. 2 shows activation of PDE4A4, another long form of PDE4, by Example A.

Figure 3:
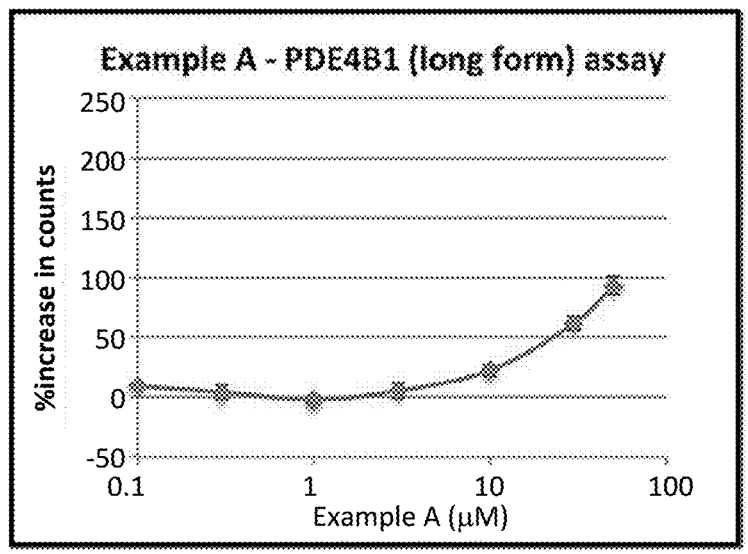
FIG. 3 shows activation of PDE4B1, another long form of PDE4, by Example A.

FIG. 3 shows activation of PDE4B1, another long form of PDE4, by Example A.

Figure 4:
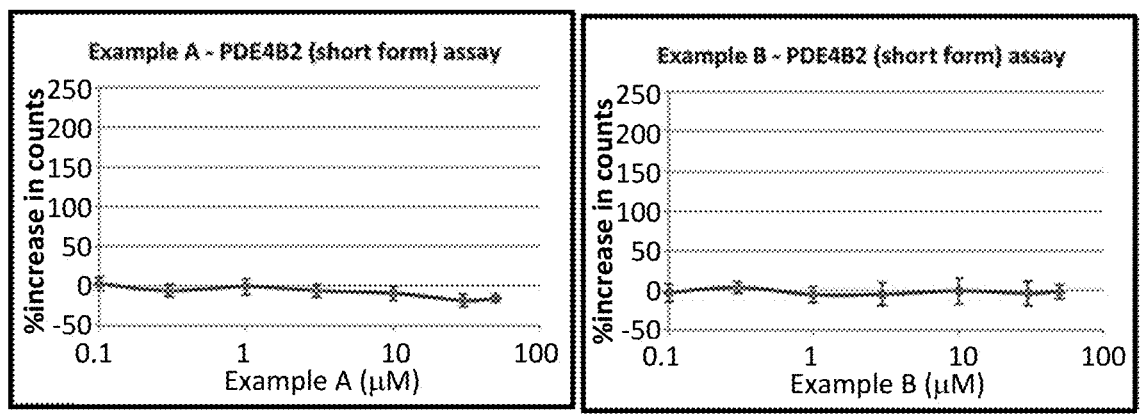
FIG. 4 shows a lack of activation of PDE4B2, a short form of PDE4, by Examples A, B, D and L using the method of Experiment 1, demonstrating selectivity for activation of PDE4 long forms over this PDE4 short form.
Figure 4:
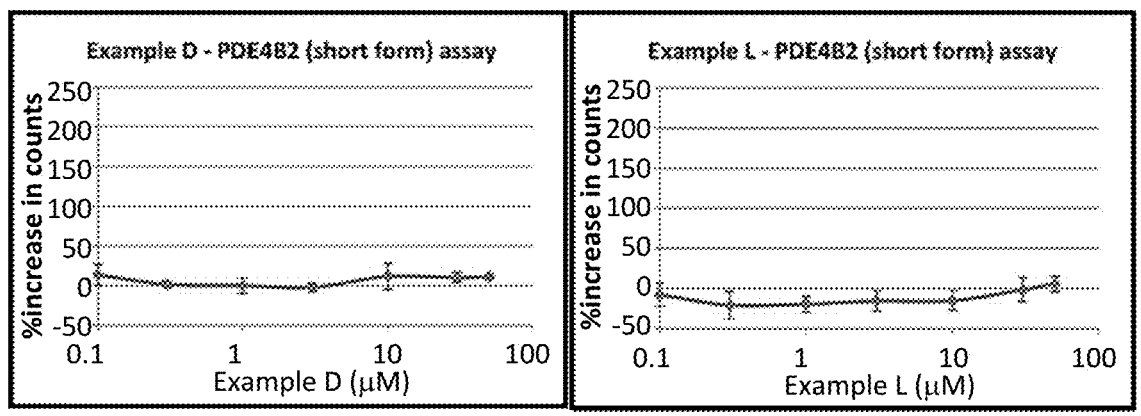

FIG. 4 shows a lack of effect on PDE4B2, a short form of PDE4, Examples A, B, D and L.

Figure 5:
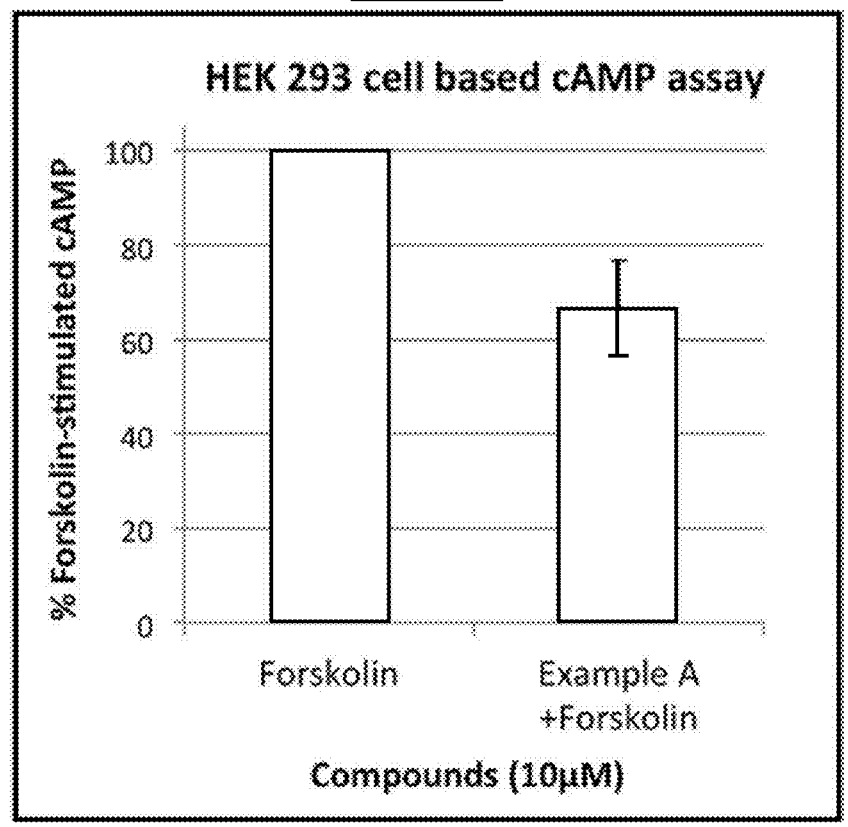
FIG. 5 shows a reduction in intracellular cAMP levels in HEK293 cells treated with a PDE4 long form activator (10 µM)—Example A—for 10 min prior to forskolin (F) (10 µM) for 2 min.

FIG. 5 shows a reduction in intracellular cAMP levels in HEK 293 cells treated with a PDE4 long form activator of the present invention (10 μM) for 10 min prior to forskolin (F) (10 μM) for 2 min.

Figure 6:
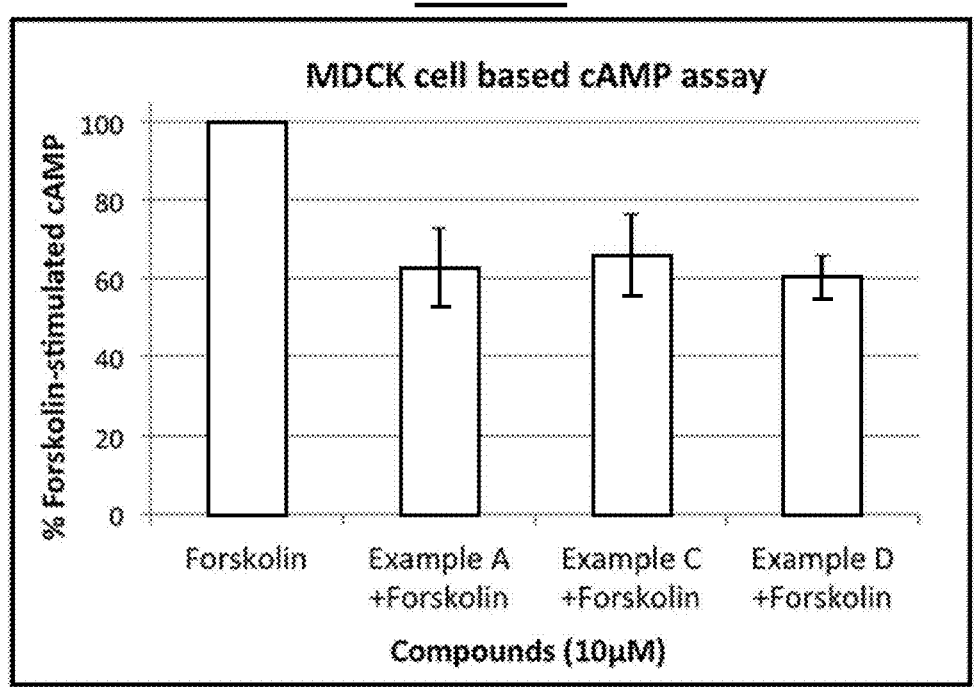
FIG. 6 shows a reduction in intracellular cAMP levels in MDCK cells treated with PDE4 long form activators (10 µM)—Examples A, C and D—for 10 min prior to forskolin (F) (10 µM) for 2 min.

FIG. 6 shows a reduction in intracellular cAMP levels in Madin-Darby canine kidney (MDCK) cells treated with PDE4 long form activators of the present invention (10 μM) for 10 min prior to forskolin (F) (10 μM) for 2 min.

FIG. 7 shows inhibition of in vitro cyst formation in MDCK cells treated with a PDE4 long form activator of the present invention.

FIG. 8 shows reversal of in vitro cyst formation in MDCK cells treated with a PDE4 long form activator of the present invention.

Figure 9:
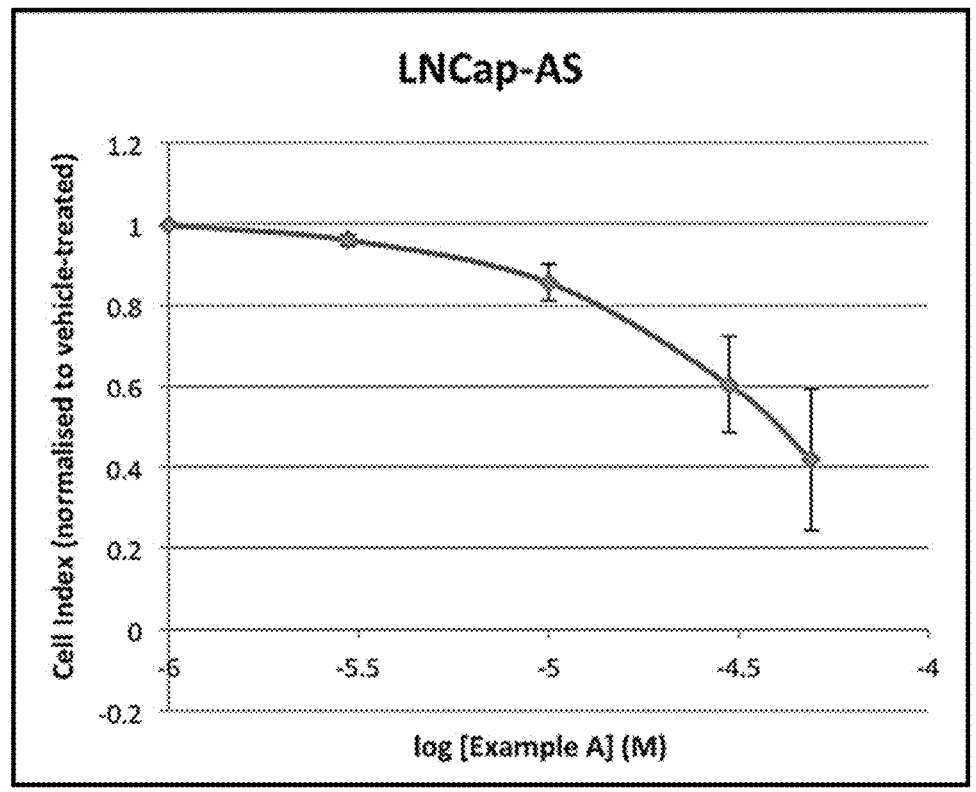
FIG. 9 shows (normalised cell index at 72 hours) that a PDE4 long form activator—Example A—inhibits the proliferation of androgen-sensitive (AS) LNCaP human prostate cancer cells in a concentration dependent manner, using the method described in Experiment 5.

FIG. 9 shows inhibition of proliferation of androgen-sensitive (AS) LNCaP human prostate cancer cells treated with a PDE4 long form activator of the present invention.

Figure 10:
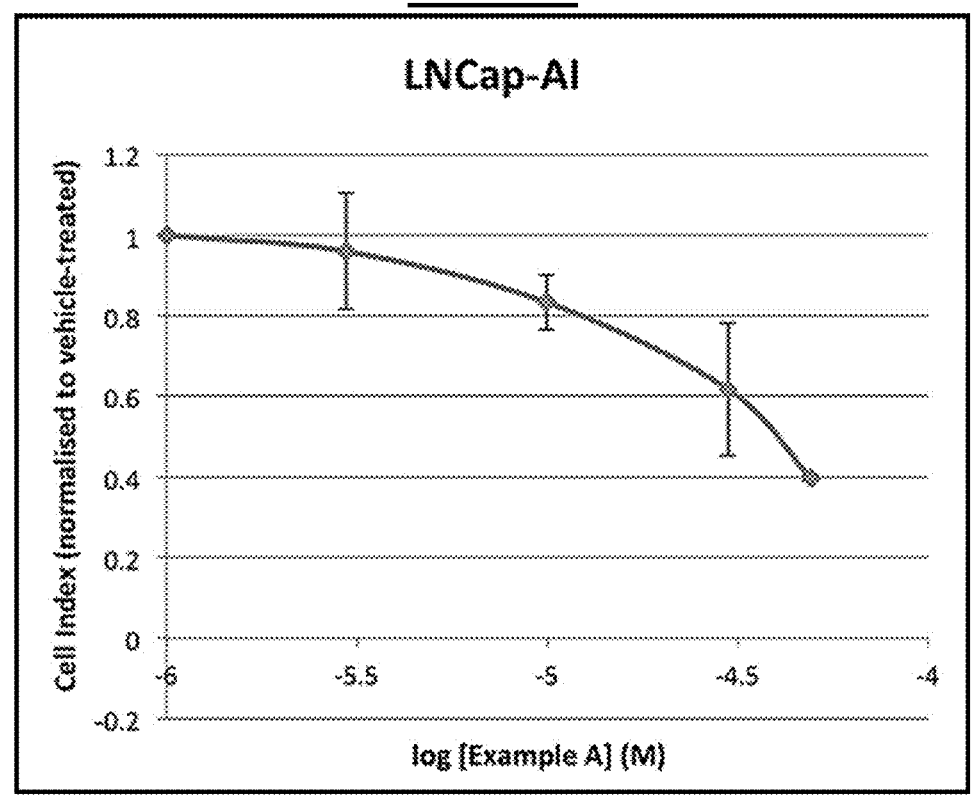
FIG. 10 shows (normalised cell index at 72 hours) that, using the method described in Experiment 5, a PDE4 long form activator—Example A—inhibits the proliferation of androgen-insensitive (AI) LNCaP human prostate cancer cells in a concentration dependent manner.

FIG. 10 shows inhibition of proliferation of androgen-insensitive (AI) LNCaP human prostate cancer cells treated with a PDE4 long form activator of the present invention.

Figure 11:
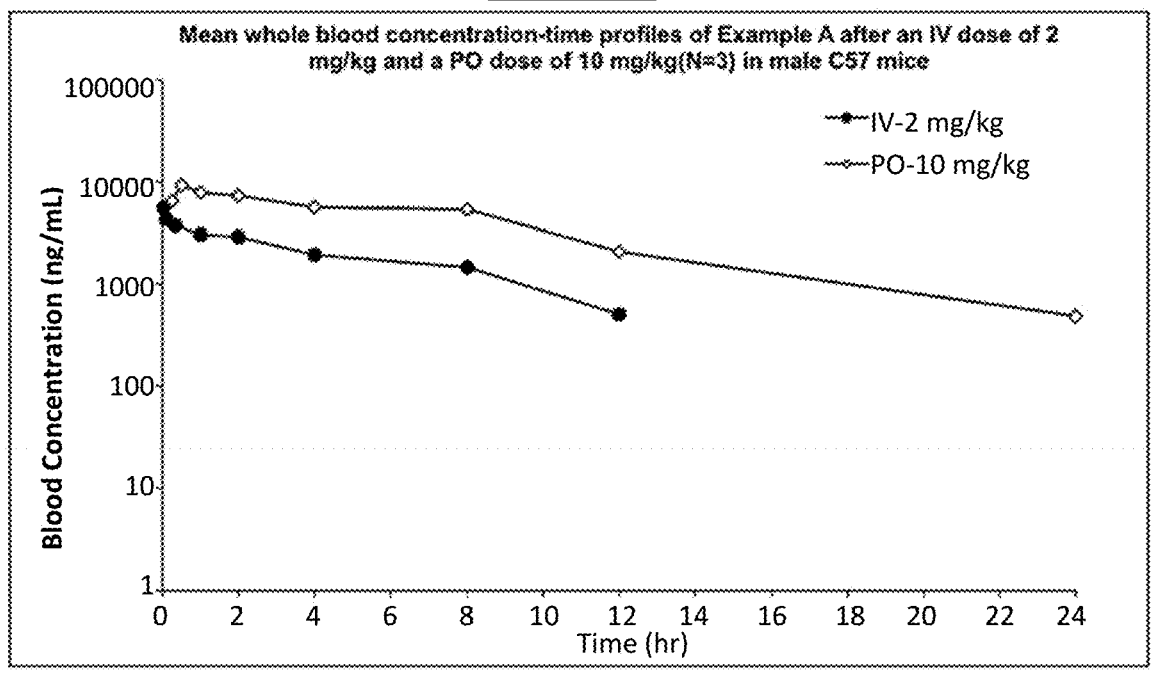
FIG. 11 shows the mouse pharmacokinetic profile of Example A, determined by whole blood analysis at defined time points after i.v. and p.o. administration to male C57 mice.

FIG. 11 shows the in vivo mouse pharmacokinetic profile of Example A, determined by whole blood analysis at defined time points after i.v. and p.o. administration to male C57 mice.

Figure 12:
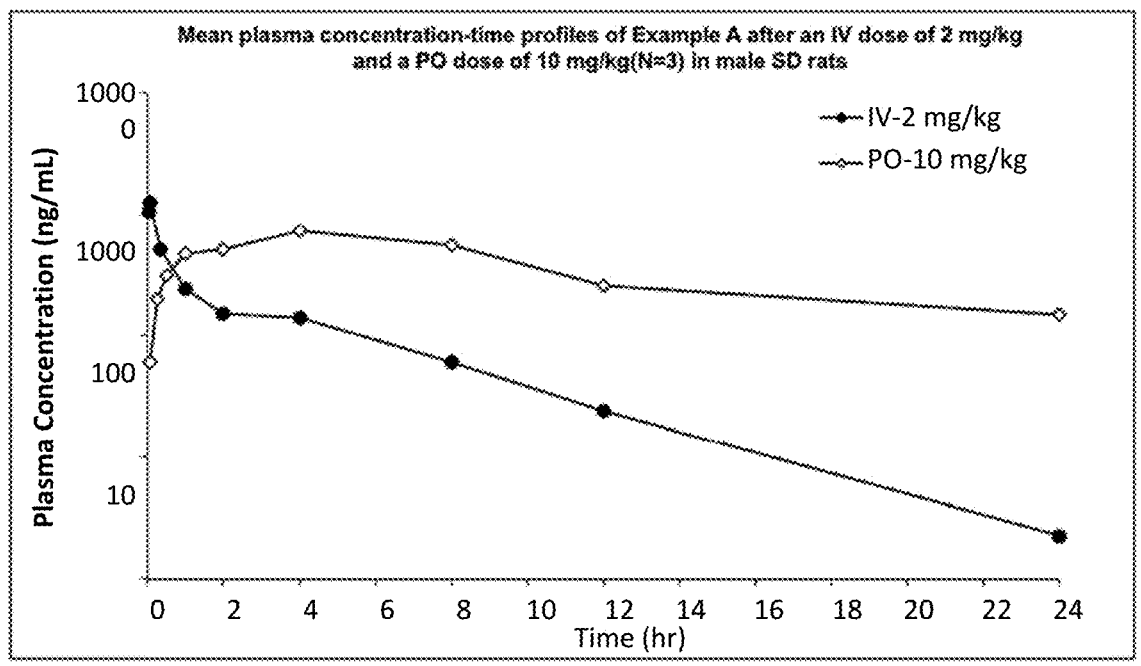
FIG. 12 shows the rat pharmacokinetic profile of Example A, determined by blood plasma analysis at defined time points after i.v. and p.o. administration to male SD rats.

FIG. 12 shows the in vivo rat pharmacokinetic profile of Example A, determined by blood plasma analysis at defined time points after i.v. and p.o. administration to male SD rats.

FIG. 13 shows (A) inhibition and (B) reversal of in vitro cyst formation in OX161 cells treated with Example A, a PDE4 long form activator of the present invention.

Experimental Details

Preparation of Novel PDE4 Long Form Activators of Formula 1 and Formula 2

Reactions were monitored by thin layer chromatography (Merck Millipore TLC Silica Gel 60 $F_{254}$). Flash column chromatography was performed on Phenomenex Strata® pre-packed silica gel columns. NMR spectra were recorded using a Bruker AV300 spectrometer at 25° C. The following abbreviations are used in the assignment of NMR signals: s (singlet), d (doublet), t (triplet), q (quartet), m (multiplet), bs (broad singlet), dd (doublet of doublet), dt (doublet of triplet).

Example A: N-(3-Fluorobenzyl)-2-[3-(4-chloro-3-fluorophenyl)-5-ethyl-1H-1,2,4-triazol-1-yl]acetamide Step 1: N-(3-Fluorobenzyl)-2-chloroacetamide To a stirred solution of 3-fluorobenzylamine (3.32 g, 26.6 mmol) and triethylamine (3.87 mL, 27.9 mmol) in, dry dichloromethane (80 mL) at −5° C. (salt/ice bath) under argon was added chloroacetyl chloride (2.22 mL, 27.9 mmol), dropwise over 10 minutes. The reaction mixture was stirred at −5° C. for a further 30 minutes, then stirred at room temperature for 2 hours. The mixture was then diluted with chloroform (50 mL), washed with saturated aqueous sodium bicarbonate solution (3×20 mL) and then brine (3×20 mL). The organic layer was then dried over anhydrous sodium sulfate, filtered through a 2 cm silica gel pad, washing with 2% methanol in chloroform, and the filtrate concentrated under reduced pressure to afford N-(3-fluorobenzyl)-2-chloroacetamide as a white solid (5.15 g, 25.5 mmol).

Step 2: N-(3-Fluorobenzyl)-2-iodoacetamide

To a stirred solution of N-(3-fluorobenzyl)-2-chloroacetamide (5.13 g, 25.4 mmol) in acetonitrile (50 mL) was added sodium iodide (4.00 g, 26.7 mmol). The mixture was refluxed at 90° C. (oil bath) for 3 h and then allowed to cool to room temperature. The precipitate was filtered off using a short pad of Celite®, washing with dichloromethane. The filtrate was concentrated under reduced pressure to afford crude product as a light brown solid. The crude product was purified by flash column chromatography, eluting with 5% to 35% ethyl acetate in petroleum ether, to afford N-(3-fluorobenzyl)-2-iodoacetamide as a pale yellow powder (7.11 g, 24.3 mmol).

Step 3: 4-Chloro-3-fluorobenzene carboximidic acid methyl ester, hydrochloride salt Hydrochloric acid solution in methanol (3N; 3 mL), chlorotrimethylsilane (3.26 g, 30.0 mmol) and 4-chloro-3-fluorobenzonitrile (2.33 g, 15 mmol) were added sequentially to a dry reaction tube, with stirring under argon at room temperature. The mixture was heated to 50° C. with stirring for 1 h, during which time a thick white precipitate formed in the mixture. Cyclopentyl methyl ether (5 mL) was added and the mixture was heated to 50° C. for a further 1 h, with periodic shaking to loosen the precipitate. The mixture was then allowed to cool to room temperature and the solid filtered off, washing with cyclopentyl methyl ether (2×5 mL) to afford 4-chloro-3-fluorobenzene carboximidic acid methyl ester, hydrochloride salt (1.43 g, 6.9 mmol).

Step 4: 3-(4-Chloro-3-fluorophenyl)-5-ethyl-1H-1,2,4-triazole

A mixture of 4-chloro-3-fluorobenzene carboximidic acid methyl ester, hydrochloride salt (187 mg, 0.83 mmol), hydrazine hydrate (0.88 mL, 18.0 mmol) and aluminium chloride (120 mg, 0.90 mmol) in toluene (30 mL) was heated to reflux for 3 h. The mixture was concentrated under reduced pressure, taken up in toluene and concentrated under reduced pressure twice more. The residue was suspended in a toluene/acetonitrile mixture (12:1, 26 mL), propionyl chloride (0.36 mL, 4.1 mmol) was added and the mixture was heated at 112° C. overnight. The mixture was concentrated under reduced pressure and purified by flash column chromatography, eluting with 20% to 25% ethyl acetate in petroleum ether, to afford 3-(4-chloro-3-fluorophenyl)-5-ethyl-1H-1,2,4-triazole (28 mg, 0.12 mmol).

Step 5: N-(3-Fluorobenzyl)-2-[3-(4-chloro-3-fluorophenyl)-5-ethyl-1H-1,2,4-triazol-1-yl]acetamide To a stirred solution of 3-(4-chloro-3-fluorophenyl)-5-ethyl-1H-1,2,4-triazole (28 mg, 0.12 mmol) in dimethyl formamide (2 mL) under argon at 0° C. was added sodium hydride (60% dispersion in mineral oil, 6.3 mg, 0.16 mmol). After 10 minutes, a solution of N-(3-fluorobenzyl)-2-iodoacetamide (46 mg, 0.16 mmol) in dimethylformamide (3 mL) was added dropwise. The reaction was allowed to warm to room temperature and stirred for 72 h. The mixture was concentrated under reduced pressure and then partitioned between chloroform (25 mL) and water (10 mL). The organic layer was separated, washed with brine (2×10 mL), dried over anhydrous magnesium sulphate, filtered and concentrated under reduced pressure. The crude product was purified by flash column chromatography, eluting with 25% to 35% ethyl acetate in petroleum ether and the product recrystallized from chloroform/methanol to afford N-(3-fluorobenzyl)-2-[3-(4-chloro-3-fluorophenyl)-5-ethyl-1H-1,2,4-triazol-1-yl]acetamide as a white solid (15.3 mg, 0.039 mmol).

$^1$H NMR: $\delta_H$ (300 MHz, CDCl$_3$) 7.89-7.80 (2H, m), 7.56-7.43 (1H, m), 7.38-7.22 (1H, m), 7.00 (3H, m), 6.62 (1H, s), 4.87 (2H, s), 4.50 (2H, d, J 5.9), 2.85 (2H, q, J 7.6), 1.41 (3H, t, J 7.6).

Example B: N-Benzyl-2-[3-(4-chlorophenyl)-5-methoxymethyl-1H-1,2,4-triazol-1-yl]acetamide Step 1: N-Benzyl-2-chloroacetamide To a stirred solution of benzylamine (7.64 mL, 70.0 mmol) and triethylamine (10.22 mL, 73.5 mmol) in toluene (70 mL) at −5° C. (salt/ice bath) was added chloroacetyl chloride (5.85 mL, 73.5 mmol), dropwise over 10 minutes. The reaction mixture was stirred at −5° C. for a further 30 minutes, then stirred at room temperature for 2 hours. The mixture was then diluted with ethyl acetate (70 mL), washed with saturated aqueous sodium bicarbonate solution (3×30 mL) and brine (3×30 mL). The organic layer was then dried over anhydrous sodium sulphate, filtered and concentrated under reduced pressure to afford N-benzyl-2-chloroacetamide as a white solid (11.01 g, 59.96 mmol).

Step 2: N-Benzyl-2-iodoacetamide

To a stirred solution of N-benzyl-2-chloroacetamide (12.43 g, 67.66 mmol) in acetonitrile (60 mL) was added sodium iodide (10.65 g, 71.04 mmol). The mixture was gently refluxed at 95° C. (oil bath) for 2.5 hours and then allowed to cool to room temperature. The precipitate was filtered off using a short pad of Celite®, washing with ethyl acetate. The filtrate was concentrated under reduced pressure to afford crude product as a light brown solid. Trituration with an ethyl acetate/dichloromethane mixture followed by filtration afforded N-benzyl-2-iodoacetamide (3.91 g). The filtrate was concentrated under reduced pressure and purified by flash column chromatography eluting with 50% chloroform/ethyl acetate to afford further product (2.35 g). The pad of Celite® was further washed with dichloromethane and then chloroform to afford further product (7.10 g). The product samples were combined and dried in air to afford a single batch of N-benzyl-2-iodoacetamide as a white powder (13.14 g, 47.76 mmol).

Step 3: 3-(4-Chlorophenyl)-5-methoxymethyl-1H-1,2,4-triazole

To a solution of sodium methoxide in dry methanol (0.5M; 4 mL) was added 4-chlorobenzonitrile (1.38 g, 10 mmol). The resulting suspension was stirred at room temperature under argon for 2.5 h. A solution of methoxyacetic acid hydrazide (1.04 g, 10 mmol) in dry methanol (10 mL) was added to the mixture, resulting in a clear solution, which was heated to reflux for 3 h and then stirred at room temperature overnight. The mixture was concentrated under reduced pressure and purified by flash column chromatography eluting with 20% to 60% ethyl acetate in petroleum ether to afford 3-(4-chlorophenyl)-5-methoxymethyl-1H-1,2,4-triazole as a white solid (412 mg, 1.84 mmol).

Step 4: N-Benzyl-2-[3-(4-chlorophenyl)-5-methoxymethyl-1H-1,2,4-triazol-1-yl]acetamide To a stirred solution of 3-(4-chlorophenyl)-5-methoxymethyl-1H-1,2,4-triazole (45 mg, 0.20 mmol) in dimethyl formamide (2 mL) under argon at 0° C. was added sodium hydride (60% dispersion in mineral oil, 9.6 mg, 0.24 mmol).

After 10 minutes, a solution of N-benzyl-2-iodoacetamide (66 mg, 0.24 mmol) in dimethylformamide (3 mL) was added dropwise. The reaction was allowed to warm to room temperature and stirred for 72 h. The mixture was concentrated under reduced pressure and then partitioned between dichloromethane (25 mL) and water (10 mL). The organic layer was separated, washed with brine (2×10 mL), dried over anhydrous magnesium sulphate, filtered and concentrated under reduced pressure. The crude product was purified by flash column chromatography, eluting with 40% to 50% ethyl acetate in petroleum ether and the product recrystallized from chloroform/methanol/hexane to afford N-benzyl-2-[3-(4-chlorophenyl)-5-methoxymethyl-1H-1,2,4-triazol-1-yl]acetamide as a white solid (22 mg, 0.059 mmol).

$^1$H NMR: $\delta_H$ (300 MHz, CDCl$_3$) 8.07-7.96 (2H, m), 7.49-7.39 (2H, m), 7.38-7.19 (5H, m 6.48 (1H, s), 5.01 (2H, s), 4.70 (2H, s), 4.50 (2H, d, J 5.8), 3,40 (3H, s).

Example C: N-Benzyl -2-[3-(4-chlorophenyl)-5-methyl-1H-1,2,4-triazol-1-yl]acetamide The title compound was prepared according to the method of Example B, using acethydrazide instead of methoxyacetic acid hydrazide.

$^1$H NMR: $\delta_H$ (300 MHz, CDCl$_3$) 8.05-7.93 (2H, m), 7.47-7.39 (2H, m), 7.38-7.23 (5H, m), 6.64 (1H, s), 4.85 (2H, s), 4.50 (2H, d, J 5.8), 2.55 (3H, s).

Example D: N-(3-Fluorobenzyl)-2-{3-[4-(trifluoromethoxy)phenyl]-5-methoxymethyl-1H-1,2,4-triazol-1-yl}acetamide The title compound was prepared according to the method of Example B, steps 3 and 4, using 4-(trifluoromethoxy) benzonitrile instead of 4-chlorobenzonitrile and N-(3-fluorobenzyl)-2-iodoacetamide (as prepared in Example A) instead of N-benzyl-2-iodoacetamide.

$^1$H NMR: $\delta_H$ (300 MHz, CDCl$_3$) 8.08-8.12 (2H, m), 7.19-7.34 (3H, m), 6.91-7.01 (3H, m), 6.45 (1H, bs), 5.00 (2H, s), 4.68 (2H, s), 4.46 (2H, d, J 5.9)', 3.42 (3H, s).

Example E: N-(3-Chlorobenzyl)-2-[3-(4-chloro-3-fluorophenyl)-5-ethyl-1H-1,2,4-triazol-1-yl]acetamide Step 1: 3-(4-Chloro-3-fluorophenyl)-5-ethyl-1H-1,2,4-triazole The triazole was prepared according to the method of Example B, step 3, using 4-chloro-3-fluorobenzonitrile instead of 4-chlorobenzonitrile and propionic acid hydrazide instead of methoxyacetic acid hydrazide.

Step 2: O-tert-butyl-2-[3-(4-chloro-3-fluorophenyl)-5-ethyl-1H-1,2,4-triazol-1-yl]acetate To a stirred solution of 3-(4-chloro-3-fluorophenyl)-5-ethyl-1H-1,2,4-triazole (492 mg, 2.18 mmol) in dimethylformamide (10 mL) at room temperature under argon was added sodium hydride (60% dispersion in mineral oil, 105 mg, 2.62 mmol). After 10 minutes, tert-butylbromoacetate (386 μL, 2.62 mmol) was added dropwise over 1 minute. The mixture was stirred at room temperature for 18 h. The mixture was concentrated under reduced pressure and then purified by flash column chromatography, eluting with 5% to 15% ethyl acetate in petroleum ether to afford O-tert-butyl-2-[3-(4-chloro-3-fluorophenyl)-5-ethyl-1H-1,2,4-triazol-1-yl]acetate as a white solid (661 mg, 1.94 mmol).

Step 3: 2-[3-(4-Chloro-3-fluorophenyl)-5-ethyl-1H-1,2,4-triazol-1-yl]acetic acid To a stirred solution of O-tert-butyl-2-[3-(4-chloro-3-fluorophenyl)-5-ethyl-1H-1,2,4-triazol-1-yl]acetate (661 mg, 1.94 mmol) in dichloromethane (30 mL) at 0° C. was added trifluoroacetic acid (10 mL) dropwise over 5 minutes. The reaction was allowed to warm to room temperature and stirred for 18 h. The mixture was concentrated under reduced pressure to afford crude 2-[3-(4-chloro-3-fluorophenyl)-5-ethyl-1H-1,2,4-triazol-1-yl]acetic acid as a viscous light brown oil, which was used without further purification.

Step 4: 2-[3-(4-Chloro-3-fluorophenyl)-5-ethyl-1H-1,2,4-triazol-1-yl]acetyl chloride To a stirred solution of 2-[3-(4-chloro-3-fluorophenyl)-5-ethyl-1H-1,2,4-triazol-1-yl]acetic acid (crude material from step 3, ca. 1.94 mmol) in dichloromethane (30 mL) was added thionyl chloride (2.32 mL, 32.0 mmol). The mixture was heated under reflux for 6 h. The mixture was concentrated under reduced pressure to afford crude 2-[3-(4-chloro-3-fluorophenyl)-5-ethyl-1H-1,2,4-triazol-1-yl]acetyl chloride (ca. 1.94 mmol), which was taken up in dichloromethane (33 mL) and used without further purification.

Step 5: N-(3-Chlorobenzyl)-2-[3-(4-chloro-3-fluorophenyl)-5-ethyl-1H-1,2,4-triazol-1-yl]acetamide To a stirred solution of 3-chlorobenyzlamine (39 mg, 0.27 mmol) and triethylamine (63 μL, 0.45 mmol) in dichloromethane at 0° C. was added 2-[3-(4-chloro-3-fluorophenyl)-5-ethyl-1H-1,2,4-triazol-1-yl]acetyl chloride (crude material from step 4, ca. 0.18 mmol) in dichloromethane (3 mL). The reaction was allowed to warm to room temperature and stirred for 18 h. The mixture was concentrated under reduced pressure and then purified by flash column chromatography, eluting with 0.5% to 1% methanol in dichloromethane to afford a white solid, which was further purified by trituration with chloroform and hexane to afford N-(3-chlorobenzyl)-2-[3-(4-chloro-3-fluorophenyl)-5-ethyl-1H-1,2,4-triazol-1-yl]acetamide as a white solid (30.4 mg, 0.075 mmol).

$^1$H NMR: $\delta_H$ (300 MHz, CDCl$_3$) 7.84 (1H, dd, J 9.9, 1.8), 7.79 (1H, ddd, J 8.3, 1.9, 0.8), 7.44 (1H, dd, J 8.2, 7.6), 7.19-7.25 (3H, m), 7.08-7.12 (1H, m), 6.59 (1H, bs), 4.84 (2H, s), 4.45 (2H, d, J 5.9), 2.82 (2H, q, J 7.6), 1.38 (3H, t, J 7.6).

Example F: N-(3-Cyanobenzyl)-2-[3-(4-chloro-3-fluorophenyl)-5-ethyl-1H-1,2,4-triazol-1-yl]acetamide The title compound was prepared according to the method of Example E, using 3-cyanobenzylamine instead of 3-chlorobenzylamine in Step 5.

$^1$H NMR: $\delta_H$ (300 MHz, CDCl$_3$) 7.78-7.86 (2H, m), 7.53-7.59 (2H, m), 7.40-7.49 (3H, m), 6.71 (1H, bs), 4.85 (2H, s), 4.50 (2H, d, J 6.2), 2.82 (2H, q, J 7.6), 1.38 (3H, t, J 7.6).

Example G: N-[3-(Trifluoromethyl)benzyl]-2-[3-(4-chloro-3-fluorophenyl)-5-ethyl-1H-1,2,4-triazol-1-yl]acetamide The title compound was prepared according to the method of Example E, using 3-(trifluoromethyl)benzylamine instead of 3-chlorobenzylamine in Step 5.

$^1$H NMR: $\delta_H$ (300 MHz, CDCl$_3$) 7.83 (1H, dd, J 9.9, 1.8), 7.78 (1H, ddd, J 8.3, 1.9, 0.8), 7.51-7.56 (1H, m), 7.41-7.47 (4H, m), 6.64 (1H, bs), 4.85 (2H, s), 4.53 (2H, d, J 6.0), 2.82 (2H, q, J 7.6), 1.37 (3H, t, J 7.6).

Example H: N-(3-Methoxybenzyl)-2-[3-(4-chloro-3-fluorophenyl)-5-ethyl-1H-1,2,4-triazol-1-yl]acetamide The title compound was prepared according to the method of Example E, using 3-methoxybenzylamine instead of 3-chlorobenzylamine in Step 5.

$^1$H NMR: $\delta_H$ (300 MHz, CDCl$_3$) 7.83 (1H, dd, J 9.9, 1.9), 7.78 (1H, ddd, J 8.3, 1.9, 0.8), 7.43 (1H, dd, J 8.2, 7.5), 7.21 (1H, d, J 8.0), 6.74-6.82 (3H, m), 6.53 (1H, bs), 4.83 (2H, s), 4.44 (2H, d, J 5.7), 3.76 (3H, s), 2.81 (2H, q, J 7.6), 1.37 (3H, t, J 7.6).

Example I: N-[3-(Trifluoromethoxy)benzyl]-2-[3-(4-chloro-3-fluorophenyl)-5-ethyl-1H-1,2,4-triazol-1-yl]acetamide The title compound was prepared according to the method of Example E, using 3-(trifluoromethoxy)benzylamine instead of 3-chlorobenzylamine in Step 5.

$^1$H NMR: $\delta_H$ (300 MHz, CDCl$_3$) 7.84 (1H, dd, J 9.9, 1.8), 7.79 (1H, ddd, J 8.3, 1.9, 0.8), 7.44 (1H, dd, J 8.2, 7.5), 7.34 (1H, t, J 7.9), 7.11-7.17 (2H, m), 7.06-7.08 (1H, m), 6.61 (1H, bs), 4.85 (2H, s), 4.49 (2H, d, J 6.0), 2.81 (2H, q, J 7.6), 1.37 (3H, t, J 7.6).

Example J: N-(2-Fluorobenzyl)-2-[3-(4-chloro-3-fluorophenyl)-5-ethyl-1H-1,2,4-triazol-1-yl]acetamide The title compound was prepared according to the method of Example E, using 2-fluorobenzylamine instead of 3-chlorobenzylamine in Step 5.

$^1$H NMR: $\delta_H$ (300 MHz, CDCl$_3$) 7.84 (1H, dd, J 10.0, 1.9), 7.81-7.78 (1H, m), 7.42-7.47 (1H, m), 7.19-7.33 (2H, m), 7.00-7.12 (2H, m), 6.68 (1H, bs), 4.80 (2H, s), 4.51 (2H, d, J 5.9), 2.79 (2H, q, J 7.6), 1.35 (3H, t, J 7.6).

Example K: N-(4-Fluorobenzyl)-2-[3-(4-chloro-3-fluorophenyl)-5-ethyl-1H-1,2,4-triazol-1-yl]acetamide The title compound was prepared according to the method of Example E, using 4-fluorobenzylamine instead of 3-chlorobenzylamine in Step 5.

$^1$H NMR: $\delta_H$ (300 MHz, CDCl$_3$) 7.83 (1H, dd, J 10.0, 1.8), 7.77 (1H, ddd, J 8.3, 1.9, 0.8), 7.44 (1H, dd, J 8.2, 7.5), 7.16-7.22 (2H, m), 6.96-7.04 (2H, m), 6.51 (1H, bs), 4.82 (2H, s), 4.43 (2H, d, J 5.9), 2.80 (2H, q, J 7.6), 1.36 (3H, t, J 7.6).

Example L: N-(3,4-Dimethoxybenzyl)-2-[3-(4-chloro-3-fluorophenyl)-5-ethyl-1H-1,2,4-triazol-1-yl]acetamide The title compound was prepared according to the method of Example E, using 3,4-dimethoxybenzylamine instead of 3-chlorobenzylamine in Step 5.

$^1$H NMR: $\delta_H$ (300 MHz, CDCl$_3$) 7.85 (1H, dd, J 10.0, 1.8), 7.77 (1H, ddd, J 8.3, 1.9, 0.8), 7.44 (1H, dd, J 8.0, 7.7), 6.73-6.81 (3H, m), 6.45 (1H, bs), 4.82 (2H, s), 4.40 (2H, d, J 5.7), 3.86 (3H, s), 3.81 (3H, s), 2.81 (2H, q, J 7.6), 1.37 (3H, t, J 7.6).

Biological Assays

Cell Culture

HEK 293 and MDCK cells (Public Health England, Cell Culture Collections) were maintained in DMEM supplemented with 10% (v/v) fetal bovine serum (Seralab), 2 mM L-glutamine, 1,000 U penicillin and 1,000 µg streptomycin (Life Technologies); termed complete media. Clonal HEK 293 cell lines were maintained in complete media supplemented with 0.6 mg/mL G418 (Enzo Life Sciences).

Experiment 1: Identification of PDE4 Long Form Activators of the Present Invention Using Full-Length Human PDE4 Isoforms PDE4D5, PDE4A4, PDE4B1 and PDE4B2

(Marchmont, R. J. and Houslay, M. D. *Biochem. J.* 187: 381-92, 1980)

Cell Line Generation

HEK 293 cells were transfected with pDEST™ PDE4 expression vectors using Lipofectamine LTX/Plus reagent (Invitrogen) as outlined by the manufacturer and clonal isolates expanded to obtain cell lines that stably expressed the full-length human PDE4D5, PDE4A4 and PDE4B1 long isoforms and the full length human PDE4B2 short isoform. These were called the HEK-PDE4D5, HEK-PDE4A4, HEK-PDE4B1 and HEK-PDE4B2 cell lines, respectively.

Lysate Preparation (Using PDE4D5 as a Typical Example)

HEK-PDE4D5 cells were seeded out in 100 mm plates and incubated at 37° C. in an atmosphere of 5% CO$_2$, 95% air. Cell lysates were prepared using KHEM buffer [50 mM KCl, 10 mM EGTA, 50 mM HEPES (pH 7.2), 1.92 mM MgCl$_2$].

To prepare the cell lysates, the 100 mm plates containing the cells were placed on ice and washed with ice-cold PBS (phosphate buffered saline, pH 7.4). KHEM buffer (500 µl) was added to the cells. Cells were then scraped off the plate and triturated using a needle (BD Microlance™ 0.8, 40 mm). The lysed cells were then centrifuged at 2000 rpm for 10 minutes to remove cell debris and the supernatant (cell lysate containing recombinant PDE4D5) was transferred to a fresh tube and kept on ice.

Cytosol Fraction Preparation (Using PDE4D5 as a Typical Example)

The cell lysate containing recombinant PDE4D5 was transferred into a centrifuge tube and placed into an ultracentrifuge (BECKMAN COULTER) and spun at high speed (100,000 g) for 30 minutes at 4° C. The cytosol fraction was then collected and its protein amount determined using a BCA protein assay.

PDE Assay (Using PDE4D5 as a Typical Example)

PDE assays were performed using a final concentration of 10 mM Tris/5 mM MgCl$_2$ and 1 µM [3H]-cAMP (Perkin Elmer) plus PDE4D5 cell lysate cytosol fraction, containing over-expressed PDE4D5, with and without test compound. Incubations were performed at 30° C. for 5 minutes. The samples were then placed in a boiling water bath for 2 minutes to denature the PDE enzyme, and returned to ice. Samples were allowed to cool for 1.0 min after which snake venom 5'-nucleotidase (25 µl, 1 mg/ml; Sigma) was added. The tubes were vortexed and incubated in a water bath at 30° C. for 10 minutes, to attain conversion of [3H]-5'-AMP to [3H]-adenosine, and then placed on ice. Dowex ion exchange resin (Sigma) prepared as a 1:1 Dowex:water stock was thoroughly re-suspended and diluted 2:1 with ethanol. The resulting Dowex suspension (0.4 ml) was added to each tube. Tubes were vortexed to mix and then incubated on ice for at least 15 minutes before a final vortex. The Dowex resin was pelleted by centrifugation at 13,000 g at 4° C. for 3 minutes and 150 µl of the supernatant was removed to an Eppendorf tube containing 1 ml of Scinti-Safe3 scintillation fluid (Fisher). Tubes were vortexed thoroughly to mix and the recovered [3H]-adenosine was quantified by measuring counts over 1 minute in a scintillation counter.

Compounds of the present invention activated the PDE4 long forms PDE4D5, PDE4A4 and PDE4B1 in a concentration dependent manner. Under the same assay conditions, compounds of the present invention did not activate the PDE4 short form, PDE4B2.

Data are shown in graphical form in FIGS. 1 to 4.

Experiment 2: Reduction of Intracellular cAMP Levels in HEK 293 or MDCK Cells by PDE4 Long Form Activators HEK 293 or MDCK cells were seeded at 100,000 cells per well, and left to adhere overnight. The cells were then treated with the compound indicated (10 µM) for 10 minutes, prior to stimulation with forskolin (10 µM, Sigma) for 2 minutes. Media was aspirated, and hydrochloric acid (0.1M) was added to lyse the cells. The cAMP assay (Enzo Life Sciences) was performed according to the manufacturers instructions.

Compounds of the present invention reduced intracellular cAMP levels in forskolin stimulated HEK 293 or MDCK cells.

Data are shown in graphical form in FIGS. 5 and 6.

Experiment 3: Inhibition of In Vitro Cyst Formation in MDCK Cells Treated with PDE4 Long Form Activators In this study, the well-established three-dimensional (3D) MDCK cell model was used to investigate the effects of PDE4 long form activators on the formation of kidney cysts and evaluate their potential in the treatment of polycystic kidney diseases. 3D cysts were generated based on the method of Mao et al. (Mao, Z., Streets, A. J., Ong, A. C. M. *Am. J. Physiol. Renal Physiol.* 300(6): F1375-F1384, 2011), with some modifications. MDCK cells (50,000 cells/well) were seeded into collagen (Life Technologies; final concentration 1 mg/mL), containing 17 mM NaOH in DMEM, supplemented with 2% (v/v) FBS, 2 mM L-glutamine and 2 mM L-glutamine, 1,000 U penicillin and 1,000 µg streptomycin (DMEM-2% FBS), on ice. Upon gelling at 37° C., 1 mL of DMEM-2% FBS was added along with the test compound indicated in the presence of 10 µM forskolin (Sigma) and 1 µg/mL [Arg$^8$]-vasopressin acetate salt (Sigma). Media was replenished every 2 days for 20 days; at every feed, test compound, forskolin and vasopressin were added.

Phase-contrast images were obtained on the Motic microscope (×200 magnification) every 2 days for 20 days. Per condition, 10 images were taken (in duplicate) and the average cyst radius measured.

Compounds of the present invention inhibited in vitro cyst formation in the MDCK cells in a concentration dependent manner.

The day 20 phase-contrast images and cyst radius graphs for Example A are shown in FIG. 7.

Experiment 4: Reversal of In Vitro Cyst Formation in MDCK Cells Treated with PDE4 Long Form Activators In this study, the potential of PDE4 long form activators to reverse the formation of pre-formed cysts was evaluated. The experiment was carried out according to the method of Experiment 3. For the first 10 days, forskolin and vasopressin were added at every feed (every 2 days) but no test compound was added. For the next 10 days, the test compound, forskolin and vasopressin were added at every feed (every 2 days).

Phase-contrast images were obtained on the Motic microscope (×200 magnification) every 2 days for 20 days. Per condition, 10 images were taken (in duplicate) and the average cyst radius measured.

Compounds of the present invention reversed in vitro cyst formation in the MDCK cells in a concentration dependent manner.

The day 20 phase-contrast images and cyst radius graphs for Example A are shown in FIG. 8.

Experiment 5: Inhibition of Proliferation of LNCaP Human Prostate Cancer Cells

In this study, the potential utility of PDE4 long form activators in the treatment of prostate cancer was studied using the LNCaP human prostate cancer cell line. The experiments were carried out according to the method described by Henderson et al. (Henderson, D. J. P., Byrne, A., Dulla, K., Jenster, G., Hoffmann, R., Baillie, G. S., Houslay, M. D. *Br. J. Cancer* 110: 1278-1287, 2014).

LNCaP Cell Culture

Androgen-sensitive (AS) LNCaP cells were maintained in RPMI1640 supplemented with 10% FBS (Seralabs), 2 mM L-glutamine and 1,000 U penicillin-streptomycin. LNCaP androgen-insensitive (AI) cells were generated in-house by culturing the LNCaP-AS cells in RPMI1640 supplemented with 10% charcoal stripped FBS, 2 mM L-glutamine and 1,000 U penicillin-streptomycin for a minimum of four weeks. All tissue culture reagents were from Life Technologies.

Xcelligence (Roche) Proliferation Assay

Cell proliferation is measured as a function of changing electrical impedance. Values are represented by cell index number, a dimensionless unit of measurement representing the cell status, which increases as cells adhere to 96-well electrode plates and divide.

LNCaP AI/AS cells were plated at a density of 25,000 cells per well in a 96-well electrode plate (in triplicate), in the presence/absence of various concentrations of test compound.

Cell indices were measured every 10 minutes for up to 100 hours, analysed using RICA software and normalised to the cell index of vehicle-treated cells (n=3).

The effects of Example A on proliferation of androgen-sensitive (AS) LNCaP human prostate cancer cells are shown in FIG. 9.

The effects of Example A on proliferation of androgen-insensitive (AI) LNCaP human prostate cancer cells are shown in FIG. 10.

Experiment 6: Measurement of In Vitro Clearance of Example A Using Human Hepatocytes Human hepatocyte stability is considered the gold standard method for evaluating the hepatic metabolism of drugs in vitro. The in vitro clearance of Example A was evaluated using cryopreserved human hepatocytes according to the method of Lau et al. (Lau, Y. Y. et al. *Drug Metab. Dispos.* 30: 1446-1454, 2002) with minor modifications.

Cryopreserved hepatocytes were thawed in a water bath at 37° C. and transferred to a tube containing 50 ml of hepatocyte thaw medium. The hepatocytes were centrifuged at 500 rpm for 3 min. The supernatant was removed and the hepatocytes were resuspended in medium, mixed gently and centrifuged again at 500 rpm for 3 min. The supernatant was discarded and the hepatocyte pellet was gently resuspended in medium to a final density of 2 million cells/ml.

Incubations were carried out at a final test compound concentration of 1 µM. Stock solutions of the compounds were prepared in DMSO and diluted to the desired concentrations before adding to the hepatocytes. Incubations were carried out with a hepatocyte concentration of 1 million cells/ml. Samples (100 µL) were incubated at 37° C. for 0, 15, 30, 60 and 120 min in duplicate. At the end of the incubation time, 200 µl of acetonitrile with internal standard was added and the wells were sealed.

The samples were sonicated for 2 min and centrifuged at 6000 rpm for 10 min, and 50 µL of the supernatant was transferred into a 96-well plate containing 50 µL of ultrapure water for LC-MS/MS analysis.

The samples were analysed by LC-MS/MS using a Sciex API 4000™ system. The half-life of Example A in this assay was 54 minutes, indicating that Example A is moderately stable in human hepatocytes.

Experiment 7: Pharmacokinetic Profile of Example A in Male C57 Mice

Example A was dissolved in 5% DMA+10% Solutol+ 85%(10% HPBCD in water) to afford a clear dosing solution of 1 mg/mL. The dosing solution was administered to three mice at 2 mg/kg i.v. via the tail vein and to three further mice at 10 mg/kg p.o. via oral gavage. Blood samples (ca. 20 µL) were collected at 2, 5, 20 min, 1, 2, 4, 8 and 12 h after i.v. dosing and at 15, 30 min, 1, 2, 4, 8, 12 and 24 h after oral dosing. The blood samples were diluted with 3 volumes of distilled water and stored at −80° C. until analysis. The samples were analysed by UPLC-MS/MS (API 5500).

Example A exhibited 66% oral bioavailability in male C57 mice, with a terminal half life of 4.9 hours after oral dosing and 4.2 hours after i.v. dosing. No abnormal effects were observed in the mice. The mean whole blood concentration-time profiles of Example A. after i.v. and p.o. dosing are shown in FIG. 11.

Experiment 8: Pharmacokinetic Profile of Example A in Male SD Rats

Example A was dissolved in 5% DMA+10% Solutol+ 85%(10% HPBCD in saline) to afford a clear dosing solution of 1 mg/mL. The dosing solution was administered to three rats at 2 mg/kg i.v. via the foot dorsal vein and to three further rats at 10 mg/kg p.o. via oral gavage. Blood samples (ca. 150 µL) were collected at 2, 5, 20 min, 1, 2, 4, 8, 12 and 24 h after i.v. dosing and at 5, 15, 30 min, 1, 2, 4, 8, 12 and 24 h after oral dosing. The blood samples were centrifuged at 4° C. (2000 g, 5 min) within 15 min of sample collection to obtain plasma samples. Plasma samples were stored at −80° C. until analysis. The samples were analysed by UPLC-MS/MS (API 4000).

Example A exhibited 100% oral bioavailability in male SD rats, with a terminal half life of 9.1 hours after oral dosing and 2.2 hours after i.v. dosing. No abnormal effects were observed in the rats. The mean plasma concentration-time profiles of Example A after i.v. and p.o. dosing are shown in FIG. 12.

Experiment 9: Inhibition of In Vitro Cyst Formation in OX161 Cells Treated with PDE4 Long Form Activators of the Present Invention In this study, a human ADPKD patient-derived (OX161) cell line was used to investigate the effects of PDE4 long form activators on the formation of kidney cysts in vitro and evaluate their potential in the treatment of polycystic kidney diseases. Conditionally immortalised OX161 cystic tubular epithelial cells were generated from human kidneys removed for clinical indications from ADPKD patients with characterised PKD1 (PC1) mutations (Parker, E., Newby, L. J., Sharpe, C. C., Rossetti, S., Streets, A. J., Harris, P. C., O'Hare, M. J., Ong, A. C. M. *Kidney Int.* 72(2): 157-165, 2007).

OX161 cells (50,000 cells/well) were seeded into collagen (Life Technologies; final concentration 1 mg/mL), containing 17 mM NaOH in DMEM, supplemented with 2% (v/v) FBS, 2 mM L-glutamine and 2 mM L-glutamine, 1,000 U penicillin and 1,000 µg streptomycin (DMEM-2% FBS), on ice. Upon gelling at 37° C., 1 mL of DMEM-2% FBS was added along with the test compound indicated in the presence of 10 µM forskolin. Media was replenished every 2 days for 10 days; at every feed, test compound and forskolin were added.

Phase-contrast images were obtained every 2 days for 10 days. Per condition, 10 images were taken (in duplicate) and the average cyst area calculated.

Example A inhibited in vitro cyst formation in the OX161 cells in a concentration dependent manner.

The day 10 phase-contrast images and cyst area graphs for Example A are shown in FIG. 13 (Panel A).

Experiment 10: Reversal of In Vitro Cyst Formation in OX161 Cells Treated with PDE4 Long Form Activators of the Present Invention In this study, the potential of PDE4 long form activators to reverse the formation of pre-formed cysts was evaluated in a human ADPKD patient-derived OX161 cell line. The experiment was carried out according to the method of Experiment 9. For the first 10 days, forskolin was added at every feed (every 2 days) but no test compound was added. For the next 10 days, the test compound and forskolin were added at every feed (every 2 days).

Phase-contrast images were obtained every 2 days for 20 days. Per condition, 10 images were taken (in duplicate) and the average cyst area calculated.

Example A reversed in vitro cyst formation in the OX161 cells in a concentration dependent manner.

The day 20 phase-contrast images and cyst area graphs for Example A are shown in FIG. 13 (Panel B).

TABLE 1

Novel small molecule PDE4 long form activators of Formula 1 and Formula 2
(Examples A to L), according to the present invention

| Compound | Chemical name | Molecular weight (Daltons) | Chemical Structure |
|---|---|---|---|
| Example A | N-(3-Fluorobenzyl)-2-[3-(4-chloro-3-fluorophenyl)-5-ethyl-1H-1,2,4-triazol-1-yl]acetamide | 390.8 | 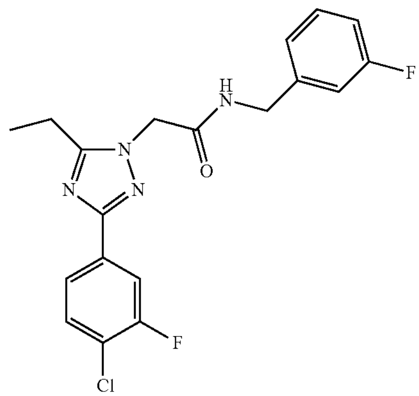 [SMILES: CCc1nc(-c2ccc(Cl)c(F)c2)nn1CC(=O)NCc1cccc(F)c1] |
| Example B | N-Benzyl-2-[3-(4-chlorophenyl)-5-methoxymethyl-1H-1,2,4-triazol-1-yl]acetamide | 370.8 | 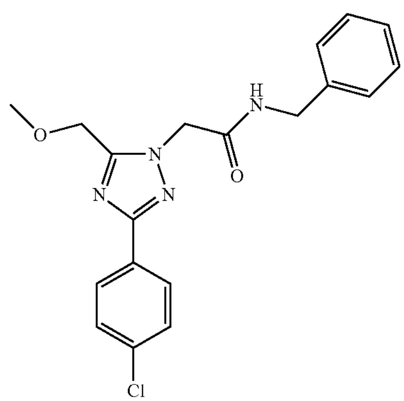 [SMILES: COCc1nc(-c2ccc(Cl)cc2)nn1CC(=O)NCc1ccccc1] |
| Example C | N-Benzyl-2-[3-(4-chlorophenyl)-5-methyl-1H-1,2,4-triazol-1-yl]acetamide | 340.8 | 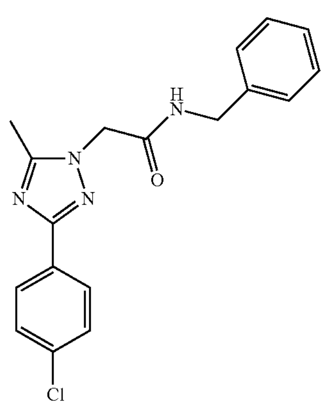 [SMILES: Cc1nc(-c2ccc(Cl)cc2)nn1CC(=O)NCc1ccccc1] |

TABLE 1-continued

Novel small molecule PDE4 long form activators of Formula 1 and Formula 2
(Examples A to L), according to the present invention

| Compound | Chemical name | Molecular weight (Daltons) | Chemical Structure |
|---|---|---|---|
| Example D | N-(3-Fluorobenzyl)-2-{3-[4-(trifluoromethoxy)-phenyl]-5-methoxymethyl-1H-1,2,4-triazol-1-yl}acetamide | 438.4 | 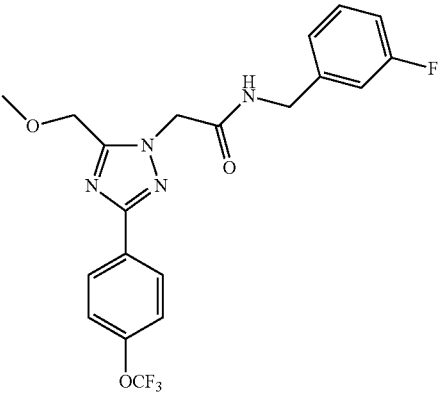 [SMILES: COCc1nc(-c2ccc(OC(F)(F)F)cc2)nn1CC(=O)NCc1cccc(F)c1] |
| Example E | N-(3-Chlorobenzyl)-2-[3-(4-chloro-3-flurophenyl)-5-ethyl-1H-1,2,4-triazol-1-yl]acetamide | 407.3 | 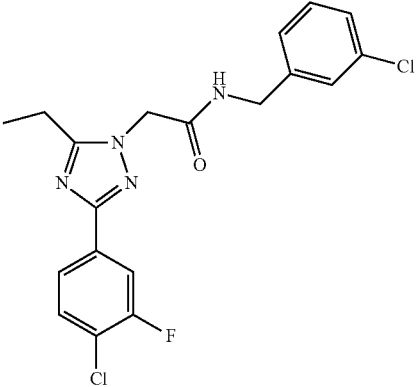 [SMILES: CCc1nc(-c2ccc(Cl)c(F)c2)nn1CC(=O)NCc1cccc(Cl)c1] |
| Example F | N-(3-Cyanobenzyl)-2-[3-(4-chloro-3-fluorophenyl)-5-ethyl-1H-1,2,4-triazol-1-yl]acetamide | 397.8 | 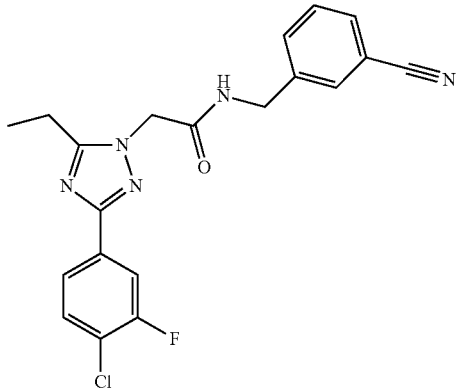 [SMILES: CCc1nc(-c2ccc(Cl)c(F)c2)nn1CC(=O)NCc1cccc(C#N)c1] |

TABLE 1-continued

Novel small molecule PDE4 long form activators of Formula 1 and Formula 2 (Examples A to L), according to the present invention

| Compound | Chemical name | Molecular weight (Daltons) | Chemical Structure |
|---|---|---|---|
| Example G | N-[3-(Trifluoromethyl)benzyl]-2-[3-(4-chloro-3-fluorophenyl)-5-ethyl-1H-1,2,4-triazol-1-yl]acetamide | 440.8 | 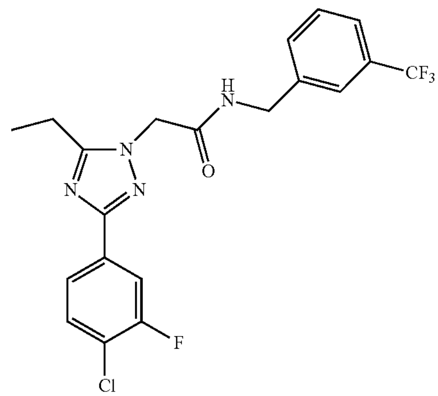 [SMILES: CCc1nc(-c2ccc(Cl)c(F)c2)nn1CC(=O)NCc1cccc(C(F)(F)F)c1] |
| Example H | N-(3-Methoxybenzyl)-2-[3-(4-chloro-3-fluorophenyl)-5-ethyl-1H-1,2,4-triazol-1-yl]acetamide | 402.8 | 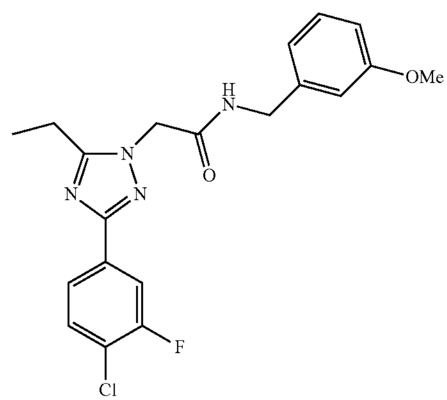 [SMILES: CCc1nc(-c2ccc(Cl)c(F)c2)nn1CC(=O)NCc1cccc(OC)c1] |
| Example I | N-[3-(Trifluoromethoxy)benzyl]-2-[3-(4-chloro-3-fluorophenyl)-5-ethyl-1H-1,2,4-triazol-1-yl]acetamide | 456.8 | 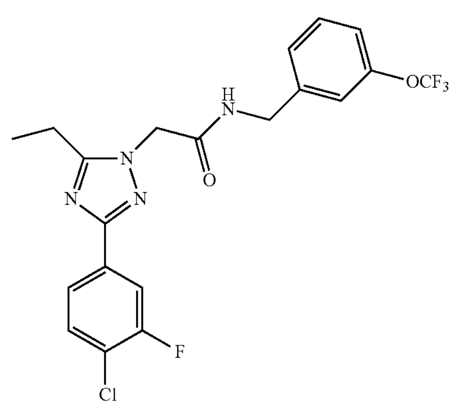 [SMILES: CCc1nc(-c2ccc(Cl)c(F)c2)nn1CC(=O)NCc1cccc(OC(F)(F)F)c1] |

TABLE 1-continued

Novel small molecule PDE4 long form activators of Formula 1 and Formula 2
(Examples A to L), according to the present invention

| Compound | Chemical name | Molecular weight (Daltons) | Chemical Structure |
|---|---|---|---|
| Example J | N-(2-Fluorobenzyl)-2-[3-(4-chloro-3-fluorophenyl)-5-ethyl-1H-1,2,4-triazol-1-yl]acetamide | 390.8 | 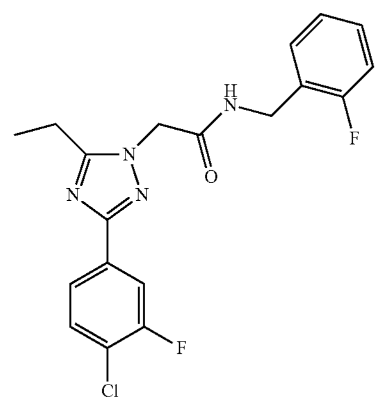 [SMILES: CCc1nc(-c2ccc(Cl)c(F)c2)nn1CC(=O)NCc1ccccc1F] |
| Example K | N-(4-Fluorobenzyl)-2-[3-(4-chloro-3-fluorophenyl)-5-ethyl-1H-1,2,4-triazol-1-yl]acetamide | 390.8 | 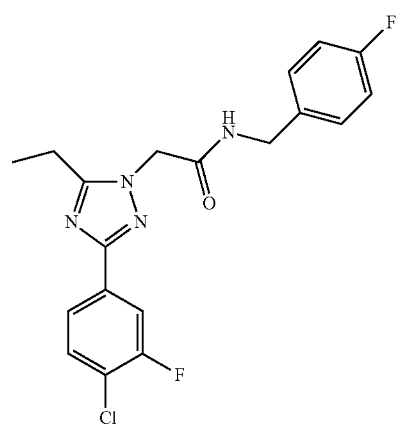 [SMILES: CCc1nc(-c2ccc(Cl)c(F)c2)nn1CC(=O)NCc1ccc(F)cc1] |
| Example L | N-(3,4-Dimethoxybenzyl)-2-[3-(4-chloro-3-fluorophenyl)-5-ethyl-1H-1,2,4-triazol-1-yl]acetamide | 432.9 | 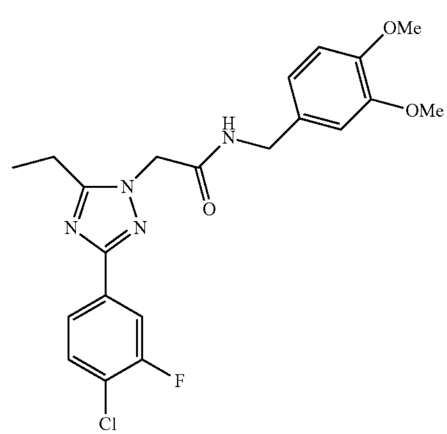 [SMILES: CCc1nc(-c2ccc(Cl)c(F)c2)nn1CC(=O)NCc1ccc(OC)c(OC)c1] |

Using the method described in Experiment 1, the compounds shown in Table 1 were identified as PDE4 long form activators.

TABLE 2

Activation of PDE4D5, a long form of PDE4, by Examples A to L
Using the method described in Experiment 1, the following
concentration/PDE4D5 activity data were obtained for Examples
A to L. Data are shown in graphical form in FIG. 1.

| Compound | Concentration (μM) | PDE4D5 activity* | SEM |
|---|---|---|---|
| Example A | 1 | −3.6 | 6.7 |
| Example A | 3 | −0.2 | 9.5 |
| Example A | 10 | 12.5 | 13.4 |
| Example A | 30 | 39.7 | 15.7 |
| Example A | 50 | 91.9 | 13.1 |
| Example B | 1 | 7.2 | 11.1 |
| Example B | 3 | 0.4 | 6.3 |
| Example B | 10 | 21.9 | 6.6 |
| Example B | 30 | 64.6 | 24.9 |
| Example B | 50 | 113.8 | 13.7 |
| Example C | 50 | 118.7 | 24.1 |
| Example D | 1 | 52.6 | 27.2 |
| Example D | 3 | 30.6 | 9.0 |
| Example D | 10 | 51.6 | 13.2 |
| Example D | 30 | 126.2 | 32.2 |
| Example D | 50 | 196.3 | 58.1 |
| Example E | 50 | 71.1 | 12.9 |
| Example F | 50 | 107.3 | 41.7 |
| Example G | 50 | 171.1 | 6.4 |
| Example H | 50 | 136.4 | 40.3 |
| Example I | 50 | 92.1 | 7.8 |
| Example J | 50 | 82.2 | 17.9 |
| Example K | 50 | 80.5 | 8.5 |
| Example L | 1 | 26.0 | 13.8 |
| Example L | 3 | 42.4 | 26.9 |
| Example L | 10 | 79.8 | 29.9 |
| Example L | 30 | 213.6 | 44.8 |
| Example L | 50 | 250.9 | 56.2 |

*Measured as mean % increase in counts over basal activity without added compound (n ≥ 2)

TABLE 3

Activation of PDE4A4, another long form of PDE4, by Example A
Using the method described in Experiment 1, the following
concentration/PDE4A4 activity data were obtained for Example A.
Data are shown in graphical form in FIG. 2.

| Compound | Concentration (μM) | PDE4A4 activity* | SEM |
|---|---|---|---|
| Example A | 1 | 1.1 | 8.8 |
| Example A | 3 | 2.7 | 1.3 |
| Example A | 10 | 10.4 | 5.2 |
| Example A | 30 | 38.5 | 8.7 |
| Example A | 50 | 65.4 | 25.0 |

*Measured as mean % increase in counts over basal activity without added compound (n ≥ 2)

TABLE 4

Activation of PDE4B1, another long form of PDE4, by Example A
Using the method described in Experiment 1, the following
concentration/PDE4B1 activity data were obtained for Example A.
Data are shown in graphical form in FIG. 3.

| Compound | Concentration (μM) | PDE4B1 activity* | SEM |
|---|---|---|---|
| Example A | 1 | −2.4 | 3.4 |
| Example A | 3 | 4.9 | 6.3 |
| Example A | 10 | 22.0 | 5.1 |
| Example A | 30 | 61.3 | 5.8 |
| Example A | 50 | 92.9 | 7.5 |

*Measured as mean % increase In counts over basal activity without added compound (n ≥ 2)

The invention claimed is:

1. A method of activating long isoforms of PDE4 comprising administering to a subject an effective amount of a compound of Formula 1:

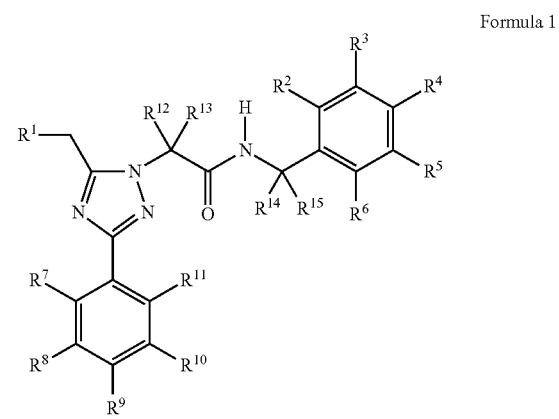

Formula 1 wherein
R$^1$ is selected from H, (C1-4)alkyl and (C1-4)alkyloxy, the (C1-4)alkyl and (C1-4)alkyloxy groups being optionally substituted with 1 to 3 fluoros;
R$^2$ and R$^6$ are independently selected from H, (C1-4)alkyl, (C1-4)alkyloxy, CN and halogen, the (C1-4)alkyl and (C1-4)alkyloxy groups being optionally substituted with 1 to 3 fluoros;
R$^3$, R$^4$ and R$^5$ are independently selected from H, (C1-4)alkyl, (C1-4)alkyloxy, (C1-4)alkylsulfonyl, C(O)—NR$^{16}$R$^{17}$, C(O)—OR$^{16}$, S(O)$_2$—NR$^{16}$R$^{17}$, CN and halogen, the (C1-4)alkyl and (C1-4)alkyloxy groups being optionally substituted with 1 to 3 fluoros;
R$^7$, R$^8$, R$^{10}$ and R$^{11}$ are independently selected from H and F;
R$^9$ is selected from H, (C1-4)alkyl, (C1-4)alkyloxy, (C1-4)alkylsulfonyl, C(O)-NR$^{16}$R$^{17}$, C(O)-OR$^{16}$, S(O)$_2$-NR$^{16}$R$^{17}$, CN and halogen, the (C1-4)alkyl and (C1-4)alkyloxy groups being optionally substituted with 1 to 3 fluoros;
R$^{12}$, R$^{13}$, R$^{14}$ and R$^{15}$ are independently selected from H and (C1-4)alkyl;
each R$^{16}$ and R$^{17}$, when present, is independently selected from H and (C1-4)alkyl;
or a pharmaceutically acceptable salt thereof.

2. A method of lowering excessive intracellular cyclic AMP signaling comprising administering to a patient signalling, comprising administering to a patient in need thereof an effective amount of a compound of Formula 1:

Formula 1

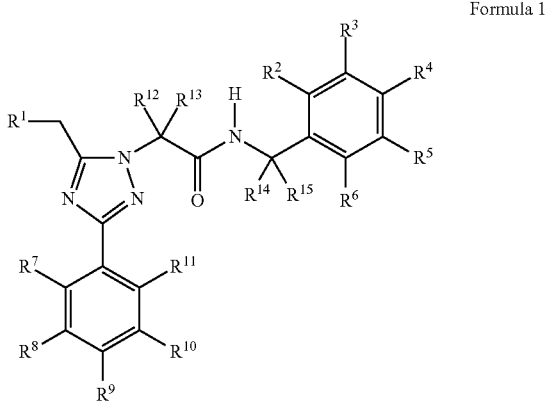

wherein
R¹ is selected from H, (C1-4)alkyl and (C1-4)alkyloxy, the (C1-4)alkyl and (C1-4)alkyloxy groups being optionally substituted with 1 to 3 fluoros;
R² and R⁶ are independently selected from H, (C1-4)alkyl, (C1-4)alkyloxy, CN and halogen, the (C1-4)alkyl and (C1-4)alkyloxy groups being optionally substituted with 1 to 3 fluoros;
R³, R⁴ and R⁵ are independently selected from H, (C1-4) alkyl, (C1-4)alkyloxy, (C1-4)alkylsulfonyl, C(O)-NR¹⁶R¹⁷, C(O)-OR¹⁶, S(O)₂-NR¹⁶R¹⁷, CN and halogen, the (C1-4)alkyl and (C1-4)alkyloxy groups being optionally substituted with 1 to 3 fluoros;
R⁷, R⁸, R¹⁰ and R¹¹ are independently selected from H and F;
R⁹ is selected from H, (C1-4)alkyl, (C1-4)alkyloxy, (C1-4)alkylsulfonyl, C(O)-NR¹⁶R¹⁷, C(O)-OR¹⁶, S(O)₂-NR¹⁶R¹⁷, CN and halogen, the (C1-4)alkyl and (C1-4)alkyloxy groups being optionally substituted with 1 to 3 fluoros;
R¹², R¹³, R¹⁴ and R¹⁵ are independently selected from H and (C1-4)alkyl;
each R¹⁶ and R¹⁷, when present, is independently selected from H and (C1-4)alkyl;
or a pharmaceutically acceptable salt thereof, wherein the patient has a disease selected from the group consisting of:
a. pituitary adenoma, Cushing's disease, polycystic kidney disease or polycystic liver disease;
b. hyperthyroidism, Jansens's metaphyseal chondrodysplasia, hyperparathyroidism, or familial male-limited precocious puberty;
c. McCune-Albright syndrome;
d. cholera, whooping cough, anthrax, or tuberculosis;
e. HIV, AIDS, or Common Variable Immunodeficiency (CVID);
f. melanoma, pancreatic cancer, leukaemia, prostate cancer, adrenocortical tumours, testicular cancer, primary pigmented nodular adrenocortical diseases (PPNAD), or Carney Complex;
g. autosomal dominant polycystic kidney disease (AD-PKD) or autosomal recessive polycystic kidney disease (ARPKD);
h. maturity onset diabetes of young type 5 (MODY5); or
i. cardiac hypertrophy.
3. The method of claim 2, wherein the disease is prostate cancer.
4. The method of claim 2, wherein the disease is:
a. autosomal dominant polycystic kidney disease (AD-PKD); or
b. autosomal recessive polycystic kidney disease (AR-PKD).
5. A method of activating long isoforms of PDE4 comprising administering to a subject an effective amount of a compound of Formula 2:

Formula 2

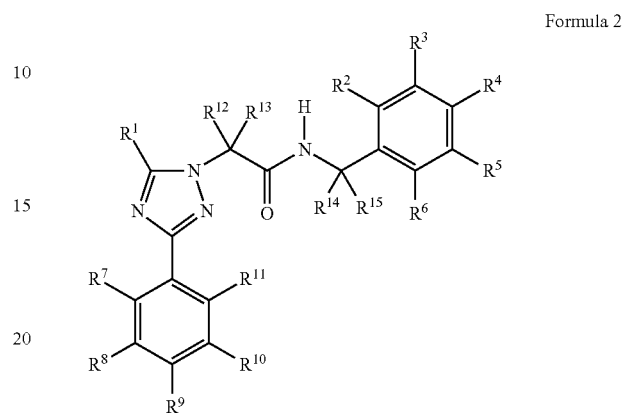

wherein
R¹ is H, (C1-6)alkyl and (C3-7)cycloalkyl, the (C1-6) alkyl and (C3-7)cycloalkyl groups being optionally substituted with 1 to 3 substituents selected from OH, (C1-4)alkyloxy, (C1-4)alkyl-sulfonyl, C(O)-NR¹⁶R¹⁷, C(O)-OR¹⁶, S(O)₂-NR¹⁶R¹⁷, CN and halogen;
R² and R⁶ are independently selected from H, (C1-4)alkyl, (C1-4)alkyloxy, CN and halogen, the (C1-4)alkyl and (C1-4)alkyloxy groups being optionally substituted with 1 to 3 fluoros;
R³, R⁴ and R⁵ are independently selected from H, (C1-4) alkyl, (C1-4)alkyloxy, (C1-4)alkylsulfonyl, C(O)-NR¹⁶R¹⁷, C(O)-OR¹⁶, S(O)₂-NR¹⁶R¹⁷, CN and halogen, the (C1-4)alkyl and (C1-4)alkyloxy groups being optionally substituted with 1 to 3 fluoros;
R⁷, R⁸, R¹⁰ and R¹¹ are independently selected from H and F;
R⁹ is selected from H, (C1-4)alkyl, (C1-4)alkyloxy, (C1-4)alkylsulfonyl, C(O)-NR¹⁶R¹⁷, C(O)-OR¹⁶, S(O)₂-NR¹⁶R¹⁷, CN and halogen, the (C1-4)alkyl and (C1-4)alkyloxy groups being optionally substituted with 1 to 3 fluoros;
R¹², R¹³, R¹⁴ and R¹⁵ are independently selected from H and (C1-4)alkyl;
each R¹⁶ and R¹⁷, when present, is independently selected from H and (C1-4)alkyl;
or a pharmaceutically acceptable salt thereof.
6. The method of claim 5, wherein the subject has excessive intracellular cyclic AMP signalling.
7. The method of claim 6, wherein the excessive intracellular cyclic AMP signalling is caused by:
a. excessive hormone levels produced by an adenoma;
b. a gain-of-function gene mutation in a G-protein coupled receptor (GPCR);
c. an activating mutation in the GNAS1 gene, which encodes the α-subunit of the G-protein G_s; or
d. a bacterial toxin.
8. The method of claim 5, wherein the subject has a disease selected from the group consisting of pituitary adenoma, Cushing's disease, polycystic kidney disease or polycystic liver disease, hyperthyroidism, Jansens's metaphyseal chondrodysplasia, hyperparathyroidism, familial male-limited precocious puberty, McCune-Albright syndrome; cholera, whooping cough, anthrax, or tuberculosis, HIV, AIDS, Common Variable Immunodeficiency (CVID), melanoma, pancreatic cancer, leukaemia, prostate cancer, adrenocortical tumours, testicular cancer, primary pigmented nodular adrenocortical diseases (PPNAD), Carney Complex; autosomal dominant polycystic kidney disease (ADPKD), autosomal recessive polycystic kidney disease (ARPKD), maturity onset diabetes of young type 5 (MODY5), and cardiac hypertrophy.

9. The method of claim 1, wherein the compounds of Formula I are selected from:

- N-(3-Fluorobenzyl)-2-[3-(4-chloro-3-fluorophenyl)-5-ethyl-1H-1,2,4-triazol-1-yl]acetamide;
- N-Benzyl-2-[3-(4-chlorophenyl)-5-methoxymethyl-1H-1,2,4-triazol-1-yl]acetamide;
- N-Benzyl-2-[3-(4-chlorophenyl)-5-methyl-1H-1,2,4-triazol-1-yl]acetamide;
- N-(3-Fluorobenzyl)-2-{3-[4-(trifluoromethoxy)-phenyl]-5-methoxymethyl-1H-1,2,4-triazol-1-yl}acetamide;
- N-(3-Chlorobenzyl)-2-[3-(4-chloro-3-fluorophenyl)-5-ethyl-1H-1,2,4-triazol-1-yl]acetamide;
- N-(3-Cyanobenzyl)-2-[3-(4-chloro-3-fluorophenyl)-5-ethyl-1H-1,2,4-triazol-1-yl]acetamide;
- N-[3-(Trifluoromethyl)benzyl]-2-[3-(4-chloro-3-fluorophenyl)-5-ethyl-1H-1,2,4-triazol-1-yl]acetamide;
- N-(3-Methoxybenzyl)-2-[3-(4-chloro-3-fluorophenyl)-5-ethyl-1H-1,2,4-triazol-1-yl]acetamide;
- N-[3-(Trifluoromethoxy)benzyl]-2-[3-(4-chloro-3-fluorophenyl)-5-ethyl-1H-1,2,4-triazol-1-yl]acetamide;
- N-(2-Fluorobenzyl)-2-[3-(4-chloro-3-fluorophenyl)-5-ethyl-1H-1,2,4-triazol-1-yl]acetamide;
- N-(4-Fluorobenzyl)-2-[3-(4-chloro-3-fluorophenyl)-5-ethyl-1H-1,2,4-triazol-1-yl]acetamide;
- N-(3,4-Dimethoxybenzyl)-2-[3-(4-chloro-3-fluorophenyl)-5-ethyl-1H-1,2,4-triazol-1-yl]acetamide;

and pharmaceutically acceptable salts thereof.

10. The method of claim 2, wherein the compounds of Formula I are selected from:

- N-(3-Fluorobenzyl)-2-[3-(4-chloro-3-fluorophenyl)-5-ethyl-1H-1,2,4-triazol-1-yl]acetamide;
- N-Benzyl-2-[3-(4-chlorophenyl)-5-methoxymethyl-1H-1,2,4-triazol-1-yl]acetamide;
- N-Benzyl-2-[3-(4-chlorophenyl)-5-methyl-1H-1,2,4-triazol-1-yl]acetamide;
- N-(3-Fluorobenzyl)-2-{3-[4-(trifluoromethoxy)-phenyl]-5-methoxymethyl-1H-1,2,4-triazol-1-yl}acetamide;
- N-(3-Chlorobenzyl)-2-[3-(4-chloro-3-fluorophenyl)-5-ethyl-1H-1,2,4-triazol-1-yl]acetamide;
- N-(3-Cyanobenzyl)-2-[3-(4-chloro-3-fluorophenyl)-5-ethyl-1H-1,2,4-triazol-1-yl]acetamide;
- N-[3-(Trifluoromethyl)benzyl]-2-[3-(4-chloro-3-fluorophenyl)-5-ethyl-1H-1,2,4-triazol-1-yl]acetamide;
- N-(3-Methoxybenzyl)-2-[3-(4-chloro-3-fluorophenyl)-5-ethyl-1H-1,2,4-triazol-1-yl]acetamide;
- N-[3-(Trifluoromethoxy)benzyl]-2-[3-(4-chloro-3-fluorophenyl)-5-ethyl-1H-1,2,4-triazol-1-yl]acetamide;
- N-(2-Fluorobenzyl)-2-[3-(4-chloro-3-fluorophenyl)-5-ethyl-1H-1,2,4-triazol-1-yl]acetamide;
- N-(4-Fluorobenzyl)-2-[3-(4-chloro-3-fluorophenyl)-5-ethyl-1H-1,2,4-triazol-1-yl]acetamide;
- N-(3,4-Dimethoxybenzyl)-2-[3-(4-chloro-3-fluorophenyl)-5-ethyl-1H-1,2,4-triazol-1-yl]acetamide;

and pharmaceutically acceptable salts thereof.

* * * * *

UNITED STATES PATENT AND TRADEMARK OFFICE
CERTIFICATE OF CORRECTION

PATENT NO. : 10,793,531 B2
APPLICATION NO. : 16/508001
DATED : October 6, 2020
INVENTOR(S) : Adam Page 1 of 1

It is certified that error appears in the above-identified patent and that said Letters Patent is hereby corrected as shown below:

In the Claims

In Claim 2 at Column 50, Line 65, delete "signaling comprising administering to a patient".

Signed and Sealed this
Twenty-ninth Day of December, 2020

Andrei Iancu
*Director of the United States Patent and Trademark Office*